United States Patent
Kasinath et al.

(10) Patent No.: US 10,537,661 B2
(45) Date of Patent: Jan. 21, 2020

(54) ORTHOPEDIC IMPLANT HAVING A CRYSTALLINE CALCIUM PHOSPHATE COATING AND METHODS FOR MAKING THE SAME

(71) Applicant: DEPUY SYNTHES PRODUCTS, INC., Raynham, MA (US)

(72) Inventors: Rajendra Kasinath, Warsaw, IN (US); Craig Ernsberger, Warsaw, IN (US); Stephanie Vass, Warsaw, IN (US); Steven N. Ginn, Granger, IN (US); Haibo Qu, Warsaw, IN (US); Weidong Tong, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/472,189

(22) Filed: Mar. 28, 2017

(65) Prior Publication Data

US 2018/0280571 A1    Oct. 4, 2018

(51) Int. Cl.
| | |
|---|---|
| A61L 27/32 | (2006.01) |
| A61L 27/06 | (2006.01) |
| A61L 27/56 | (2006.01) |
| A61L 27/58 | (2006.01) |
| A61L 27/54 | (2006.01) |
| B05D 1/18 | (2006.01) |
| B05D 3/00 | (2006.01) |
| C23C 16/40 | (2006.01) |
| C23C 16/455 | (2006.01) |
| C25D 9/04 | (2006.01) |

(52) U.S. Cl.
CPC .............. *A61L 27/32* (2013.01); *A61L 27/06* (2013.01); *A61L 27/54* (2013.01); *A61L 27/56* (2013.01); *A61L 27/58* (2013.01); *A61L 2300/112* (2013.01); *A61L 2300/412* (2013.01); *A61L 2300/606* (2013.01); *A61L 2400/12* (2013.01); *A61L 2420/02* (2013.01); *A61L 2430/02* (2013.01); *B05D 1/18* (2013.01); *B05D 3/002* (2013.01); *C23C 16/405* (2013.01); *C23C 16/45525* (2013.01); *C25D 9/04* (2013.01)

(58) Field of Classification Search
CPC ........ A61L 27/045; A61L 27/06; A61L 27/32; A61L 27/50; A61L 27/54; A61L 27/56; A61L 27/58; A61L 2300/112; A61L 2300/412; A61L 2300/606; A61L 2400/12; A61L 2420/02; A61L 2430/02; B05D 1/18; B05D 3/002; C23C 16/405; C23C 16/45525; C25D 9/04
See application file for complete search history.

(56) References Cited

U.S. PATENT DOCUMENTS

| | | |
|---|---|---|
| 5,015,817 A | 5/1991 | Kranz |
| 5,164,187 A | 11/1992 | Constantz et al. |
| 5,300,281 A | 4/1994 | McMillan et al. |
| 5,478,237 A | 12/1995 | Ishizawa |
| 5,558,517 A | 9/1996 | Shalaby et al. |
| 5,612,049 A | 3/1997 | Li et al. |
| 5,675,001 A | 10/1997 | Hoffman et al. |
| 5,691,397 A | 11/1997 | Glimcher et al. |
| 5,702,484 A | 12/1997 | Goymann et al. |
| 5,702,487 A | 12/1997 | Averill et al. |
| 5,763,092 A | 6/1998 | Lee et al. |
| 5,769,897 A | 6/1998 | Haerle |
| 5,944,757 A | 8/1999 | Grammont |
| 5,958,430 A | 9/1999 | Campbell et al. |
| 5,997,912 A | 12/1999 | Schlesinger et al. |
| 6,008,431 A | 12/1999 | Caldarise et al. |
| 6,013,591 A | 1/2000 | Ying et al. |
| 6,027,743 A | 2/2000 | Khouri et al. |
| 6,059,833 A | 5/2000 | Doets |
| 6,066,628 A | 5/2000 | Stojiljkovic et al. |
| 6,126,690 A | 10/2000 | Ateshian et al. |
| 6,139,585 A | 10/2000 | Li |
| 6,146,686 A | 11/2000 | Leitao |
| 6,153,664 A | 11/2000 | Wise et al. |
| 6,203,822 B1 | 3/2001 | Schlesinger et al. |
| 6,231,612 B1 | 5/2001 | Balay et al. |
| 6,261,322 B1 | 7/2001 | Despres et al. |

(Continued)

FOREIGN PATENT DOCUMENTS

| | | |
|---|---|---|
| DE | 102012210804 A1 | 1/2014 |
| EP | 375600 A2 | 6/1990 |

(Continued)

OTHER PUBLICATIONS

Alt et al Biomaterials, p. 4627, 2006.*
Charlotte Mellier et al., "Design and properties of novel gallium-doped injectable apatitic cements", Acta Biomaterialia, vol. 24, pp. 322-332, 2015, 11 pages.
Gabriela Ciobanu et al., "Structural characterization of hydroxyapatite layer coatings on titanium supports", Surface & Coatings Technology, vol. 202, pp. 2467-2470, 4 pages.

(Continued)

*Primary Examiner* — Matthew P Coughlin
*Assistant Examiner* — Thurman Wheeler
(74) *Attorney, Agent, or Firm* — Barnes & Thornburg LLP

(57) ABSTRACT

An orthopedic implant having a metal surface and a calcium phosphate layer disposed on at least part of the metal surface is described. The calcium phosphate layer has an average crystallite size of less than about 100 nm in at least one direction and dissolves for more than 2 hours in vitro. The calcium phosphate layer is substantially free of carbonate. The coating, which is formed on a sodium titanate surface, has increased shear strength and tensile strength. The coating is formed by a solution deposited hydroxyapatite process under inert conditions. The pH of the solution varies by less than 0.1 pH unit/hour during coating formation.

14 Claims, 20 Drawing Sheets

(56) References Cited

U.S. PATENT DOCUMENTS

| | | |
|---|---|---|
| 6,280,478 B1 | 8/2001 | Richter et al. |
| 6,280,789 B1 | 8/2001 | Rey et al. |
| 6,312,472 B1 | 11/2001 | Hall et al. |
| 6,319,255 B1 | 11/2001 | Grundei et al. |
| 6,319,286 B1 | 11/2001 | Fernandez et al. |
| 6,364,884 B1 | 4/2002 | Bowman et al. |
| 6,395,037 B1 | 5/2002 | Akashi et al. |
| 6,402,766 B2 | 6/2002 | Bowman et al. |
| 6,419,708 B1 | 7/2002 | Hall et al. |
| 6,436,110 B2 | 8/2002 | Bowman et al. |
| 6,488,716 B1 | 12/2002 | Huang et al. |
| 6,497,707 B1 | 12/2002 | Bowman et al. |
| 6,511,510 B1 | 1/2003 | de Bruijn et al. |
| 6,520,964 B2 | 2/2003 | Tallarida et al. |
| 6,569,489 B1 | 5/2003 | Li |
| 6,592,624 B1 | 7/2003 | Fraser et al. |
| 6,596,338 B2 | 7/2003 | Scott et al. |
| 6,602,293 B1 | 8/2003 | Biermann et al. |
| 6,610,095 B1 | 8/2003 | Pope et al. |
| 6,620,200 B1 | 9/2003 | Descamps et al. |
| 6,679,917 B2 | 1/2004 | Ek |
| 6,709,462 B2 | 3/2004 | Hanssen |
| 6,719,989 B1 | 4/2004 | Matsushima et al. |
| 6,736,849 B2 | 5/2004 | Li et al. |
| 6,764,769 B2 | 7/2004 | Kotte et al. |
| 6,846,327 B2 | 1/2005 | Khandkar et al. |
| 6,875,461 B2 | 4/2005 | Tanaka et al. |
| 6,908,486 B2 | 6/2005 | Lewallen |
| 6,911,048 B2 | 6/2005 | Fernandez et al. |
| 6,942,701 B2 | 9/2005 | Taylor |
| 7,044,976 B2 | 5/2006 | Meswania |
| 7,051,417 B2 | 5/2006 | Michelson |
| 7,087,086 B2 | 8/2006 | Li et al. |
| 7,105,030 B2 | 9/2006 | Despres, III et al. |
| 7,115,143 B1 | 10/2006 | Michelson |
| 7,192,448 B2 | 3/2007 | Ferree |
| 7,226,480 B2 | 6/2007 | Thalgott |
| 7,241,315 B2 | 7/2007 | Evans |
| 7,244,275 B2 | 7/2007 | Michelson |
| 7,341,756 B2 | 3/2008 | Liu et al. |
| 7,497,875 B1 | 3/2009 | Zweymiler |
| 7,521,436 B2 | 4/2009 | Bujoli et al. |
| 7,767,250 B2 | 8/2010 | Luan et al. |
| 7,892,286 B2 | 2/2011 | Michelson |
| 7,892,290 B2 | 2/2011 | Bergin et al. |
| 7,935,116 B2 | 5/2011 | Michelson |
| 7,998,219 B2 | 8/2011 | Riman et al. |
| 8,002,842 B2 | 8/2011 | Ronk |
| 8,021,433 B2 | 9/2011 | Meswania et al. |
| 8,044,037 B2 | 10/2011 | Bujoli et al. |
| 8,067,069 B2 | 11/2011 | Li |
| 8,071,156 B2 | 12/2011 | Weber et al. |
| 8,177,842 B2 | 5/2012 | Strzepa et al. |
| 8,187,304 B2 | 5/2012 | Malek |
| 8,252,062 B2 | 8/2012 | Bandoh et al. |
| 8,292,967 B2 | 10/2012 | Brown et al. |
| 8,303,879 B2 | 11/2012 | Bertele et al. |
| 8,323,348 B2 | 12/2012 | Lai et al. |
| 8,329,202 B2 | 12/2012 | Venu et al. |
| 8,399,008 B2 | 3/2013 | Webster et al. |
| 8,414,547 B2 | 4/2013 | DiFiore et al. |
| 8,414,650 B2 | 4/2013 | Bertele et al. |
| 8,486,151 B2 | 7/2013 | Theillez et al. |
| 8,506,644 B1 | 8/2013 | Ho Ba Tho et al. |
| 8,512,732 B2 | 8/2013 | Yao et al. |
| 8,535,751 B2 | 9/2013 | Gillesberg |
| 8,556,972 B2 | 10/2013 | Gordon et al. |
| 8,623,311 B2 | 1/2014 | Bujoli et al. |
| 8,628,584 B2 | 1/2014 | Blunn et al. |
| 8,637,090 B2 | 1/2014 | Ohtake et al. |
| 8,641,773 B2 | 2/2014 | Bergin et al. |
| 8,647,390 B2 | 2/2014 | Bellemere et al. |
| 8,663,329 B2 | 3/2014 | Ernst |
| 8,696,759 B2 | 4/2014 | Tong et al. |
| 8,702,806 B2 | 4/2014 | Balay et al. |
| 9,975,772 B2 | 5/2018 | Kjellin |
| 2002/0035402 A1 | 3/2002 | de Bruijn et al. |
| 2002/0134667 A1 | 9/2002 | Driskell et al. |
| 2003/0108658 A1 | 6/2003 | Andersch et al. |
| 2004/0023784 A1 | 2/2004 | Yu et al. |
| 2004/0053197 A1 | 3/2004 | Minevski et al. |
| 2004/0166139 A1 | 8/2004 | Stroosnijder et al. |
| 2004/0171471 A1 | 9/2004 | Nrenberg et al. |
| 2005/0100578 A1 | 5/2005 | Schmid et al. |
| 2006/0134160 A1 | 6/2006 | Troczynski et al. |
| 2007/0055380 A1 | 3/2007 | Berelsman et al. |
| 2008/0097618 A1 | 4/2008 | Baker et al. |
| 2008/0152783 A1 | 6/2008 | Andersch et al. |
| 2008/0220233 A1 | 9/2008 | Kjellin et al. |
| 2009/0276056 A1 | 11/2009 | Bose et al. |
| 2009/0280156 A1 | 11/2009 | Hotokebuchi et al. |
| 2010/0040668 A1 | 2/2010 | Riman et al. |
| 2010/0112208 A1 | 5/2010 | Malik et al. |
| 2010/0216697 A1 | 8/2010 | Duewelhenke |
| 2010/0248191 A1 | 9/2010 | Bujoli et al. |
| 2011/0020419 A1 | 1/2011 | Yuan et al. |
| 2011/0038809 A1 | 2/2011 | Perl et al. |
| 2011/0135621 A1 | 6/2011 | Miller et al. |
| 2012/0088100 A1 | 4/2012 | Ha et al. |
| 2012/0111226 A1 | 5/2012 | Bujoli et al. |
| 2012/0128729 A1 | 5/2012 | Ohtake et al. |
| 2012/0245135 A1 | 9/2012 | Thottathil et al. |
| 2012/0270031 A1 | 10/2012 | Guan et al. |
| 2012/0288699 A1 | 11/2012 | Ahlberg et al. |
| 2013/0078476 A1 | 3/2013 | Riman et al. |
| 2013/0110252 A1 | 5/2013 | Bake et al. |
| 2013/0209377 A1 | 8/2013 | Tas |
| 2013/0209537 A1 | 8/2013 | Fu-Giles |
| 2013/0247357 A1 | 9/2013 | Bertele et al. |
| 2013/0251982 A1 | 9/2013 | Kjellin et al. |
| 2013/0266629 A1 | 10/2013 | Arvidsson |
| 2013/0273135 A1 | 10/2013 | Brooks et al. |
| 2013/0302427 A1 | 11/2013 | Arvidsson et al. |
| 2013/0345827 A1 | 12/2013 | Wallick |
| 2014/0087004 A1 | 3/2014 | Bujoli et al. |
| 2014/0308628 A1 | 10/2014 | Carrad |

FOREIGN PATENT DOCUMENTS

| | | |
|---|---|---|
| EP | 450939 A2 | 10/1991 |
| EP | 532421 A1 | 3/1993 |
| EP | 578345 A1 | 1/1994 |
| EP | 743050 A1 | 11/1996 |
| EP | 764168 A1 | 3/1997 |
| EP | 900552 A1 | 3/1999 |
| EP | 1099426 A1 | 5/2001 |
| EP | 554301 B1 | 7/2001 |
| EP | 1136045 A2 | 9/2001 |
| EP | 1151732 A1 | 11/2001 |
| EP | 1207820 A1 | 5/2002 |
| EP | 1216667 A1 | 6/2002 |
| EP | 1011541 B1 | 10/2003 |
| EP | 1433443 A1 | 6/2004 |
| EP | 1168989 B1 | 9/2004 |
| EP | 1178765 B1 | 9/2004 |
| EP | 1527758 A1 | 5/2005 |
| EP | 1649834 A1 | 4/2006 |
| EP | 1786484 B1 | 2/2008 |
| EP | 1731115 B1 | 3/2008 |
| EP | 1917051 B1 | 6/2010 |
| EP | 2219696 A1 | 8/2010 |
| EP | 2228079 A1 | 9/2010 |
| EP | 2296718 B1 | 3/2013 |
| WO | 9110437 A1 | 7/1991 |
| WO | 02085385 A2 | 10/2002 |
| WO | 03061579 A2 | 7/2003 |
| WO | 2005058331 A1 | 6/2005 |
| WO | 2007085852 A2 | 8/2007 |
| WO | 2007087461 A2 | 8/2007 |
| WO | 2009024778 A2 | 2/2009 |
| WO | 2009111300 A2 | 9/2009 |
| WO | 2009111307 A2 | 9/2009 |

(56) References Cited

FOREIGN PATENT DOCUMENTS

| WO | 2010100209 A1 | 9/2010 |
|---|---|---|
| WO | 2011035434 A1 | 3/2011 |
| WO | 2014027612 A1 | 2/2014 |

OTHER PUBLICATIONS

P. Melnikov et al., "Gallium-containing hydroxyapatite for potential use in orthopedics", Materials Chemistry and Physics, vol. 117, Issue 1, pp. 86-90, Sep. 15, 2009, 5 pages.
European Search Report, European Application No. 18161421.5-1109, dated Aug. 14, 2018, 10 pages.
European Search Report, European Application No. 18161429.8-1109, dated Aug. 27, 2018, 10 pages.
Esenli et al., "X-Ray Diffraction Intensity Ratios I(111)/I(311) of Natural Heulandites And Clinoptilolites," Clays and Clay Minerals, vol. 46, No. 6, 1998, 679-686.
Kumar et al., "Chitosan-mediated crystallization and assembly of hydroxyapatite nanoparticles into hybrid nanostructured films," J.R. Soc. Interface (2008) 5, 427-439.
European Search Report and Opinion prepared for EP Application No. 18161429.8, 7 pages.
Kumar et al., "Temperature Driven Morphological Changes of Chemically Precipitated Hydroxyapatite Nanoparticles," Langmuir, vol. 20, No. 13, 2004, 5196-5200.
Tung, M. et al., "An Intermediate State in Hydrolysis of Amorphous Calcium Phosphate," Calcified Tissue International, 1983, 35, 783-790.
Blumenthal, N. et al., "Effect of gallium on the in vitro formation, growth, and solubility of hydroxyapatite," Calcified Tissue International, 1989, 45, 81-87.
Manca, S.G. et al, "Uber den Einbau von Al(III), Ga (III) und In(III) in das Calcium-Fluoroapatit-Gitter," Naturforsch, 1991, 46b, 129-131.
Cuisinier, F.J.G. et al., "High resolution electron microscopic study of Ga-containing carbonate apattite," Journal of Crystal Growth, 1992, 125, 1-6.
Li, P. "Biomimetic nano-apatite coating capable of promoting bone ingrowth," J. Biomedical Materials Research, 2003, 66A, 79-85.
Korbas, M. et al., "Bone tissue incorporates in vitro gallium with a local structure similar to gallium-doped brushite," Journal Biol Inorg Chem, 2004, 9, 67-76.
Melnikov, P. et al., "Gallium-containing hydroxyapatite for potential use in orthopedics," Materials Chemistry and Physics, 2009, 117, 86-90.
Kolmas, J. et al., "Substituted Hydroxyapatites with Antibacterial Properties," BioMed Research International, 2014, Article ID 178123, 15 pages.
Inagaki, M. et al., "Phase transformation of plasma-sprayed hydroxyapaptite coating with preferred crystalline orientation," Biomaterials, 2007, 28, 2923-2931.
Bernstein, L. R., "Mechanisms of Therapeutic Activity for Gallium," Pharmacological Reviews, 1999, 50, 665-82.
Mellier, C. et al., "Design and properties of novel gallium-doped injectable apatitic cements," Acta Biomaterialia, 2015, 24, 322-332.
Donnelly, R. et al., "The Effect of Gallium on Seeded Hydroxyapatite Growth," Calcif. Tissue Int., 1989, 44, 138-142.
Kurtjak et al., Biocompatible nano-gallium/hydroxapatite nanocomposite with antimicrobial activity, J. Matter.Sci: Mater Med, 27: 170, pp. 1-13. (Year: 2016).

\* cited by examiner

ORTHOPEDIC IMPLANT HAVING A CRYSTALLINE CALCIUM PHOSPHATE COATING AND METHODS FOR MAKING THE SAME

CROSS-REFERENCE TO RELATED APPLICATIONS

Cross reference is made to copending U.S. patent application Ser. No. 15/472,186 entitled "ORTHOPEDIC IMPLANT HAVING A CRYSTALLINE GALLIUM-CONTAINING HYDROXYAPATITE COATING AND METHODS FOR MAKING THE SAME", which is hereby incorporated by reference.

FIELD OF THE INVENTION

The present invention relates generally to a calcium phosphate coating, and more particularly to an orthopedic implant having a solution deposited calcium phosphate coating and methods for making the same.

BACKGROUND OF THE INVENTION

Bone repair often involves the use of orthopedic implants to replace missing bone or support bone during the healing process. It is typically desirable to coat such orthopedic implants with osteoconductive materials to encourage bone growth or biological fixation.

Hydroxyapatite (HA) is a naturally occurring mineral found in bones and teeth. Studies have shown that HA is osteoconductive, and orthopedic implants have been coated with HA for this reason. Octacalcium Phosphate has also been reported to be osteoconductive. Various processes for coating implants with CaP and HA are known. One process used for coating implants is plasma spray. In this process, HA powder is fed into a high temperature torch with a carrier gas. The HA powder is partially melted and then impacts the substrate at high velocity whereupon it is rapidly quenched back to room temperature. This process produces a mixture of HA, other calcium phosphate phases, and amorphous calcium phosphate. These phases have wide differences in solubility in vivo. As a result, plasma sprayed hydroxyapatite (PSHA) films do not uniformly dissolve or degrade in vivo. This non-homogenous degradation can generate particulates in the vicinity of the implant which can result in an inflammatory cascade leading to osteolysis. The particles may also find their way into joint articular surfaces, resulting in increased wear. Finally, the process is not well suited for coating porous structures of cementless implants because it is a "line of sight" process. PSHA processing or post processing methods can be applied that result in highly crystalline coatings with long resorption times in-vivo. This attribute gives rise to concerns over long term delamination of these relatively thick stable coatings.

Other methods to produce HA coatings for biological fixation include physical methods such as sputtering, evaporation, and chemical vapor deposition. These physical methods do not reproduce the nano-crystallinity and high surface area of biological apatites, and the resulting coatings may not uniformly dissolve and may release particulates.

Solution (or suspension) methods for producing HA coatings have also been attempted. For example, Zitelli, Joseph P. and Higham, Paul (2000), A Novel Method For Solution Deposition of Hydroxyapatite Onto Three Dimensionally Porous Metallic Surfaces: Peri-Apatite HA describes a process that involves producing a slurry of finely divided HA particles into which implants are placed and coated by accretion of the slurry particles. High surface area, microcrystalline coatings are produced, but their adhesion to the substrate is poor.

Electrochemically assisted solution deposition has also been developed. In this process, a voltage exceeding that necessary to hydrolyze water is applied to an implant while the implant is suspended in an aqueous solution. This process results in deposition of calcium phosphate material on the implant. Typically, the deposited film is a mixture of calcium phosphate (CaP) phases and requires post processing to convert the films to phase pure HA. Poor adhesion is also a concern with these films. Finally, control of electrochemical currents on porous implants with irregular particles is challenging, making this process difficult to scale.

Biomimetic processes have also been developed. These processes employ solutions mimicking body fluid concentrations and are typically performed near body temperature. These processes can yield bone-like apatite but require days or weeks to produce films a few microns thick. Attempts to increase rates associated with such methods have led to complications in reproducibly controlling pH, deposition rate, and accretion rate compared to crystalline growth on the surface of the implant. Films formed at higher rates have been found to contain amorphous material. Uncontrolled deposition rate also makes it difficult to achieve target coating weights or thicknesses.

As described above, hydroxyapatite coatings may be applied to orthopedic implants to enhance osteoconductivity using methods that are either rapid but lead to coatings having certain undesirable or unpredictable properties or lead to more desirable products but can take days to form. What is needed is a conformal calcium phosphate coating that can be rapidly formed and has a microstructure that lends itself to uniform degradation over a period of several weeks without generating particulates.

SUMMARY OF THE DISCLOSURE

Several embodiments of the invention are described by the following enumerated clauses:

1. An orthopedic implant comprising a metal surface and a calcium phosphate layer disposed on at least part of the metal surface, wherein the calcium phosphate layer has an average crystallite size of less than about 100 nm in the [001] direction.

2. An orthopedic implant comprising a metal surface and a calcium phosphate layer disposed on at least part of the metal surface, wherein, the calcium phosphate layer, when subjected to XRD, produces a (002) XRD peak and a (112) XRD peak, and the (002) XRD peak has an intensity 1.5 to 10 times greater than the (112) XRD peak.

3. An orthopedic implant comprising a metal surface and a calcium phosphate layer disposed on at least part of the metal surface, wherein the calcium phosphate layer dissolves continuously for more than 2 hours in vitro.

4. An orthopedic implant comprising a metal surface and a calcium phosphate layer disposed on at least part of the metal surface, wherein the calcium phosphate layer is substantially free of carbonate as measured by infrared spectroscopy.

5. The orthopedic implant of any one of the preceding clauses, wherein the coating has an average crystallite size of about 10 to about 100 nm in the [001] direction.

6. The orthopedic implant of any one of the preceding clauses, wherein the calcium phosphate layer has an average crystallite size of about 15 nm to about 70 nm in the [001] direction.

7. The orthopedic implant of any one of the preceding clauses, wherein the calcium phosphate layer has an average crystallite size of about 50 nm to about 100 nm in the [001] direction.

8. The orthopedic implant of any one of the preceding clauses, wherein the calcium phosphate layer, when subjected to XRD, produces a (002) XRD peak and a (112) XRD peak, and the (002) XRD peak has an intensity 1.5 to 10 times greater than the (112) XRD peak.

9. The orthopedic implant of any one of the preceding clauses, wherein the calcium phosphate layer, when subjected to XRD, produces a (002) XRD peak and a (112) XRD peak, and the (002) XRD peak has an intensity 2 to 5 times greater than the (112) XRD peak.

10. The orthopedic implant of any one of the preceding clauses, wherein the calcium phosphate layer dissolves for more than 2 hours in vitro.

11. The orthopedic implant of any one of the preceding clauses, wherein the calcium phosphate layer dissolves for more than 5 hours in vitro.

12. The orthopedic implant of any one of the preceding clauses, wherein the calcium phosphate layer dissolves for more than 24 hours in vitro.

13. The orthopedic implant of any one of the preceding clauses, wherein the calcium phosphate layer is resorbed in vivo within 6 weeks.

14. The orthopedic implant of any one of the preceding clauses, wherein the calcium phosphate layer comprises about 0 wt % to about 5 wt % carbonate.

15. The orthopedic implant of any one of the preceding clauses, wherein the calcium phosphate layer is substantially free of carbonate as measured by infrared spectroscopy.

16. The orthopedic implant of any one of the preceding clauses, wherein the coating is in contact with the metal surface.

17. The orthopedic implant of any one of the preceding clauses, wherein the metal surface comprises a metal oxide.

18. The orthopedic implant of any one of the preceding clauses, wherein the metal surface comprises titanium.

19. The orthopedic implant of any one of the preceding clauses, wherein the metal surface comprises a cobalt chromium alloy.

20. The orthopedic implant of any one of the preceding clauses, wherein the metal surface comprises a titanium oxide.

21. The orthopedic implant any one of the preceding clauses, wherein the metal surface comprises a titanate.

22. The orthopedic implant of any one of the preceding clauses, wherein the metal surface comprises sodium titanate.

23. The orthopedic implant of any one of the preceding clauses, wherein the metal surface is a porous metal oxide surface.

24. The orthopedic implant of any one of the preceding clauses, wherein the metal surface is a titanium surface that has been treated with hydroxide.

25. The orthopedic implant of clause 24, wherein the hydroxide has a concentration of 1M or greater.

26. The orthopedic implant of clause 24 or 25, wherein the hydroxide has a concentration of 2M or greater.

27. The orthopedic implant of any one of clauses 24 to 26, wherein the hydroxide is sodium hydroxide.

28. The orthopedic implant of any one of clauses 24 to 27, wherein the hydroxide is potassium hydroxide.

29. The orthopedic implant of any one of clauses 24 to 28, wherein the titanium surface is not heat treated after being treated with the hydroxide.

30. The orthopedic implant of any one of the preceding clauses, wherein the metal surface has a thickness greater than about 50 nm.

31. The orthopedic implant of any one of the preceding clauses, wherein the metal surface has a thickness between about 50 nm and about 1 µm.

32. The orthopedic implant of any one of the preceding clauses, wherein the metal surface has a thickness between about 50 nm and about 100 nm.

33. The orthopedic implant of any one of the preceding clauses, wherein the calcium phosphate layer comprises hydroxyapatite, and the hydroxyapatite has a crystallinity of greater than about 90%.

34. The orthopedic implant of any one of the preceding clauses, wherein the calcium phosphate layer comprises hydroxyapatite, and the hydroxyapatite has a crystallinity of about 70 wt % to about 100 wt %.

35. The orthopedic implant of any one of the preceding clauses, wherein the calcium phosphate layer has a phase purity of crystalline hydroxyapatite of greater than 90%.

36. The orthopedic implant of any one of the preceding clauses, wherein the calcium phosphate layer has a shear strength of about 20 MPa to about 80 MPa.

37. The orthopedic implant of any one of the preceding clauses, wherein the calcium phosphate layer has a tensile strength of about 50 MPa to about 100 MPa as determined according to ASTM F1147.

38. The orthopedic implant of any one of the preceding clauses, wherein the calcium phosphate layer, in the absence of colorants, is transparent or translucent.

39. The orthopedic implant of any one of the preceding clauses, wherein the calcium phosphate layer has a Ca/P ratio of 1 to 2.

40. The orthopedic implant of any one of the preceding clauses, wherein the calcium phosphate layer has a surface area of about 15 m$^2$/g to about 200 m$^2$/g.

41. The orthopedic implant of any one of the preceding clauses, wherein the calcium phosphate layer does not release particulates under physiological conditions.

42. The orthopedic implant of any one of the preceding clauses, wherein the calcium phosphate layer comprises an apatite.

43. The orthopedic implant of any one of the preceding clauses, wherein the calcium phosphate layer comprises a hydroxyapatite.

44. The orthopedic implant of any one of the preceding clauses, wherein the calcium phosphate layer comprises calcium-deficient hydroxyapatite.

42. A method of treating a patient comprising administering to the patient the orthopedic implant of any one of the preceding clauses.

Additionally, several embodiments of the invention are described by the following enumerated clauses:

1. An osteoconductive composition comprising calcium phosphate, wherein the calcium phosphate has an average crystallite size of less than about 100 nm in the [001] direction.

2. An osteoconductive composition comprising calcium phosphate, wherein the calcium phosphate, when subjected to XRD, produces a (002) XRD peak and a (112) XRD peak, and the (002) XRD peak has an intensity 1.5 to 10 times greater than the (112) XRD peak.

3. An osteoconductive composition comprising calcium phosphate, wherein the calcium phosphate dissolves continuously for more than 2 hours in vitro.

4. An osteoconductive composition comprising calcium phosphate, wherein the calcium phosphate is substantially free of carbonate as measured by infrared spectroscopy.

5. The osteoconductive composition of any one of the preceding clauses, wherein the calcium phosphate has an average crystallite size of about 10 to about 100 nm in the [001] direction.

6. The osteoconductive composition of any one of the preceding clauses, wherein the calcium phosphate has an average crystallite size of about 15 nm to about 70 nm in the [001] direction.

7. The osteoconductive composition of any one of the preceding clauses, wherein the calcium phosphate has an average crystallite size of about 50 nm to about 100 nm in the [001] direction.

8. The osteoconductive composition of any one of the preceding clauses, wherein the calcium phosphate, when subjected to XRD, produces a (002) XRD peak and a (112) XRD peak, and the (002) XRD peak has an intensity 1.5 to 10 times greater than the (112) XRD peak.

9. The osteoconductive composition of any one of the preceding clauses, wherein the calcium phosphate, when subjected to XRD, produces a (002) XRD peak and a (112) XRD peak, and the (002) XRD peak has an intensity 2 to 5 times greater than the (112) XRD peak.

10. The osteoconductive composition of any one of the preceding clauses, wherein the calcium phosphate dissolves for more than 2 hours in vitro.

11. The osteoconductive composition of any one of the preceding clauses, wherein the calcium phosphate dissolves for more than 5 hours in vitro.

12. The osteoconductive composition of any one of the preceding clauses, wherein the calcium phosphate dissolves for more than 24 hours in vitro.

13. The osteoconductive composition of any one of the preceding clauses, wherein the calcium phosphate layer is resorbed in vivo within 6 weeks.

14. The osteoconductive composition of any one of the preceding clauses, wherein the calcium phosphate comprises about 0 wt % to about 5 wt % carbonate.

15. The osteoconductive composition of any one of the preceding clauses, wherein the calcium phosphate is substantially free of carbonate as measured by infrared spectroscopy.

16. The osteoconductive composition of any one of the preceding clauses, wherein the calcium phosphate is in contact with a metal surface.

17. The osteoconductive composition of clause 16, wherein the metal surface comprises a metal oxide.

18. The osteoconductive composition of clause 16 or 17, wherein the metal surface comprises titanium.

19. The osteoconductive composition of any one of clauses 16 to 18, wherein the metal surface comprises a cobalt chromium alloy.

20. The osteoconductive composition of any one of clauses 16 to 19, wherein the metal surface comprises a titanium oxide.

21. The osteoconductive composition of any one of clauses 16 to 20, wherein the metal surface comprises a titanate.

22. The osteoconductive composition of any one of clauses 16 to 21, wherein the metal surface comprises sodium titanate.

23. The osteoconductive composition of any one of clauses 16 to 22, wherein the metal surface is a porous metal oxide surface.

24. The osteoconductive composition of any one of clauses 16 to 23, wherein the metal surface is a titanium surface that has been treated with hydroxide.

25. The osteoconductive composition of clause 24, wherein the hydroxide has a concentration of 1M or greater.

26. The osteoconductive composition of clause 24 or 25, wherein the hydroxide has a concentration of 2M or greater.

27. The osteoconductive composition of any one of clauses 24 to 26, wherein the hydroxide is sodium hydroxide.

28. The osteoconductive composition of any one of clauses 24 to 27, wherein the hydroxide is potassium hydroxide.

29. The osteoconductive composition of any one of clauses 24 to 28, wherein the titanium surface is not heat treated after being treated with the hydroxide.

30. The osteoconductive composition of any one of clauses 24 to 29, wherein the metal surface has a thickness greater than about 50 nm.

31. The osteoconductive composition of any one of clauses 24 to 30, wherein the metal surface has a thickness between about 50 nm and about 1 μm.

32. The osteoconductive composition of any one of clauses 24 to 31, wherein the metal surface has a thickness between about 50 nm and about 100 nm.

33. The osteoconductive composition of any one of the preceding clauses, wherein the calcium phosphate comprises hydroxyapatite, and the hydroxyapatite has a crystallinity of greater than about 90%.

34. The osteoconductive composition of any one of the preceding clauses, wherein the calcium phosphate comprises hydroxyapatite, and the hydroxyapatite has a crystallinity of about 70 wt % to about 100 wt %.

35. The osteoconductive composition of any one of the preceding clauses, wherein the calcium phosphate has a phase purity of crystalline hydroxyapatite of greater than 90%.

36. The osteoconductive composition of any one of the preceding clauses, wherein the calcium phosphate has a shear strength of about 20 MPa to about 80 MPa as determined according to ASTM F1044.

37. The osteoconductive composition of any one of the preceding clauses, wherein the calcium phosphate has a tensile strength of about 50 MPa to about 100 MPa as determined according to ASTM F1147.

38. The osteoconductive composition of any one of the preceding clauses, wherein the calcium phosphate, in the absence of colorants, is transparent or translucent.

39. The osteoconductive composition of any one of the preceding clauses, wherein the calcium phosphate has a Ca/P ratio of 1 to 2.

40. The osteoconductive composition of any one of the preceding clauses, wherein the calcium phosphate has a surface area of about 15 m$^2$/g to about 200 m$^2$/g.

41. The osteoconductive composition of any one of the preceding clauses, wherein the calcium phosphate does not release particulates under physiological conditions.

42. The orthopedic implant of any one of the preceding clauses, wherein the calcium phosphate layer comprises an apatite.

43. The osteoconductive composition of any one of the preceding clauses, wherein the calcium phosphate comprises a hydroxyapatite.

44. The osteoconductive composition of any one of the preceding clauses, wherein the calcium phosphate comprises a calcium-deficient hydroxyapatite.

Additionally, several embodiments of the invention are described by the following enumerated clauses:

1. A method of forming a calcium phosphate coating, the method comprising contacting a metal surface with a supersaturated solution comprising calcium ions and phosphate ions and reducing the amount of air in contact with the supersaturated solution during the coating step.

2. A method of forming a calcium phosphate coating, the method comprising contacting a metal surface with a supersaturated solution comprising calcium ions and phosphate ions wherein the pH of the solution varies by less than 0.1 pH unit/hour during the contacting step.

3. A method of forming a calcium phosphate coating, the method comprising contacting a metal surface with a supersaturated solution comprising calcium ions and phosphate ions wherein crystalline calcium phosphate forms on the metal surface at a rate of 0.1 µm/h to 3 µm/h.

4. The method of any one of the preceding clauses, wherein the metal surface is a metal oxide surface.

5. The method of any one of the preceding clauses, wherein the calcium phosphate coating is formed on an orthopedic implant comprising the metal surface.

6. The method of any one of the preceding clauses, further comprising reducing the amount of air in contact with the supersaturated solution during the coating step.

7. The method of any one of the preceding clauses, wherein the pH of the supersaturated solution varies by less than 0.1 pH unit/hour during the contacting step.

8. The method of any one of the preceding clauses, further comprising allowing the pH to decrease during the contacting step by a predetermined value that is less than 0.15 pH units.

9. The method of any one of the preceding clauses, wherein crystalline calcium phosphate forms on the metal surface at a rate of 0.1 µm/h to 2 µm/h.

10. The method of any one of the preceding clauses, wherein the calcium phosphate is a calcium apatite.

11. The method of any one of the preceding clauses, wherein the calcium phosphate is a hydroxyapatite.

12. The method of any one of the preceding clauses, wherein the calcium phosphate is a calcium-deficient hydroxyapatite.

13. The method of any one of the preceding clauses, wherein the pH of the supersaturated solution is from about 7.5 to about 7.9.

14. The method of any one of the preceding clauses, wherein the concentration of calcium in the supersaturated solution is from about 1.4 mM to about 1.8 mM.

15. The method of any one of the preceding clauses, wherein the concentration of phosphate in the supersaturated solution is from about 2 mM to about 2.3 mM.

16. The method of any one of clauses 1 to 9, wherein the calcium phosphate is octacalcium phosphate.

17. The method of clause 16, wherein the pH of the supersaturated solution is about 6.9 to about 7.1.

18. The method of clause 16 or 17, wherein the concentration of calcium in the supersaturated solution is from about 0.5 mM to about 1.4 mM.

19. The method of any one of clauses 16 to 18, wherein the concentration of phosphate in the supersaturated solution is from about 0.1 mM to about 0.9 mM.

20. The method of any one of the preceding clauses, wherein the Gibbs free energy change associated with the forming step is from about 8 kJ/mol to about 8.4 kJ/mol when the forming step begins.

21. The method of any one of the preceding clauses, wherein the coating forms at a rate per unit surface area from about 0.01 mg/hr·mm$^2$ to 0.03 about mg/hr·mm$^2$.

22. The method of any one of the preceding clauses, further comprising removing the metal surface from the supersaturated solution after from about 0.5 hour to about 12 hours.

23. The method of clause 22, further comprising contacting the metal surface, after the removing step, with an additional amount of the supersaturated solution that has not contacted the metal surface.

24. The method of any one of the preceding clauses, wherein the temperature of the supersaturated solution is from about 45° C. to about 50° C.

25. The method of any one of the preceding clauses, wherein the temperature of the supersaturated solution is from about 46.5° C. to 47.5° C.

26. The method of any one of the preceding clauses, wherein the supersaturated solution further comprises a salt and a buffer.

27. The method of clause 26, wherein the salt is sodium chloride and the buffer is tris(hydroxymethyl)aminomethane.

28. The method of any one of the preceding clauses, further comprising agitating the supersaturated solution during the contacting step.

29. The method of any one of the preceding clauses, wherein heterogeneous crystal growth occurs on the metal surface and homogeneous crystal growth does not occur.

30. The method of any one of the preceding clauses, further comprising forming a titanium layer on an implant body to form the metal surface.

31. The method of any one of the preceding clauses, further comprising activating the metal surface by contacting the metal surface with a base.

32. The method of clause 31, wherein the base is a hydroxide anion.

33. The method of any one of the preceding clauses, wherein the metal surface is a titanium dioxide surface.

34. The method of any one of the preceding clauses, wherein the metal surface is an activated metal surface.

35. The method of any one of the preceding clauses, wherein the metal surface comprises a titanate.

36. The method any one of the preceding clauses, wherein the process occurs under inert atmospheric conditions.

37. The method of any one of the preceding clauses, wherein the process occurs under an argon atmosphere.

38. The method of any one of the preceding clauses, further comprising adding a calcium solution to a phosphate solution to form the supersatured solution, wherein the phosphate solution comprises sodium chloride and a buffer.

39. The method of any one of the preceding clauses, wherein the calcium solution and the phosphate solution are mixed at from about 15° C. to about 35° C.

40. The method of any one of the preceding clauses, wherein the calcium phosphate coating is not further treated to increase crystallinity after the contacting step.

41. The method of any one of the preceding clauses, wherein the method is validated for the amount of the calcium phosphate coating on the metal surface.

42. The method of any one of the preceding clauses, wherein the calcium phosphate coating is formed predominantly through heterogeneous nucleation such that the supersaturated solution remains visibly free of turbidity during the contacting step.

43. The method of any one of the preceding clauses, wherein the calcium phosphate coating forms at a substantially continuous rate throughout the contacting step.

44. The method of any one of the preceding clauses, further comprising determining the amount of the calcium phosphate coating based on the amounts of the calcium ions and the phosphate ions.

45. The method of any one of the preceding clauses, wherein at least two deposition sequences are employed.

46. The method of any one of the preceding clauses, further comprising determining the amount of the calcium phosphate coating based on the pH of the supersaturated solution.

47. The method of any one of the preceding clauses, further comprising deteriming the amount of the calcium phosphate coating based on the duration of the contacting step.

48. The method of any one of the preceding clauses, wherein the pH of the supersaturated solution varies by from about 0.01 to about 0.2 pH unit/hour during the contacting step.

49. The method of any one of the preceding clauses, wherein the coating forms at a rate per unit surface area from about 0.01 mg/hr·mm$^2$ to 0.03 about mg/hr·mm$^2$.

50. The method of any one of the preceding clauses, wherein the initial pH of the supersaturated solution is from about 7.5 to about 7.9, and the temperature of the supersaturated solution is from about 38° C. to about 60° C.

51. The method of any one of the preceding clauses, further comprising heating the coating in a phosphate solution to mitigate surface cracking.

52. The method of any one of the preceding clauses, further comprising contacting the coating with a supercritical fluid to mitigate surface cracking.

53. An osteoconductive composition formed according to the method of any one of the preceding clauses.

54. An orthopedic implant comprising an osteoconductive composition formed according to the method of any one of the preceding clauses.

The above and other objects, features, and advantages of the present invention will become apparent from the following description and the attached drawings.

DETAILED DESCRIPTION OF THE ILLUSTRATIVE EMBODIMENTS

Figure 1:
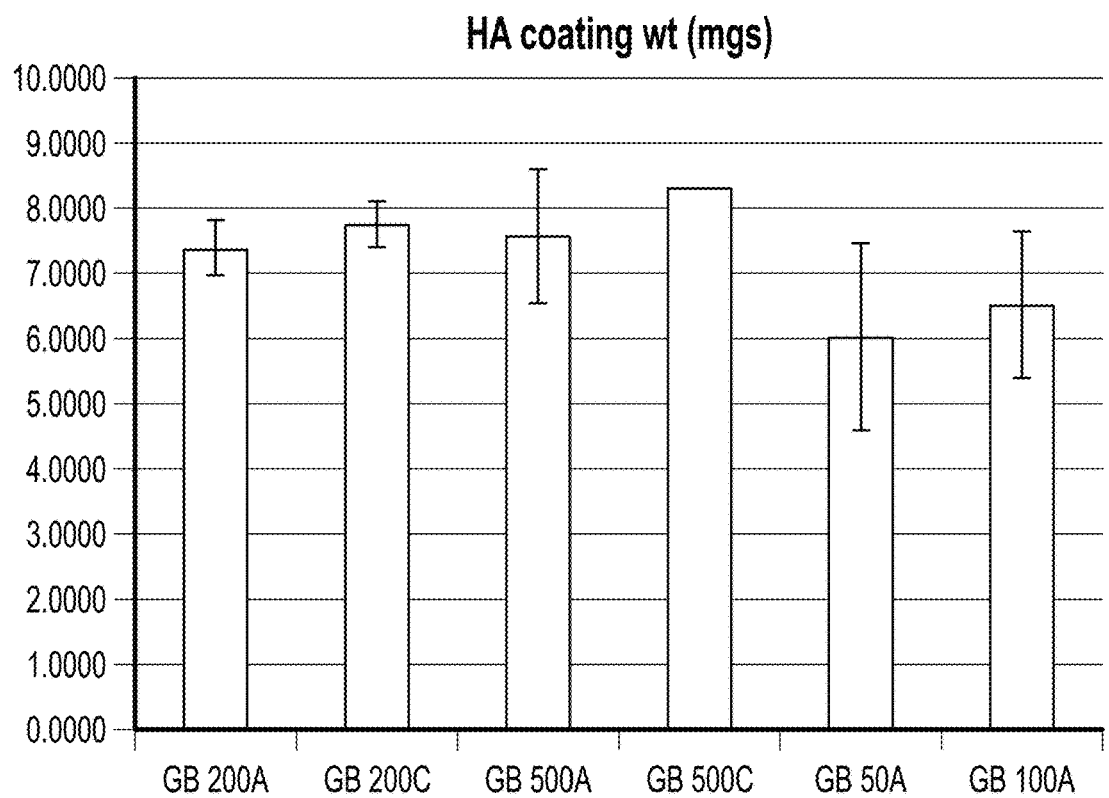
FIG. 1 is a chart showing the weights of hydroxyapatite coatings formed on crystalline and amorphous 50 nm- to 500 nm-thick titanium dioxide (TiO$_2$) coated substrates.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

The present invention relates to calcium phosphate coated orthopedic implants, such as hydroxyapatite (HA) and octacalcium phosphate (OCP) coated orthopedic implants, and methods of making the same. The calcium phosphate coatings described herein have a highly uniform microstructure. When the implants are used in a human or animal, the calcium phosphate coating degrades uniformly over an extended period of time without releasing particulates. In some embodiments, this is a period of 6 weeks or less. The coatings described herein also have advantageous adhesion and/or cohesion properties such as increased tensile strength compared to prior coatings. Additionally, the calcium phosphate coatings described herein can be rapidly formed on a substrate by a controlled, but rapid, growth process that lends itself to process validation utilizing process diagnostics that allow determination of total coating weight on a batch of parts without having to measure coating weights on parts.

Solution deposited ceramic coatings may be predisposed to cracking during drying. As coating thickness is increased this effect may be exacerbated. In some instances, cracking may be observed for solution deposited hydroxyapatite (SoDHA) coatings as they are dried after being formed. Two exemplary, independent methods to mitigate drying cracks that are described herein include: (1) organic solvent exchange and supercritical solvent extraction, and (2) re-precipitation crack healing via hydrothermal treatment. It is to be understood that organic solvent exchange and re-precipitation crack healing may be performed independent of each other or in combination.

The compositions and methods described herein may improve cementless fixation of orthopedic implants for improved survivorship and expand use of cementless implants to procedures where cemented implants are the current standard of care. One skilled in the art understands that this may allow for reduced operating room time and decreased costs for health care.

Calcium Phosphate Coating

The calcium phosphate coatings may comprise HA or OCP. As used herein, HA includes but is not limited to calcium deficient hydroxyapatite (CDHA). In some embodiments, the HA described herein is non-stoichiometric, such as CDHA. The HA may be of the formula $Ca_{10-x}(PO_4)_{6-x}(HPO_4)_x(OH)_{2-x}$, wherein x is from about 0 to about 2 or about 0.1 to about 2. It is to be understood that the formulas described herein describe stoichiometric equivalents. In some embodiments the HA is of the formula $Ca_{10}(PO_4)_6(OH)_2$. In some embodiments, the OCP is of the formula $Ca_8H_2(PO_4)_6 \cdot 5(H_2O)$. The HA coatings have characteristic molar ratios of calcium to phosphate (Ca/P ratio). The Ca/P ratio may be from about 1 to about 2, about 1.2 to about 2, about 1.3 to about 2, about 1.39 to about 2, about 1 to about 1.8, about 1.2 to about 1.8, about 1.3 to about 1.8, about 1.39 to about 1.8, about 1 to about 1.7, about 1.2 to about 1.7, about 1.3 to about 1.7, about 1.39 to about 1.7, about 1 to about 1.649, about 1.2 to about 1.649, about 1.3 to about 1.649, about 1.39 to about 1.649, or about 1.5 to about 1.67. It is to be understood that coatings of OCP, CDHA, or mixtures thereof may be modified by adjusting calcium and phosphate concentrations and pH in the solutions from which the HA coatings may be formed.

As further described below, the HA and OCP coatings are formable from supersaturated solutions that remain substantially free of turbidity, due to homogenous nucleation in solution, throughout the coating process. In some embodiments, the HA and OCP coatings lack carbonate, which assists with pH control during coating formation. Without intending to be bound by theory, deposition from solutions substantially free of turbidity due to homogenous nucleation is believed to play a role in HA coatings deposited with predictable coating rates and high crystallinity, uniform microstructure, and enhanced biocompatibility. In some embodiments, the wt. % carbonate in the coatings is about 0% to about 25%, about 0% to about 20%, about 0% to about 15%, about 0% to about 10%, about 0% to about 5%, about 0% to about 3%, about 0% to about 2%, about 0% to about 1%, about 0% to about 0.1%, about 0.1% to about 25%, about 0.1% to about 20%, about 0.1% to about 15%, about 0.1% to about 10%, about 0.1% to about 5%, about 0.1% to about 3%, about 0.1% to about 2%, about 0.1% to about 1%, about 1% to about 25%, about 1% to about 20%, about 1% to about 15%, about 1% to about 10%, about 1% to about 5%, about 1% to about 3%, about 1% to about 2%, about 2% to about 25%, about 2% to about 20%, about 2% to about 15%, about 2% to about 10%, about 2% to about 5%, or about 2% to about 3%. In some embodiments, the concentration of carbonate in the coatings is as measured by spectroscopic methods such as IR spectroscopy. The coatings may be substantially carbonate-free. As used herein, "substantially carbonate-free" coatings refers to coatings that do not have a distinguishable carbonate peak between 1500 $cm^{-1}$ and 1300 $cm^{-1}$ when subjected to IR spectroscopy.

The wt % of crystalline HA or OCP in the HA or OCP coatings described herein is about 50% to about 100%, about 60% to about 100%, about 70% to about 100%, about 80% to about 100%, about 90% to about 100%, about 50% to about 99%, about 60% to about 99%, about 70% to about 99%, about 80% to about 99%, about 90% to about 99%, about 50% to about 95%, about 60% to about 95%, about 70% to about 95%, about 80% to about 95%, or about 90% to about 95%. Without intending to be bound by theory, it is believed that the coatings are formed by heterogeneous nucleation, resulting in coatings that primarily comprise crystalline HA or OCP.

The HA component of the HA coatings, or, alternatively, the OCP component of the OCP coatings, has a high crystallinity as measured by, for example, differential scanning calorimetry (DSC). The crystallinity is greater than about 50%, greater than about 80%, greater than about 90%, greater than about 95%, greater than about 96%, greater than about 97%, about 80% to about 99.9%, about 90% to about 99.9%, about 95% to about 99.9%, about 96% to about 99.9%, or about 97% to about 99.9%.

The HA component of the HA coatings or, alternatively, the OCP component of the OCP coatings, has a high crystalline phase purity of its predominant phase. The crystalline phase purity is greater than about 80%, greater than about 90%, greater than about 95%, greater than about 96%, greater than about 97%, about 80% to about 99.9%, about 90% to about 99.9%, about 95% to about 99.9%, about 96% to about 99.9%, or about 97% to about 99.9%. The high crystallinity and high crystalline phase purity of the HA component in the HA coatings enhances biocompatibility and homogenous degradation in vivo while avoiding particulate release. In some embodiments, crystallinity is measured by differential scanning calorimetry (DSC).

The HA component of the HA coatings or, alternatively, the OCP component of the OCP coatings, has low or no amorphous content. The amorphous content is less than about 20%, less than about 15%, less than about 10%, less than about 5%, less than about 4%, less than about 3%, about 0.1% to about 3%, about 0.1% to about 5%, about 0.1% to about 10%, or about 0.1% to about 20%. The amorphous content may be too low to detect. In some embodiments, amorphous content is measured by differential scanning calorimetry (DSC).

The crystal structure of the HA coatings can be characterized using X-ray spectroscopy, such as X-ray powder diffraction spectroscopy. The HA coatings exhibit several characteristic 2θ diffraction angles when characterized by X-ray powder diffraction. The numbers shown in parenthesis are the Miller indices associated with each peak. The X-ray spectra of the HA coatings may exhibit 2θ diffraction angles including about 26±2° (002), about 28±2° (102), about 32±2° (112), about 50±2° (213), and about 53±2° (004) or about 26±0.5° (002), about 28±0.5° (102), about 32±0.5° (112), about 50±0.5° (213), and about 53±0.5° (004). The X-ray spectra of the HA coatings may exhibit 2θ diffraction angles including about 26±1° (002), about 28±1° (102), about 32±1° (112), about 50±1° (213), and about 53±1° (004). The X-ray spectra of the HA coatings may exhibit 2θ diffraction angles including about 25.58±0.1°, about 28.13±0.1°, about 31.75±0.1°, 32.17±0.1°, about 49±0.1°, and about 53±0.1°. It is to be understood that the diffraction angles recited herein may be systematically shifted due to variations in instrumentation.

The XRD spectra of the HA coatings have characteristic relative intensities. As used herein, the relative intensity of a peak in an XRD spectrum refers to the intensity of a peak divided by the intensity of the most intense peak in the spectrum. The peaks associated with the (002), (211), (112), (202), (213), and (004) directions may have relative intensities of 100%, 15.5-16.5%, 27-28%, 50.5-60.5%, 19-20%, 16.5-17.5%, and 14-15%, respectively. Any one of the peaks associated with the (002), (211), (112), (202), (213), and (004) directions may have a relative intensity of 100%, 10-20%, 23-33%, 40-70%, 15-25%, 12-22%, and 10-20%, respectively. In some embodiments, the hydroxyapatite layer has a ratio of XRD intensity ratio of the (002) peak: the (211) peak that is greater than about 1, greater than about 1.25, greater than about 1.5, greater than about 1.75, greater than about 2.0, greater than about 2.5, greater than about 3.0, or greater than about 3.5.

The HA coatings can also be characterized using Fourier transform infrared (FTIR) spectroscopy. The HA coatings exhibit FTIR bands at about 1100 $cm^{-1}$, characteristic of $PO_4^{3-}$. The HA coatings lack FTIR bands characteristic for carbonate between about 1400 to 1500 $cm^{-1}$.

HA coatings of the instant disclosure result in small crystallites sizes as determined by X-ray diffraction or scanning electron microscopy. In some embodiments, the HA coatings are nanocrystalline. The average crystallite size in the [002] direction is from about 60 nm to about 80 nm, about 65 nm to about 75 nm, about 66 nm to about 73 nm, or about 68 nm to about 69 nm. The average crystallite size in the [200] direction is from about 10 nm to about 30 nm, about 15 nm to about 25 nm, about 16 nm to about 23 nm, or about 18 nm to about 22 nm. The average crystallite size in the [210] direction is from about 40 nm to about 60 nm, about 45 nm to about 55 nm, about 46 nm to about 53 nm, or about 48 nm to about 52 nm. In some embodiments, the HA films have a crystallite size in at least one direction that is less than the wavelength of light, and the grains are bonded to one another without the presence of a second amorphous or crystalline phase having a different refractive index. In such embodiments, the films are transparent or translucent.

HA coatings of the instant disclosure are highly porous and have high surface areas. The surface area is about 5 $m^2/g$ to about 100 $m^2/g$, about 10 $m^2/g$ to about 75 $m^2/g$, about 10 $m^2/g$ to about 50 $m^2/g$, about 10 $m^2/g$ to about 200 $m^2/g$, about 10 $m^2/g$ to about 150 $m^2/g$, about 10 $m^2/g$ to about 100 $m^2/g$, about 50 $m^2/g$ to about 200 $m^2/g$, about 50 $m^2/g$ to about 150 $m^2/g$, or about 50 $m^2/g$ to about 100 $m^2/g$. The surface area may be determined using Brunauer-Emmett-Teller (BET) method. This surface area may lead to significant improvements in adsorption of therapeutic agents onto these coatings, as further discussed below. The increased loading capability may be utilized to tailor the dose and prolonged release of the therapeutic agents thereby increasing treatment efficacy.

The coatings described herein release calcium at a substantially continuous rate or at a continuous rate over an extended period of time in vitro as measured by calcium electrodes as described in ASTM F1926. As used herein, a substantially continuous rate is a rate that changes by less than 20% each hour. As used herein, a continuous rate is a rate that changes by less than 5% each hour. The coatings may release calcium at a substantially continuous rate for at least about 5 hours, at least about 10 hours, at least about 15 hours, at least about 20 hours, about 5 hours to about 100 hours, about 5 hours to about 50 hours, about 5 hours to about 30 hours, about 5 hours to about 25 hours, about 10 hours to about 100 hours, about 10 hours to about 50 hours, about 10 hours to about 30 hours, about 10 hours to about 25 hours, about 15 hours to about 100 hours, about 15 hours to about 50 hours, about 15 hours to about 30 hours, or about 15 hours to about 25 hours. The coatings may release calcium at a continuous rate for at least about 5 hours, at least about 10 hours, at least about 15 hours, at least about 20 hours, about 5 hours to about 100 hours, about 5 hours to about 50 hours, about 5 hours to about 30 hours, about 5 hours to about 25 hours, about 10 hours to about 100 hours, about 10 hours to about 50 hours, about 10 hours to about 30 hours, about 10 hours to about 25 hours, about 15 hours to about 100 hours, about 15 hours to about 50 hours, about 15 hours to about 30 hours, or about 15 hours to about 25 hours.

The HA and OCP coatings described herein have high adhesion to a substrate and have high cohesion compared to previously described HA and OCP coatings. Adhesion and cohesion can be quantified by measuring tensile and shear peak stress values. The coatings described herein extend outward from a surface of an orthopedic implant. As used herein, shear stress is the stress component parallel to the bulk direction surface, and tensile stress is the stress component away from the bulk direction surface.

The shear peak stress of the HA or OCP coatings, as determined according to ASTM F1044, is about 10 MPa to about 150 MPa, about 10 MPa to about 100 MPa, about 10 MPa to about 75 MPa, about 10 MPa to about 65 MPa, or about 28.2 MPa to about 63.6 MPa. The tensile peak stress, as determined according to ASTM F1147, is about 25 MPa to about 120 MPa, about 40 MPa to about 120 MPa, about 50 MPa to about 120 MPa, about 60 MPa to about 120 MPa, about 68 MPa to about 120 MPa, 25 MPa to about 100 MPa, about 40 MPa to about 100 MPa, about 50 MPa to about 100 MPa, about 60 MPa to about 100 MPa, about 68 MPa to about 100 MPa, 25 MPa to about 95 MPa, about 40 MPa to about 95 MPa, about 50 MPa to about 95 MPa, about 60 MPa to about 95 MPa, about 68 MPa to about 95 MPa, 25 MPa to about 90 MPa, about 40 MPa to about 90 MPa, about 50 MPa to about 90 MPa, about 60 MPa to about 90 MPa, or about 68 MPa to about 90 MPa.

The HA or OCP coatings may have an average thickness, as measured from the surface of the orthopedic implant to which it adheres, of about 1 µm to about 50 mm, about 1 µm to about 25 µm, about 1 µm to about 20 µm, about 1 µm to about 15 µm, about 1 µm to about 10 µm, about 1 µm to about 8 µm, about 3 µm to about 50 µm, about 3 µm to about 25 µm, about 3 µm to about 20 µm, about 3 µm to about 15 µm, about 3 µm to about 10 µm, about 3 µm to about 8 µm, about 5 µm to about 50 µm, about 5 µm to about 25 µm, about 5 µm to about 20 µm, about 5 µm to about 15 µm, about 5 µm to about 10 µm, about 5 µm to about 8 µm, or about 7 µm.

When applied to porous ingrowth surfaces like porocoat or gription, the HA or OCP coatings may have a weight per unit surface area of about 1 to about 100 mg/cm$^2$, about 1 to about 75 mg/cm$^2$, about 1 to about 50 mg/cm$^2$, about 1 to about 25 mg/cm$^2$, about 1 to about 12 mg/cm$^2$, about 5 to about 100 mg/cm$^2$, about 5 to about 75 mg/cm$^2$, about 5 to about 50 mg/cm$^2$, about 5 to about 25 mg/cm$^2$, about 5 to about 12 mg/cm$^2$, about 7 to about 15 mg/cm$^2$, about 7 to about 14 mg/cm$^2$, about 7 to about 12 mg/cm$^2$, about 9 to about 15 mg/cm$^2$, about 9 to about 14 mg/cm$^2$, about 9 to about 12 mg/cm$^2$, about 9 to about 11 mg/cm$^2$, about 9 to about 12 mg/cm$^2$, or about 8 to about 12 mg/cm$^2$.

When an orthopedic implant coated with the HA or OCP coatings described herein is used in a patient or animal (e.g. canine), the in vivo resorption rates are such that the HA or OCP coating is resorbed within about 3 to about 15 weeks, about 4 to about 15 weeks, about 5 to about 15 weeks, about 6 to about 15 weeks, about 3 to about 14 weeks, about 4 to about 14 weeks, about 5 to about 14 weeks, about 6 to about 14 weeks, about 3 to about 12 weeks, about 4 to about 12 weeks, about 5 to about 12 weeks, about 6 to about 12 weeks, about 1 to about 6 weeks, or less than about 6 weeks.

In some embodiments, the HA or OCP coating further comprises one or more additional therapeutic agents. The coating may be doped with an additional material for improved osteoconduction and/or delivery of anti-infective materials.

The therapeutic agent may include proteins, lipids, (lipo) polysaccharides, growth factors, cytostatic agents, hormones, antibiotics, anti-infective agents, anti-allergenic agents, anti-inflammatory agents, progestational agents, humoral agents, antipyretic agents, and nutritional agents. The therapeutic agent may be an osteoinductive substance, osteoconductive substance, or a substance that is both osteoinductive and osteoconductive.

Metal Surface

The calcium phosphate layers described herein are disposed about a surface of an orthopedic implant. The surface may be a metal surface, such as a titanium or CoCr alloy surface or a titanium dioxide ($TiO_2$) surface. In some embodiments, the outer surface of the metal layer is amorphous and the rest of the metal layer is crystalline. In other embodiments, the entire metal layer is crystalline. For example, the interface between the surface and the calcium phosphate coating may comprise an activated layer from which the calcium phosphate coating nucleates and grows outward. It is to be understood that the entire surface may be coated with HA or the surface may be masked such that a predetermined part of the surface is coated with HA.

The surface may be an activated metal surface. For example, when the metal surface is a titanium surface, the surface may be activated to form a titanate outer surface, which facilitates nucleation and increased adhesion between the titanium surface and the calcium phosphate coating. Activation of the titanium surface also facilitates controlled crystal growth of the calcium phosphate layer therefrom without further heat treatment, as will be further described below. In some embodiments, the native oxide or oxide produced by passivation processes, is converted to titanate by hydroxide treatment. In some embodiments, the titanate is sodium titanate. Alternatively, crystalline $TiO_2$ may be applied to the implant core. Such crystalline films induce HA or OCP nucleation without further treatment. In some embodiments, the implant surface is comprised of something other than titanium alloys. In this case, activation may be accomplished by deposition of nm scale films of crystalline TiOx on the implant surface. Alternatively, thin amorphous TiOx layers may be deposited and converted to titanate by hydroxide treatment of the amorphous film. Additional means of activation include creating surfaces that contain COOH, $NH_2$, or other charged moieties.

In some embodiments, the entire core of the implant is titanium. In other embodiments, titanium is coated on at least part of an implant core, which, in turn, is coated with a calcium phosphate coating described herein. The implant core may comprise a material such as CoCrMo or PEEK.

Alternatively, the implant may comprise any suitable material, such as silicon based materials, ceramic based materials, or polymer based materials. Other contemplated materials include cobalt, chromium, iron, tantalum, niobium, zirconium, and alloys thereof (e.g., titanium alloys and tantalum alloys), as well as cobalt, cobalt-chromium alloys, and stainless steel. The implant may comprise biocompatible polymers, natural or synthetic polymers, such as polyethylene (e.g., ultrahigh molecular weight polyethylene or polyethylene oxide), polypropylene, polytetrafluoroethylene, polyglycolic acid, polylactic acid, other polysaccharides, and copolymers of any of the foregoing (e.g., copolymers of polylactic acid and polyglycol acid), including tissue engineering scaffolds composed of synthetic polymers (e.g. poly HEMA) and biological macromolecules (e.g. collagen and chondroitin sulfate).

The metal or metal oxide layer may have a thickness of at least about 25 nm, at least about 30 nm, at least about 35 nm, at least about 40 nm, at least about 45 nm, at least about 50 nm, at least about 60 nm, at least about 70 nm, at least about 80 nm, at least about 90 nm, or at least about 100 nm. In some embodiments, the layer may have a thickness of about 25 nm to about 125 nm, about 30 nm to about 125 nm, about 35 nm to about 125 nm, about 40 nm to about 125 nm, about 45 nm to about 125 nm, about 50 nm to about 125 nm, about 25 nm to about 100 nm, about 30 nm to about 100 nm, about 35 nm to about 100 nm, about 40 nm to about 100 nm, about 45 nm to about 100 nm, or about 50 nm to about 100 nm Films under 100 nm may cease to display interference colors after hydroxide processing. The preferred thickness of the layer may be determined based on the desired color profile of the orthopedic implant.

The crystal structure of the titanium surface can be characterized using X-ray spectroscopy, such as X-ray powder diffraction. The titanium surfaces exhibit several characteristic 2θ diffraction angles when characterized by X-ray powder diffraction. The X-ray spectra of titanium films exhibit 2θ diffraction angles at about 26°, about 28°, about 32°, about 49°, and about 53°.

The metal surface may be modified prior to being coated with the HA coating. For example, the metal surface may be modified with respect to surface roughness in order to facilitate the adherence of the apatite coating to the biocompatible substrate. Possible methods of modifying the roughness of the metal surface include acid etching or grit blasting.

Titanium Oxide Formation and Activation

As discussed above, a titanium oxide layer may be formed on an orthopedic prosthetic surface. Preferable processes for $TiO_2$ layer formation are conformal (non-line of sight) and produce films that strongly adhere to a core. Atomic layer deposition has been shown to be capable of producing both amorphous and crystalline films that are well adhered and of uniform thickness. Sol-gel processes and electrodeposition of $TiO_2$ films also may be utilized.

After the surface is formed or otherwise available, surface activation may be performed to encourage nucleation and growth of calcium phosphate. Basic conditions may be applied to the titanium oxide surface to activate it. In some embodiments, the titanium surface is treated with a hydroxide source, such as sodium hydroxide. Hydroxide treatment produces a porous titanate surface on the metal that facilitates nucleation and growth of calcium phosphate.

Solution Deposited Hydroxyapatite (SoDHA) Process

The calcium phosphate coatings described herein are formed on the activated surfaces by deposition from supersaturated solutions. At sufficiently optimized supersaturation values, stable nuclei form and grow from active surfaces, resulting in the calcium phosphate coatings described herein. Without intending to be bound by theory, it is believed that the growth predominantly occurs by a heterogeneous nucleation mechanism rather than a homogeneous mechanism under the conditions further described below. The process results in a crystalline calcium phosphate product, such as the coatings described above.

Calcium and phosphate solutions are prepared and adjusted to desired concentrations by dilution. The calcium and phosphate solutions are mixed together, resulting in a solution that is supersaturated with respect to the desired calcium phosphate product. Orthopedic implant precursors, which have activated surfaces, are contacted with the supersaturated solution, resulting in calcium phosphate coating formation at a reproducible rate, under solution conditions that do not result in turbidity. In some embodiments, the substrate has a crystalline $TiO_2$ film surface, which is not necessarily activated. In some embodiments, the substrate has an amorphous film surface that has been treated with a base such as hydroxide. It is contemplated that implants may be masked to allow deposition only on selected portions of the implants.

Solution turbidity may be determined with the aid of optical sensors that evaluate the UV range. An Optek AS16F probe sensor operating at 430 nm was utilized to detect turbidity due to homogenous nucleation in solution. Without intending to be bound by theory, coating at controlled rates is believed to have occurred primarily by heterogenous nucleation.

The degree of supersaturation in the coating solution depends on the activities of Calcium, and Phosphate ions in solution, and solution pH. Activities depend in turn on solution concentration, speciation, and ionic strength. The calcium and phosphate stock solutions are mixed together, resulting in a solution that is supersaturated with respect to the desired calcium phosphate product. Orthopedic implants, which have activated surfaces, are contacted with the supersaturated solution, resulting in calcium phosphate coating formation at a rapid, reproducible rate.

Implants are coated in a solution that is supersaturated with respect to HA and OCP phases. In some embodiments, the supersaturated solution comprises $Ca(NO_3)$, $K_2HPO_4$, $KH_2PO_4$, NaCl, and tris(hydroxymethyl)aminomethane (TRIS) buffer. The ratio of $HPO_4^{2-}/H_2PO_4$ may be selected to achieve the target solution pH. Other counter-ions besides $NO_3$ and K may be utilized as those skilled in the art will appreciate. Calcium and phosphate concentrates may be obtained with a certified concentration and then diluted to working concentrations prior to blending to create the final supersaturated solutions.

The solutions used in forming HA include calcium cations at a concentration of about 0.5 to about 1.5 mM, about 0.6 to about 1.5 mM, about 0.7 to about 1.5 mM, about 0.5 to about 1.3 mM, about 0.6 to about 1.3 mM, about 0.7 to about 1.3 mM, about 0.5 to about 1.1 mM, about 0.6 to about 1.1 mM, about 0.7 to about 1.1 mM, about 0.5 to about 1.05 mM, about 0.6 to about 1.05 mM, about 0.7 to about 1.05 mM, or about 0.62 to about 1.05 mM. In some embodiments the calcium ion is $Ca^{2+}$.

The solutions used in forming HA include phosphate anions at a concentration of about 0.75 mM to about 1.75 mM, about 1.0 mM to about 1.75 mM, about 1.25 mM to about 1.75 mM, about 0.75 mM to about 1.5 mM, about 1.0 mM to about 1.5 mM, about 1.25 mM to about 1.5 mM, about 0.75 mM to about 1.35 mM, about 1.0 mM to about 1.35 mM, about 1.25 mM to about 1.35 mM, about 0.75 mM to about 1.3 mM, about 1.0 mM to about 1.3 mM, or about 1.25 mM to about 1.3 mM. In some embodiments the phosphate ions are $PO_4^{3-}$, $HPO_4^{2-}$, $H_2PO_4^-$, or a combination thereof.

The solutions used in forming HA have a pH of about 7.5 to about 8, about 7.55 to about 8, about 7.6 to about 8, about 7.65 to about 8, about 7.5 to about 7.9, about 7.55 to about 7.9, about 7.6 to about 7.9, about 7.65 to about 7.9, 7.5 to about 7.85, about 7.55 to about 7.85, about 7.6 to about 7.85, about 7.65 to about 7.85, 7.5 to about 7.8, about 7.55 to about 7.8, about 7.6 to about 7.8, about 7.65 to about 7.8, 7.5 to about 7.75, about 7.55 to about 7.75, about 7.6 to about 7.75, about 7.65 to about 7.75, 7.5 to about 7.7, about 7.55 to about 7.7, about 7.6 to about 7.7, about 7.65 to about 7.7, or about 7.684. The pH may be the pH at the beginning of the coating process for a given coating iteration. The pH may be the pH when the solution is at 25° C.

The solutions used in forming OCP include calcium cations at a concentration of about 1.0 to about 2.0 mM, about 1.0 to about 1.9 mM, about 1.0 to about 1.8 mM, about 1.2 to about 2.0 mM, about 1.2 to about 1.9 mM, about 1.2 to about 1.8 mM, about 1.3 to about 2.0 mM, about 1.3 to about 1.9 mM, about 1.3 to about 1.8 mM, about 1.45 to about 2.0 mM, about 1.45 to about 1.9 mM, or about 1.45 to about 1.8 mM.

The solutions used in forming OCP include phosphate anions at a concentration of about 1.5 mM to about 2.6 mM, about 1.5 mM to about 2.4 mM, about 1.5 mM to about 2.25 mM, about 1.7 mM to about 2.6 mM, about 1.7 mM to about 2.4 mM, about 1.7 mM to about 2.25 mM, about 2.0 mM to about 2.6 mM, about 2.0 mM to about 2.4 mM, about 2.0 mM to about 2.25 mM, about 2.2 mM to about 2.6 mM, about 2.2 mM to about 2.4 mM, or about 2.2 mM to about 2.25 mM.

The solutions used in forming OCP have a pH of about 6.75 to about 7.25, about 6.75 to about 7.20, about 6.75 to about 7.15, about 6.75 to about 7.1, about 6.75 to about 7.05, about 6.8 to about 7.25, about 6.8 to about 7.20, about 6.8 to about 7.15, about 6.8 to about 7.1, about 6.8 to about 7.05, about 6.85 to about 7.25, about 6.85 to about 7.20, about 6.85 to about 7.15, about 6.85 to about 7.1, about 6.85 to about 7.05, about 6.9 to about 7.25, about 6.9 to about 7.20, about 6.9 to about 7.15, about 6.9 to about 7.1, about 6.9 to about 7.05, about 6.95 to about 7.25, about 6.95 to about 7.20, about 6.95 to about 7.15, about 6.95 to about 7.1, or about 6.95 to about 7.05. The pH may be the pH at the beginning of the coating process for a given coating iteration.

In some embodiments, a buffer is included in the supersatured solution to stabilize pH. In some embodiments, the buffer is tris(hydroxymethyl)aminomethane (tris) buffer. The concentration of tris is from about 1 mM to about 10 mM, about 2 mM to about 10 mM, about 3 mM to about 10 mM, 1 mM to about 8 mM, about 2 mM to about 8 mM, about 3 mM to about 8 mM, 1 mM to about 6 mM, about 2 mM to about 6 mM, about 3 mM to about 6 mM, or about 5 mM.

A salt may be included in the supersaturated solution to increase ionic strength. In some embodiments, the salt is sodium chloride. The concentration of salt is from about 100 mM to about 200 mM, about 100 mM to about 175 mM, about 100 mM to about 160 mM, 125 mM to about 200 mM, about 125 mM to about 175 mM, about 125 mM to about 160 mM, 140 mM to about 200 mM, about 140 mM to about 175 mM, or about 140 mM to about 160 mM.

The temperature of the solution during the coating process is from about 40° C. to about 50° C., 42° C. to about 50° C., 44° C. to about 50° C., 46° C. to about 50° C., about 40° C. to about 48° C., 42° C. to about 48° C., 44° C. to about 48° C., 46° C. to about 48° C., 46.5° C. to about 47.5° C., or about 47° C. Implants may be maintained at a process temperature within 0.5° C.

HA is a sparingly soluble salt with a $K_{sp}$ on the order of $10^{-120}$, and thus has a very narrow "meta-stable zone" from which controlled heterogeneous nucleation may occur. Surprisingly, a window was found to exist, allowing for relatively stable supersaturated solutions to precipitate crystalline HA onto an activated surface of an orthopedic implant in a controlled manner. In identifying this window, it was observed that low supersaturated concentrations led to slow nucleation rates, while high supersaturated concentrations led to uncontrolled, fast nucleation rates, accretion, and inconsistent growth on the substrate. Without intending to be bound by theory, coating under conditions of excessive supersaturation is believed to occur primarily by homogenous nucleation and accretion.

Various conditions, may lead to increased solution stability. In some embodiments, solutions are mixed at room temperature rather than the temperature at which the deposition process takes place. In some embodiments, calcium stock solutions are added to phosphate stock solutions containing NaCl and tris. In some embodiments, the temperature of stock solutions is not below room temperature.

In some embodiments, the solution is housed in a vessel having smooth walls rather than rough walls.

Surprisingly, it was possible to identify a window of supersaturated solution concentrations or, alternatively, a window of Gibbs free energy, that allowed for controlled HA crystal growth in a desirable timeframe. The solutions used in the SoDHA process were configured such that dG for formation of HA was from about 7 kJ/mol to about 9 kJ/mol, 7 kJ/mol to about 8.8 kJ/mol, 7 kJ/mol to about 8.6 kJ/mol, 7 kJ/mol to about 9.4 kJ/mol, 7 kJ/mol to about 8.2 kJ/mol, 7.2 kJ/mol to about 9 kJ/mol, 7.2 kJ/mol to about 8.8 kJ/mol, 7.2 kJ/mol to about 8.6 kJ/mol, 7.2 kJ/mol to about 9.4 kJ/mol, 7.2 kJ/mol to about 8.2 kJ/mol, 7.4 kJ/mol to about 9 kJ/mol, 7.4 kJ/mol to about 8.8 kJ/mol, 7.4 kJ/mol to about 8.6 kJ/mol, 7.4 kJ/mol to about 9.4 kJ/mol, 7.4 kJ/mol to about 8.2 kJ/mol, 7.6 kJ/mol to about 9 kJ/mol, 7.6 kJ/mol to about 8.8 kJ/mol, 7.6 kJ/mol to about 8.6 kJ/mol, 7.6 kJ/mol to about 9.4 kJ/mol, 7.6 kJ/mol to about 8.2 kJ/mol, 7.8 kJ/mol to about 9 kJ/mol, 7.8 kJ/mol to about 8.8 kJ/mol, 7.8 kJ/mol to about 8.6 kJ/mol, 7.8 kJ/mol to about 9.4 kJ/mol, 7.8 kJ/mol to about 8.2 kJ/mol, about 8.0 kJ/mol to about 8.4 kJ/mol, about 8 kJ/mol, about 8.2 kJ/mol, or about 8.4 kJ/mol.

Surprisingly, it was also possible to identify a window of supersaturated solution concentrations or, alternatively, a window of Gibbs free energy, that allowed for controlled OCP crystal growth in a desirable timeframe. The solutions used in the OCP process were configured such that dG for formation of OCP was from about 2.5 kJ/mol to about 4 kJ/mol, about 2.5 kJ/mol to about 3.7 kJ/mol, about 2.5 kJ/mol to about 3.6 kJ/mol, about 2.5 kJ/mol to about 3.5 kJ/mol, about 2.5 kJ/mol to about 3.45 kJ/mol, about 2.7 kJ/mol to about 4 kJ/mol, about 2.7 kJ/mol to about 3.7 kJ/mol, about 2.7 kJ/mol to about 3.6 kJ/mol, about 2.7 kJ/mol to about 3.5 kJ/mol, about 2.7 kJ/mol to about 3.45 kJ/mol, about 2.9 kJ/mol to about 4 kJ/mol, about 2.9 kJ/mol to about 3.7 kJ/mol, about 2.9 kJ/mol to about 3.6 kJ/mol, about 2.9 kJ/mol to about 3.5 kJ/mol, about 2.9 kJ/mol to about 3.45 kJ/mol, about 3 kJ/mol to about 4 kJ/mol, about 3 kJ/mol to about 3.7 kJ/mol, about 3 kJ/mol to about 3.6 kJ/mol, about 3 kJ/mol to about 3.5 kJ/mol, about 3 kJ/mol to about 3.45 kJ/mol, about 3.1 kJ/mol to about 4 kJ/mol, about 3.1 kJ/mol to about 3.7 kJ/mol, about 3.1 kJ/mol to about 3.6 kJ/mol, about 3.1 kJ/mol to about 3.5 kJ/mol, about 3.1 kJ/mol to about 3.45 kJ/mol, about 3.2 kJ/mol to about 4 kJ/mol, about 3.2 kJ/mol to about 3.7 kJ/mol, about 3.2 kJ/mol to about 3.6 kJ/mol, about 3.2 kJ/mol to about 3.5 kJ/mol, about 3.2 kJ/mol to about 3.45 kJ/mol, or about 3.2 kJ/mol to about 3.45 kJ/mol.

The dG for formation of OCP and HA and the relative supersaturations of the solutions with respect to both HA and OCP for some embodiments of the SoDHA HA process are listed Table 1. These representative values are not limiting as to the possible values associated with the methods disclosed herein.

TABLE 1

Changes in Energy and Supersaturation Values for SoDHA HA Process

| dG HA | dG OCP | SS OCP | SS HA |
|---|---|---|---|
| −8.06451 | −3.11966 | 3.230353 | 20.72261 |
| −8.11148 | −3.14875 | 3.265878 | 21.09168 |
| −8.14687 | −3.16101 | 3.280953 | 21.37415 |
| −8.16934 | −3.18283 | 3.307977 | 21.55537 |
| −8.24149 | −3.25443 | 3.398208 | 22.14794 |

TABLE 1-continued

Changes in Energy and Supersaturation Values for SoDHA HA Process

| dG HA | dG OCP | SS OCP | SS HA |
|---|---|---|---|
| −8.27348 | −3.25519 | 3.399187 | 22.41587 |
| −8.34018 | −3.32947 | 3.495425 | 22.985 |
| −8.34495 | −3.33445 | 3.501971 | 23.0262 |
| −8.34869 | −3.33828 | 3.507014 | 23.05862 |
| −8.3538 | −3.34325 | 3.513581 | 23.10291 |

As further described below, the HA and OCP coatings are formable from supersaturated solutions that remain substantially free of turbidity due to homogenous nucleation in solution throughout the coating process. Without intending to be bound by theory, deposition from solutions substantially free of turbidity due to homogenous nucleation is believed to play a role in HA or OCP coatings deposited with predictable coating rates and having high crystallinity, uniform microstructure, and enhanced biocompatibility.

HA and OCP are very sparingly soluble salts with $K_{sp}$'s on the order of $10^{-120}$ and $10^{-91}$ respectively. As such, HA and OCP have very narrow "metastable zones" from which controlled heterogeneous nucleation and growth can occur. Surprisingly, it was possible to identify windows of supersaturation levels and temperatures that allowed for controlled HA or OCP crystal heterogeneous nucleation and growth in a desirable timeframe. At these supersaturation values, stable nuclei form and grow from active surfaces, resulting in the calcium phosphate coatings described herein.

The SoDHA process additionally comprises agitating the solution when it is in contact with the substrate. Too little agitation during blending of stock solutions may destabilize the solution. High shear agitation during blending of stock solutions may destabilize the solution. Agitation may occur by stirring.

The process may include reducing the amount of air in contact with the supersaturated solution. In some embodiments, the process may be performed under inert atmospheric conditions, such as under an argon or nitrogen atmosphere. The inert atmosphere limits the dissolution of carbon dioxide into the supersaturated solution, which can change the pH without CaP precipitation, interfering with the use of pH as an internal process monitor. Under such conditions, the resulting hydroxyapatite coatings are substantially free of carbonate.

Figure 12:
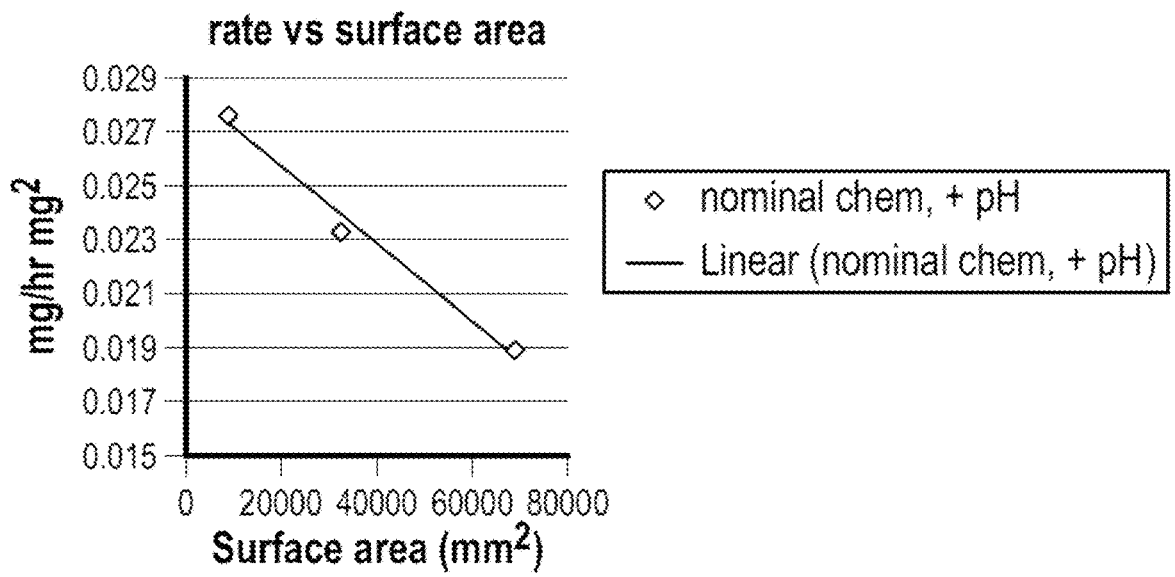
FIG. 12 is a chart showing deposition rates at different surface areas for a solution deposited hydroxyapatite (SoDHA) process.

The process occurs at a controlled, but relatively rapid coating rate. Coating rate can be described in terms of coating mass or coating thickness. For a fixed number of implants in the coating solution, higher coating weights are obtained on implants with high specific surface area like those coated with porous metal in-growth structures. Coating thickness however, is approximately independent of the specific surface area of the implant. Finally, both mass and thickness based coating rates are a function of total surface area/coating solution volume as seen in FIG. 12.

The process deposits HA such that thickness increases at a rate of about a rate of about 0.01 µm/h to about 10 µm/h, about 0.01 µm/h to about 5 µm/h, about 0.01 µm/h to about 4 µm/h, about 0.01 µm/h to about 3 µm/h, about 0.01 µm/h to about 2 µm/h, about 0.01 µm/h to about 1 µm/h, a rate of about 0.1 µm/h to about 10 µm/h, about 0.1 µm/h to about 5 µm/h, about 0.1 µm/h to about 4 µm/h, about 0.1 µm/h to about 3 µm/h, about 0.1 µm/h to about 2 µm/h, about 0.1 µm/h to about 1 µm/h, a rate of about 0.5 µm/h to about 10 µm/h, about 0.5 µm/h to about 5 µm/h, about 0.5 µm/h to about 4 µm/h, about 0.5 µm/h to about 3 µm/h, about 0.5 µm/h to about 2 µm/h, or about 0.5 µm/h to about 1 µm/h.

The process deposits HA on Gription at a rate of about 0.005 mg/hr·mm² to about 0.09 mg/hr·mm², about 0.005 mg/hr·mm² to about 0.025 mg/hr·mm², 0.005 mg/hr·mm² to about 0.0225 mg/hr·mm², 0.005 mg/hr·mm² to about 0.02 mg/hr·mm², 0.005 mg/hr·mm² to about 0.0175 mg/hr·mm², about 0.005 mg/hr·mm² to about 0.015 mg/hr·mm², about 0.0075 mg/hr·mm² to about 0.09 mg/hr·mm², about 0.0075 mg/hr·mm² to about 0.025 mg/hr·mm², 0.0075 mg/hr·mm² to about 0.0225 mg/hr·mm², 0.0075 mg/hr·mm² to about 0.02 mg/hr·mm², 0.0075 mg/hr·mm² to about 0.0175 mg/hr·mm², about 0.0075 mg/hr·mm² to about 0.015 mg/hr·mm², about 0.025 mg/hr·mm² to about 0.09 mg/hr·mm², about 0.01 mg/hr·mm² to about 0.025 mg/hr·mm², 0.01 mg/hr·mm² to about 0.0225 mg/hr·mm², 0.01 mg/hr·mm² to about 0.02 mg/hr·mm², 0.01 mg/hr·mm² to about 0.0175 mg/hr·mm², or about 0.01 mg/hr·mm² to about 0.025 mg/hr·mm².

The coating process may be a "Constant Composition" or "Variable Composition" process.

In a constant composition process, reactants that are consumed by deposition of CaP on implants are semi-continuously added back to the deposition solution throughout the coating process. The addition of reagents is performed based on the drop in pH that corresponds to precipitation of CaP from solution. Thus, the amount of process reagents that are added back to the deposition solution become a surrogate for the amount of HA deposited on the implants. Without intending to be bound by theory, the equations that calculate the composition of the "titrant" (the solutions that are added back to the deposition vessel in response to a change in pH induced by CDHA precipitation) may be:

$$TCaNO3=(Nb)(W_{CaNO3})+(10-x)Ceff$$

$$TP=(Nb)(W_{PO4})+6Ceff$$

$$TNaCl=(Nb)(W_{NaCl})-(20-2x)Ceff$$

$$TKOH=(Nb)(W_{KOH})+(14-2x)Ceff$$

where Ceff is equal to the moles of CaP precipitated per Liter of added titrant and x is the non-stoichiometric coefficient in CDHA, Nb=number of burets adding titrants to solution, and W is the concentration of reactants in the supersaturated solution.

In the variable composition process, chemical driving forces for precipitation are allowed to fall from their initial conditions by an amount that maintains a high range of driving force rather than a constant high driving force as is accomplished by the constant composition process. When the low limit of driving force is reached by depletion of some fraction of coating reagents by precipitation of CaP from solution, the coating solution is discarded and a new coating solution is added to the deposition process vessel. One embodiment of the variable composition process utilizes the quantitative relationship between change in solution pH and the amount and composition of CaP that precipitates from the coating solution. This relationship can be used to determine when to discard coating solutions and replace them with fresh solution as well as to determine the predetermined process endpoint where CaP coating weights have been met. The amount of buffer is selected to lessen the pH reduction that accompanies CaP precipitation while allowing pH to reduce enough to allow the use of pH change as an internal process diagnostic. In some embodiments, the pH measurements may be made intermittently rather than continuously. Coating rates are increased at lower deposition sequence times with greater numbers of coating sequences. In some embodiments, the HA and OCP coating solutions lack carbonate, which may assist with the use of pH as a process monitor or control during coating formation.

Without intending to be bound by theory, the reactions are believed to proceed by the stoichiometry indicated by Table 2.

TABLE 2

Stoichiometry for HA and OCP Processes

| HA | | | OCP | | |
|---|---|---|---|---|---|
| $Ca_{10}$ | $(PO_4)_6$ | $(OH)_2$ | $Ca_8$ | $(HPO_4)_2$ | $(PO_4)_4$ |
|  | $-6\ H_2PO_4$ |  |  | $-2\ HPO_4$ | $-4\ H_2PO_4$ |
|  | $+12\ H$ | $+2\ H$ |  |  | $+8\ H$ |
|  | $+14\ H_2PO_4$ | $-14\ HPO_4$ |  | $-8\ HPO_4$ | $+8\ H_2PO_4$ |
| Totals | $+8\ H_2PO_4$ | $-14\ HPO_4$ |  | $-10\ HPO_4$ | $+4\ H_2PO_4$ |

As shown in Table 2, precipitation of calcium phosphate is accompanied by a drop in calcium and phosphate concentrations, and a decrease in pH. These changes in concentration and pH result in a reduction in degree of supersaturation as the reaction progresses, along with a decrease in deposition rate.

The relationship between pH and amount of precipitate is scalable to different solution volumes. This relationship between change in pH and amount of phase precipitated may be utilized as a process monitor to ensure that a predictable amount of precipitate is formed. The pH of the supersaturated solution may be monitored to determine the extent of coating that has taken place. In some embodiments, the substrate is contacted by the solution until one or more of the calcium concentration, phosphate concentration, and pH decrease to a predetermined level.

Although nucleation rates, growth rates, and relative driving forces for SoDOCP and SoDHA change as calcium phosphate precipitates, a process was developed to minimize changes in these values as precipitation proceeds. The process used for coating the implants was a variable composition process. As used herein, a variable composition process refers to a process that allows for change in thermodynamic variables over the course of the process. In the variable composition process described herein, implants may be coated by multiple batches of solution, allowing ion concentrations and pH to fall only to a predetermined level during each of the iterations. To reduce the extent of concentration changes, multiple sequential depositions were used, with each deposition sequence comprising contacting the orthopedic implant with fresh solution. The pH change associated with deposition may be reduced by buffering the solution with a buffer, such as TRIS buffer.

In some embodiments, three sequential depositions were performed. For a three sequential deposition process, concentration changes during each deposition sequence are reduced by two thirds compared to one deposition sequence. In some embodiments, only one deposition sequence is performed. In some embodiments, 2 or 3 deposition sequences are performed. 1 to 10, 2 to 10, 3 to 10, 1 to 5, 2 to 5, or 3 to 5 deposition sequences may be performed. In some embodiments, the number of deposition sequences employed depends on the ratio of the surface area of the implant to the volume in the coating vessel. Larger implant surface area/volume ratios may correspond with a larger number of shorter coating sequences. Lower surface area/volume ratios may correspond with fewer sequences of longer duration per sequence. The combination of pH buffering and refreshing of solutions minimizes the change in thermodynamic driving forces and may help to ensure that the same calcium phosphate phase is produced throughout the deposition process.

The total contact time with the solution deposition composition in accordance with the inventive method typically is about 30 minutes or more. The total contact time preferably is about 8 hours or less. More preferably, the biocompatible substrate is subjected to multiple sequence contact times of about 1 minute to about 2 hours, about 1 minute to about 1 hour, about 1 minute to about 30 minutes, about 5 minutes to about 2 hours, about 5 minutes to about 1 hour, about 5 minutes to about 30 minutes, about 2 hours or less, about 1 hour or less, or about 30 minutes or less. In general, longer total contact times and shorter coating sequences provide greater thicknesses of the bioactive hydroxyapatite coating. Additionally, the contact time is dependent on the number of bioactive substrates being coated at any one time.

In some embodiments, the relationship between weight of precipitate and change in pH is used to monitor the progression of the SoDHA process. In additional embodiments, the relationship between weight of precipitate and change in calcium and/or phosphate concentration may be used to monitor the progression of the SoDHA process. In other embodiments, the process is performed for a predetermined amount of time and pH, calcium concentration, and phosphate concentration are not monitored.

Similarly, in some embodiments, the relationship between weight of precipitate and change in pH is used to monitor the progression of the SoDOCP process. In additional embodiments, the relationship between weight of precipitate and change in calcium and/or phosphate concentration may be used to monitor the progression of the SoOCP process. In other embodiments, the process is performed for a predetermined amount of time and pH, calcium concentration, and phosphate concentration are not monitored.

In some embodiments, a supercritical fluid may be employed to dry SoDHA coatings. This process includes displacing water from a coating with an organic solvent followed by supercritical fluid extraction. After SoDHA coating formation, organic solvent exchange is performed by immersing coated articles in the organic solvent for a predetermined period of time. After displacement of the organic solvent in the coating, the coated article is placed in a vessel where a supercritical fluid is introduced. Next, the vessel is depressurized to atmosphere while maintaining the temperature above the critical temperature of the supercritical fluid. In this way the supercritical fluid is depressurized directly from a supercritical state to a gas, which avoids creation of liquid capillary forces that may cause cracks.

In some embodiments, the organic solvent is an alcohol. For example, the organic solvent may be methanol, ethanol, or isopropanol. In some embodiments, the supercritical fluid is supercritical $CO_2$ ($scCO_2$).

Additionally, in some embodiments, the SoDHA coatings may be exposed to hydrothermal re-precipitating conditions. After SoDHA coating formation, the coatings may be placed in a phosphate solution and heated. This hydrothermal treatment may be performed at temperatures from about 50° C. to about 350° C., about 60° C. to about 350° C., about 70° C. to about 350° C., about 80° C. to about 350° C., about 50° C. to about 150° C., about 60° C. to about 150° C., about 70° C. to about 150° C., about 80° C. to about 150° C., about 50°

C. to about 99° C., about 60° C. to about 99° C., about 70° C. to about 99° C., about 80° C. to about 99° C., about 50° C. to about 95° C., about 60° C. to about 95° C., about 70° C. to about 95° C., about 80° C. to about 95° C., about 50° C. to about 90° C., about 60° C. to about 90° C., about 70° C. to about 90° C., about 80° C. to about 90° C., about 50° C. to about 85° C., about 60° C. to about 85° C., about 70° C. to about 85° C., about 80° C. to about 85° C., about 50° C. to about 80° C., about 60° C. to about 80° C., or about 70° C. to about 80° C. The coatings may be heated for times from about 15 minutes to about 24 hours, about 15 minutes to about 4 hours, about 15 minutes to about 3 hours, about 15 minutes to about 2 hours, about 30 minutes to about 24 hours, about 30 minutes to about 4 hours, about 30 minutes to about 3 hours, about 30 minutes to about 2 hours, about 1 hour to about 24 hours, about 1 hour to about 4 hours, about 1 hour to about 3 hours, about 1 hour to about 2 hours, or about 2 hours.

The methods described herein maximize the amount of material that grows on the substrate, and minimize the amount that accretes onto the surface from material homogeneously precipitated in suspension. Additionally, these methods provide for a controlled, predictable deposition rate, produce films with high adhesion and cohesion, and produce a uniform microstructure that degrades uniformly without release of particulates. Predictable deposition rates allow targeted film thicknesses to be readily achieved. The methods also provide suitable coverage of porous structures and are suitable for various implant geometries.

Definitions

As used herein, relative supersaturation of a product (S) is defined by the following equation: $S=[IAP/K_{sp}]^{1/v}$, where IAP is the ionic activity of the product, $K_{sp}$ is the solubility constant of the product, and v is the number of ions in the unit formula of the product.

As used herein, Gibbs free energy change (dG) associated with a phase change is defined by the following equation: $dG=RT/v*\ln[IAP/K_{sp}]$, where R is the universal gas constant, T is absolute temperature, IAP is the ionic activity of the product, $K_{sp}$ is the solubility constant of the product, and v is the number of ions in the unit formula of the product.

As used herein, relative supersaturation S, is equal to $(IAP/Ksp)^{1/v}$.

As used herein, homogenous precipitation or homogenous nucleation refers to nucleation of a solid phase from a supersaturated solution that does not involve a foreign surface, resulting in a turbid supersaturated coating solution.

As used herein, heterogeneous precipitation or heterogeneous nucleation refers to nucleation of a solid phase on an impurity phase from a supersaturated solution that is substantially free of turbidity during the deposition process.

As used herein, "octacalcium phosphate" or "OCP" refers to a calcium phosphate having the formula $Ca_8(HPO_4)_2(PO_4)_4$.

As used herein, supersaturated refers to a solution in which a solute is concentrated beyond equilibrium. When concentration is above the saturation point, the solution is said to be supersaturated.

As used herein, in vitro, in reference to dissolution studies, means in a tris buffered saline solution at pH 7.4, as described in ASTM F1926.

EXAMPLE 1

Activation of CoCr by Atomic Layer Deposition of TiO₂ Films

TiO₂ films were prepared on CoCr grit blast surfaces by Beneq (Helsinki, Finland) by atomic layer deposition. The films were produced from TiCl₄ and H₂O precursors. Amorphous films were produced at 90° C. and crystalline (Anatase plus Rutile) films were produced at 200° C. Films were activated with hydroxide, according to the methods described in Example 3 (4 hrs, 5M NaOH, 60° C.). 500, 200, 100, and 50 nm amorphous films (500 A, 200 A, 100 A, and 50 A) and 500 and 200 nm crystalline films (500° C., 200° C.) were evaluated for their ability to form hydroxyapatite coatings according to the SoDHA method using nominal concentrations, as further described in Examples 5 and 6.

HA coating weight for the samples ranged from about 6 mg to about 8 mg, as shown in FIG. 1. Both amorphous and crystalline films were able to nucleate HA after activation by strong base. Coating experiments showed that deposition occurred for as deposited crystalline titanium oxide, but at lower rates than observed for NaOH etched amorphous or crystalline titanium oxide.

Figure 2:
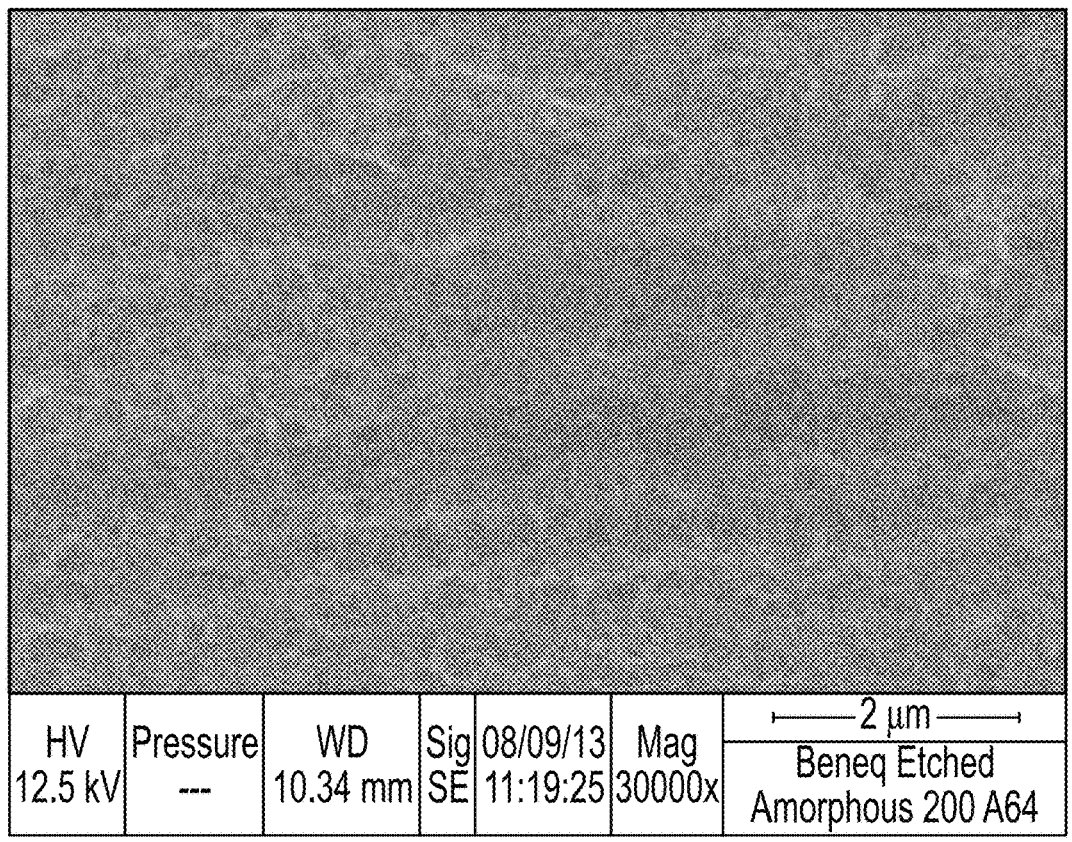
FIG. 2 is a scanning electron microscopy (SEM) image of a 200 nm-thick amorphous TiO$_2$ coating after treatment with hydroxide.
Figure 3:
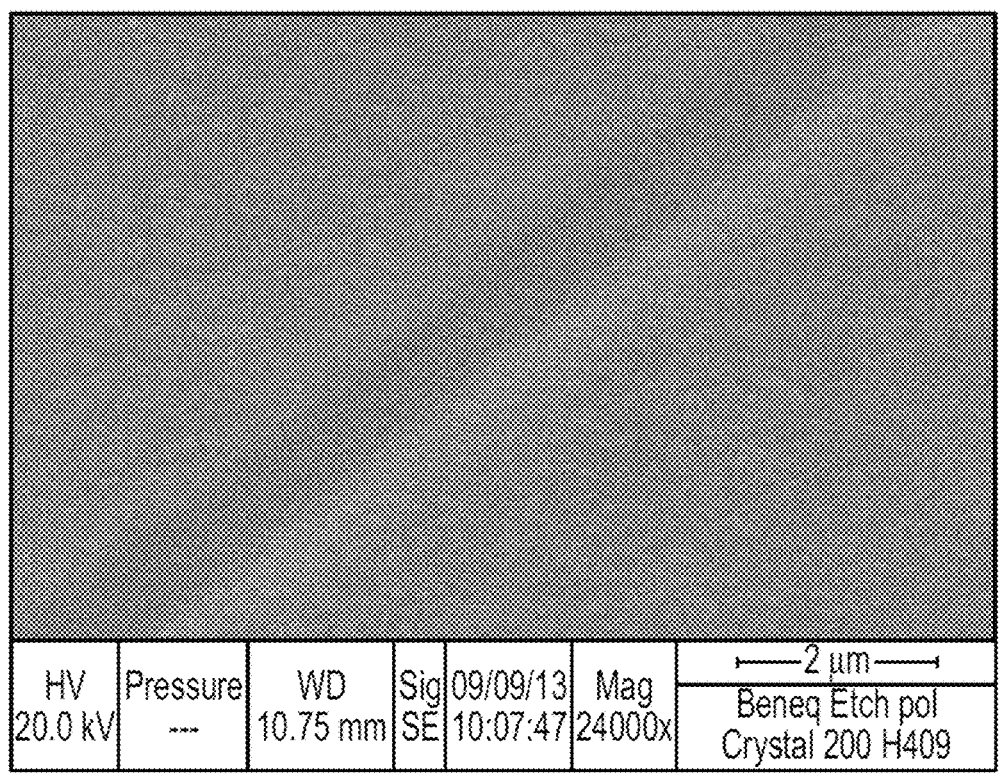
FIG. 3 is an SEM image of a 200 nm-thick crystalline TiO$_2$ coating that was not treated with hydroxide.

A scanning electron microscopy (SEM) image of the 200 nm-thick, activated amorphous film, prior to HA coating is shown in FIG. 2. An SEM image of the 200 nm-thick, activated crystalline film, prior to HA coating is shown in FIG. 3. The characteristic titanate topography was apparent on amorphous films. Films prepared over 100 nm thick showed interference colors after hydroxide treatment.

Figure 4:
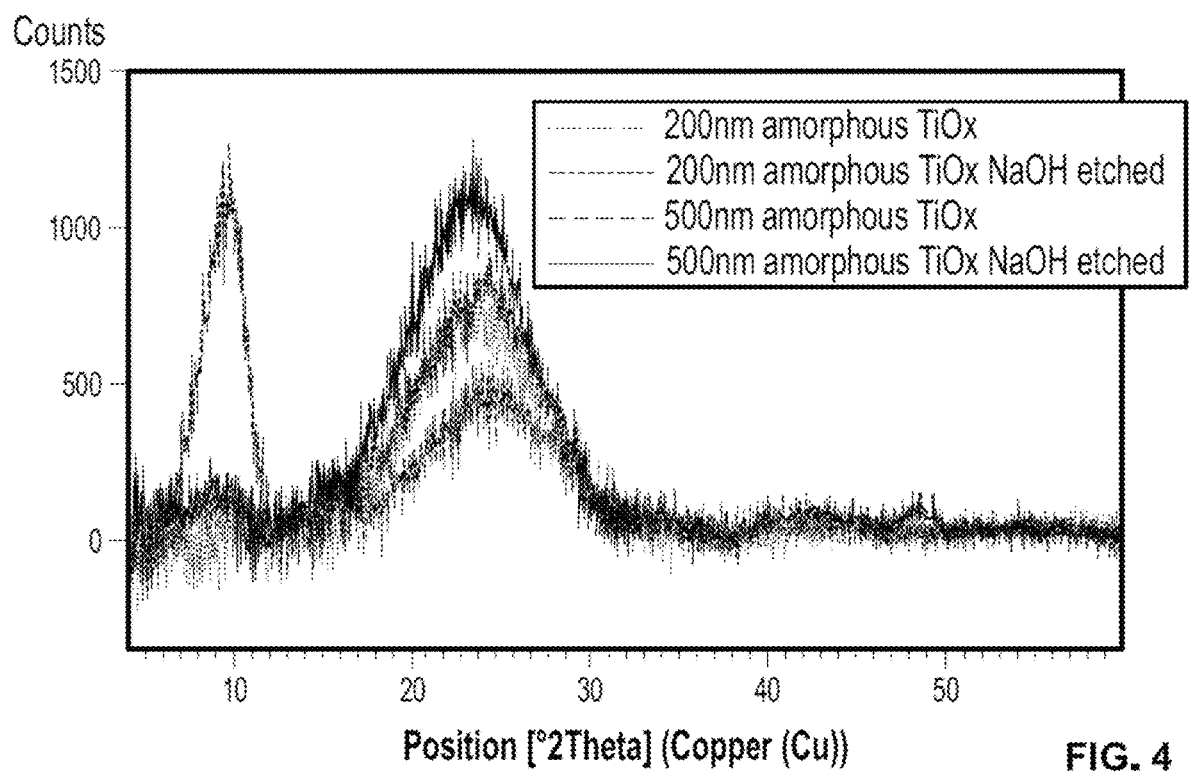
FIG. 4 is a grazing angle X-ray diffraction (XRD) spectrum overlay, showing spectra for 200 nm-thick amorphous TiO$_2$ coatings, with and without hydroxide treatment, and 500 nm-thick amorphous TiO$_2$ coatings, with and without hydroxide treatment.
Figure 5:
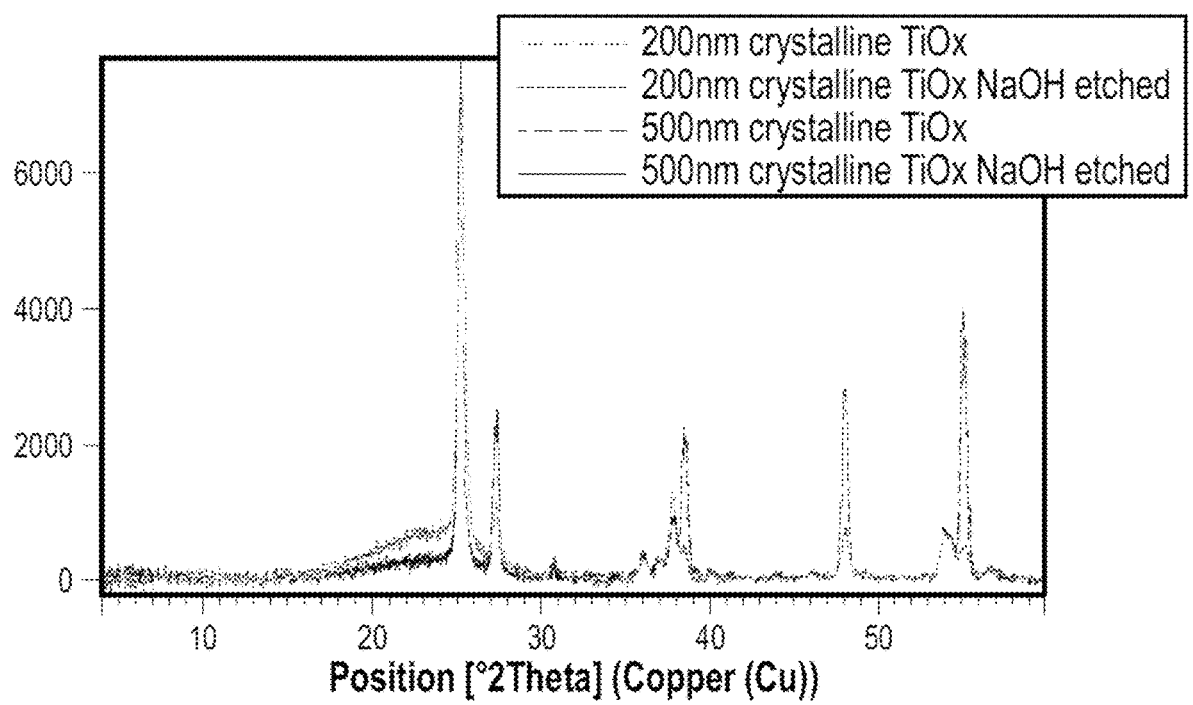
FIG. 5 is a grazing angle XRD spectrum overlay, showing spectra for 200 nm-thick crystalline TiO$_2$ coatings, with and without hydroxide treatment, and 500 nm-thick crystalline TiO$_2$ coatings, with and without hydroxide treatment.

Grazing angle X-ray diffraction (XRD) spectra were obtained for amorphous and crystalline titanium coatings at 200 nm-thick and 500 nm-thick before and after activation with NaOH. The XRD spectra for the amorphous films are shown in FIG. 4. The XRD spectra for the crystalline films are shown in FIG. 5.

EXAMPLE 2

Electrolytic Formation of TiO₂ Films on CoCr Alloy

An electrolyte solution of 0.05 M TiCl₄ and 0.25 M H₂O₂ in a mixed methanol/water (3/1 vol %) solvent was prepared. The pH of the solution was fixed between 0.9 and 1.0. All chemicals were ACS grade. To prepare the electrolyte solution, TiCl₄ was slowly added to the solvent, followed by H₂O₂. During the addition of H₂O₂, an immediate color change from transparent to dark orange was observed, indicating the formation of a peroxo-complex. Electrolytes were stored at about 4° C. after preparation and pH measurement and, if necessary, pH adjustment. Electrodeposition was performed galvanostatically up to the desired charge density. The temperature was fixed by a cryostat to 0° C. A homemade Labview program (controlling a Xantrex XDC 300-20 power source) was built to control current charge density while recording voltage-time curves. The applied charge density was fixed in the range form 2.5 C/cm² to 40 C C/cm². The current density was varied between −50 mA/cm² to −50 mA/cm².

Figure 6:
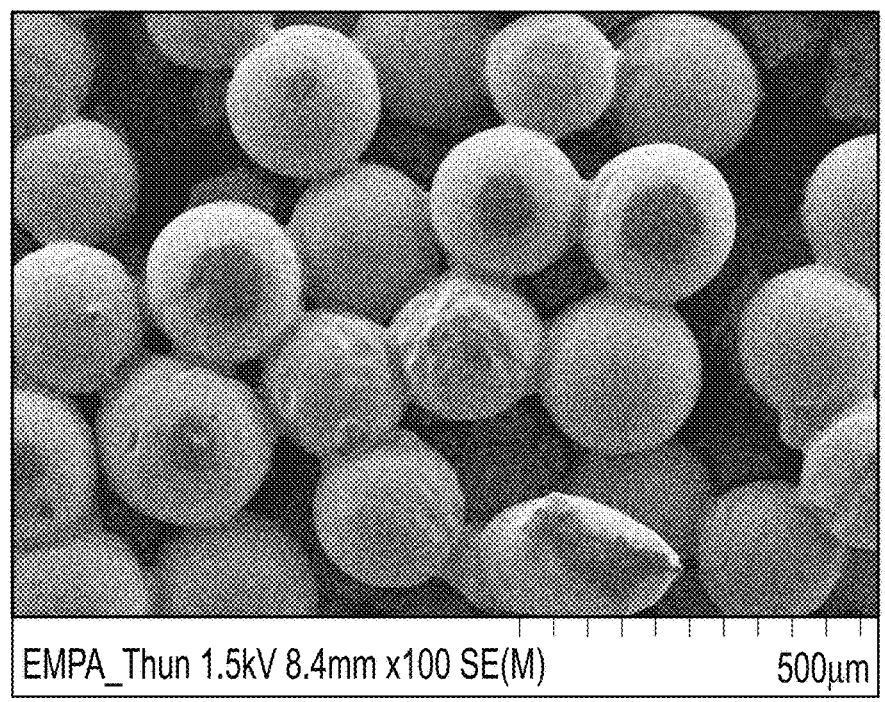
FIG. 6 is an SEM image of a titanium layer that has been electrodeposited onto a CoCrMo core.

Good film uniformity was obtained in 0.05 M TiCl₄, 0.5 M H₂O₂ in a mixed methanol/water (3:1 vol. %) solvent (pH=0.97). Good growth occurred at −1.1 V for 1 hour at 60° C. FIG. 6 is an SEM image showing a titanium coating electrodeposited under these conditions on a CoCrMo substrate.

EXAMPLE 3

Titanium Surface Activation 1 inch diameter Ti6-4 disks coated with DePuy Gription porous metal coating were cleaned and activated by the following steps. Disks were set in a container with reverse osmosis (RO) water and alkaline detergent for 15 min with a sonicator 2 times. Next, disks were set in a container with only RO water for 15 minutes with a sonicator 2 times. 4 disks were placed in a 500 mL beaker and 200 mL of 5M NaOH was added. The disks were placed in secondary containment and a loose cap was set over the top of the beaker. The temperature of the beaker was set to 60° C. and held for 4 hrs. The desks were removed from the beaker and rinsed in RO water in a sonicator for 15 minutes 4 times. Disks were left in a 60° C. oven overnight to dry. No effect of heat treatment of this activation layer on the tendency to promote nucleation and growth of CaP coatings was found in the methods disclosed herein, and examples reported below were performed without heat treatment of the activated surface. Coating experiments showed that deposition occurred for crystalline titanium, but at lower rates than observed for NaOH etched amorphous titanium.

EXAMPLE 4

Stock Solution Preparation

Concentrate and stock solutions for HA coating of 1 inch diameter disks in a 1 L vessel were prepared by the following steps.

A 36 mM Ca solution was prepared. A clean 2-liter bottle was obtained and a magnetic stir bar was placed in the bottle. 8.50194 g of $Ca(NO_3)$ was weighed out and poured into the 2-liter bottle. The bottle was purged with Argon for 3-5 minutes. 1000 mls of deionized (DI) water with a resistivity of 18 MΩ or higher was added to the bottle. The bottle was placed on stir plate and its contents were stirred until $Ca(NO_3)$ was fully dissolved. The solution was filtered using a 0.22 μm cell culture vacuum filter (Corning, Funnel Volume, 1000 mL; Receiver: 90 mm; Pore Size: 0.22 um; PES, No.: 431098).

A 40 mM phosphate ($P_i$) solution was prepared. A clean 2-liter bottle was obtained and a magnetic stir bar was placed in the bottle. 5.444 g of $KH_2PO_4$ was weighed out and poured into the 2-liter bottle. 19.0387 g of Tris and 273.675 g NaCl were weighed out and added to the bottle. The bottle was purged with Argon for 3-5 minutes. 898.1 mL of 18 MΩ or higher DI water was added. Using a manual pipette, 5.8 mL of 6N HCl was added to the bottle. The bottle was placed on a stir plate and stirred until the Tris, NaCl, and $KH_2PO_4$ were fully dissolved. The final volume of the solution was 1 L and the pH of the solution was approximately 8.23 at 25° C. If necessary, pH may be adjusted to this value using HCl or NaOH. The solution was filtered using a 0.22 um cell culture vacuum filter (Corning, Funnel Volume, 1000 mL; Receiver: 90 mm; Pore Size: 0.22 um; PES, No.: 431098).

495.3 mls of a 2.0787 mM Ca stock solution was prepared. The previously prepared 36 mM calcium solution was placed on a stir plate and stirred for five minutes. A clean 1-liter bottle was purged with Argon. 28.6 mL of 36 mM calcium solution was added using a pipette. 466.7 mL of 18 MΩ or higher DI water was added.

500 mL of 2.5690 mM $P_i$ stock solution was prepared. The previously prepared 40 mM phosphate solution was placed on stir plate for five minutes. A clean 1-liter bottle was purged with Argon. 32.112 mL of 40 mM phosphate solution was added using a pipette. 467.888 mL of 18 MΩ or higher DI water was added.

A 1.7792 mM Ca solution was prepared. The previously prepared 36 mM calcium solution was placed on a stir plate and stirred for five minutes. A clean 1-liter bottle was purged with Argon. 36 mM calcium solution and 18 MΩ DI water were mixed to achieve the desired concentration.

A 2.2262 mM 500 mL $P_i$ solution was prepared. The previously prepared 40 mM phosphate solution was placed on stir plate for five minutes. A clean 1-liter bottle was purged with Argon. 40 mM phosphate solution and 18 MΩ DI water were mixed to achieve the desired concentration.

EXAMPLE 5

HA Coating by Solution Deposition in 1 L Vessel 1 inch diameter porous metal coated titanium coupons were coated. A cover for a 1 L jacketed vessel was provided to allow for an Ar cover gas during process the deposition process. 500 mLs of 2.569 mM phosphate stock solution prepared according to Example 4 was added into the 1 L jacketed vessel, and the vessel was placed on a stir bar plate. The stir bar was turned on at 200 rpm. Next, 495.3 mL of 2.0787 mM Ca stock solution, prepared according to Example 4 was poured into the vessel. Total volume at 25° C. was 1 L due to volume expansion associated with NaCl dilution. pH of the solution was 7.68 and the calculated dG (OCP) was approximately 3.25 and dG (HA) was approximately 8.24. Relative SS for OCP and HA were about 3.3 and 22.5 respectively at the initiation of the coating process. A heated water bath was circulated through the jacketed vessel, and the solution was allowed to reach 47° C. The temperature was controlled within 0.5° C. Temperature sensors were calibrated to a NIST traceable RTD. The etched (activated) disks were placed in fixtures that allowed disks to be suspended in the 1 L jacketed vessel. After coating, the disks were moved into a first container of DI water and allowed to soak for 1 minute. Next, the disks were moved from the first container to a second container of DI water and allowed to soak for 1 minute. Then, disks were moved from the second container to a third container of DI water and allowed to soak for 1 minute. After soaking, the disks were moved to a 6-well tray and placed in a 60° C. oven to dry for 60 min.

EXAMPLE 6

Full Scale Process Validation

Figure 7:
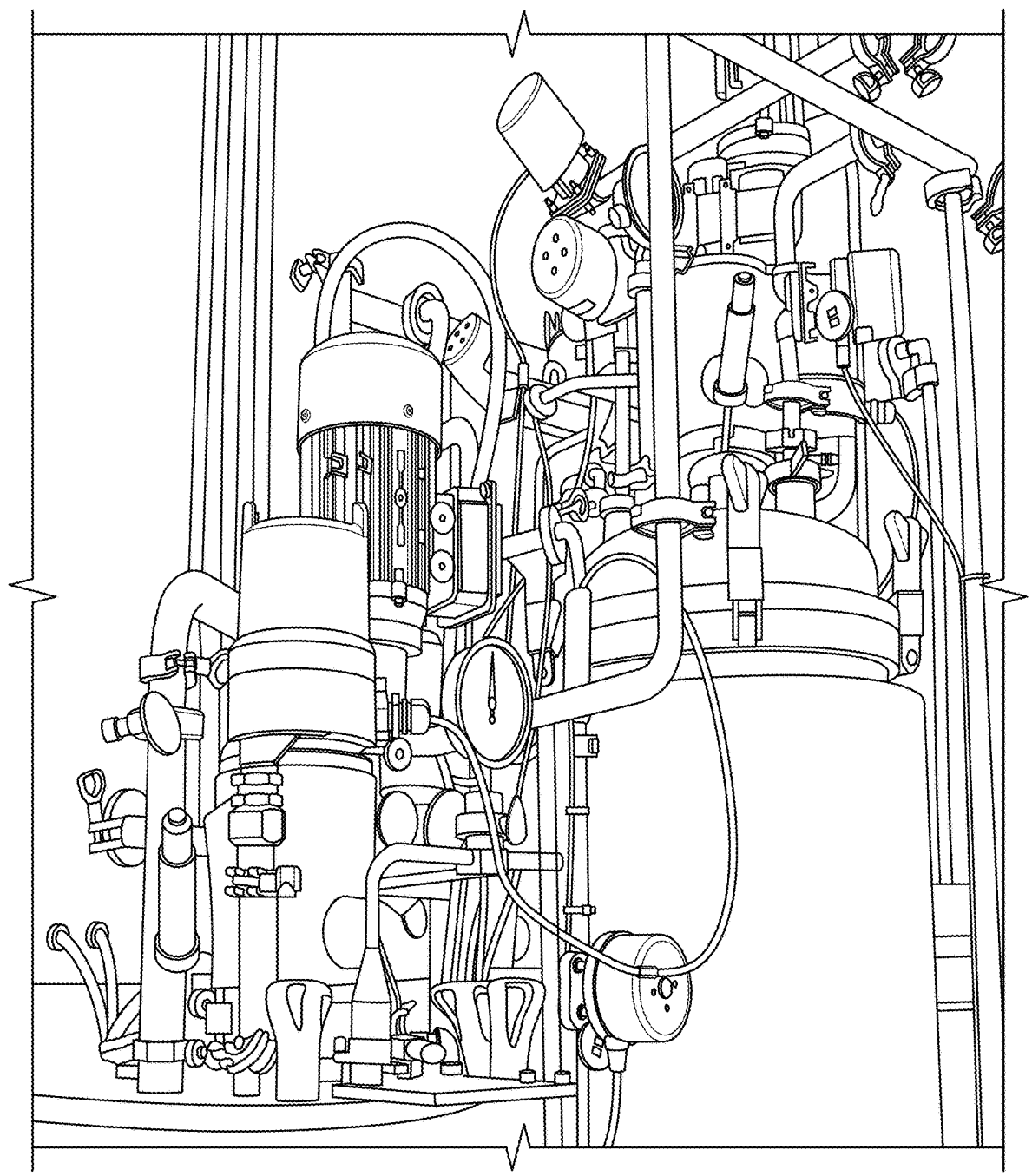
FIG. 7 is an image of a full scale coating vessel.

The nominal process described in Example 5 was repeated using a "full scale" system shown in FIG. 7. The full scale system is designed to coat up to 40 acetabular cups or 16 hip stems in a single coating run of one or more coating sequences. A series of coating runs were made utilizing both standard DePuy TriLock BPS hip stems or hip stems modified to accept one-inch diameter coupons (shown in FIG. 19) were made at nominal as well as + and − process limits. Process limits were defined as + and −2% of Ca and Phosphate concentrations and +−0.06 pH units. Coatings were characterized by various methods as described in the examples.

EXAMPLE 7

OCP Coating by Solution Deposition

The 1 L process described in Example 5 was repeated, except for the following modifications. A 1.7779 mM Ca solution was used instead of the 1.0284 mM Ca solution, and a 2.2262 mM $P_i$ solution was used instead of the 1.2730 mM $P_i$ solution. The pH of the $P_i$ solution was such that after combining the Ca and P$_i$ solutions, the resulting solution had a pH of 7.000. The coating process was repeated using different total deposition times to generate the experimental coating weights shown in FIG. 11. Samples were characterized by XRD as described in Example 11.

EXAMPLE 8

Figure 11:
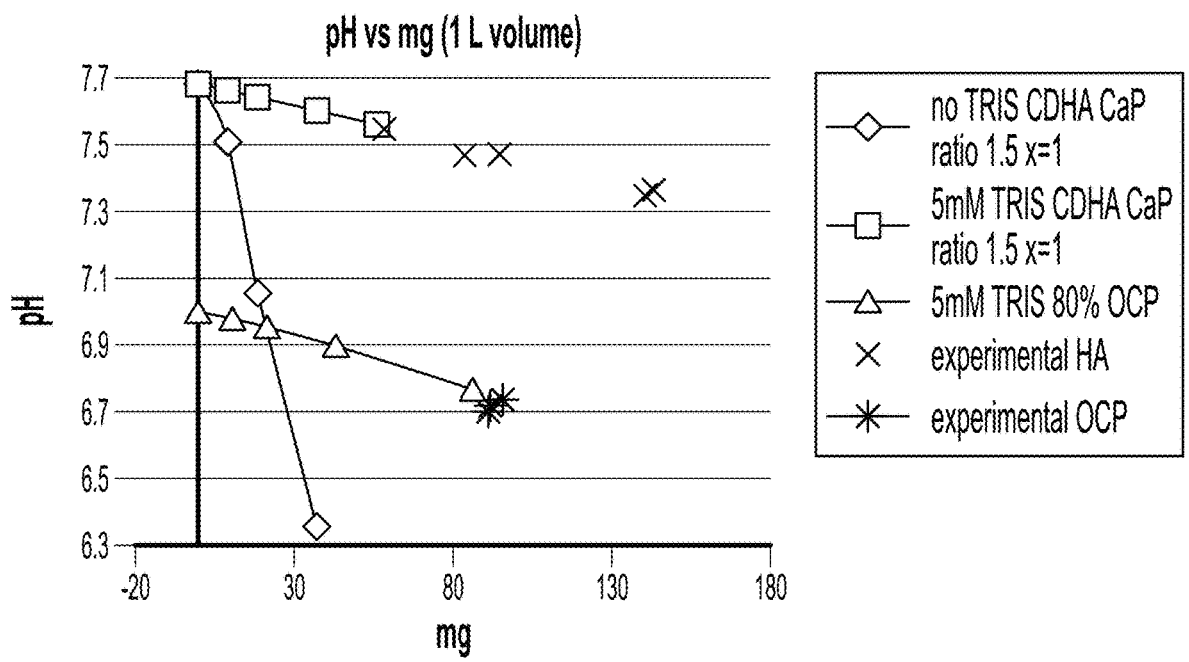
FIG. 11 is a chart showing a relationship between pH and the weight of hydroxyapatite precipitate and octacalcium phosphate (OCP) precipitate over the course of their respective deposition processes.

Use of dpH as a Process Monitor pH and precipitate mass were monitored for the SoDHA process described in Example 5 at nominal values, the SoDHA process described in Example 5 at nominal values without tris, the SoDHA process described in Example 5 at nominal values with 5 mM, the OCP process described in Example 7, and the OCP process described in Example 7 with 5 mM tris. The relationship between pH and amount of precipitate is scalable to different solution volumes and buffer strengths using a solution thermodynamics software such as "Chemist" version 1.0.3 from Micromath Scientific Software, 9202 Litzsinger Road Saint Louis, Mo. 63144. This relationship between change in pH and amount of phase precipitated may be utilized as a process monitor to verify that a targeted amount of precipitate is formed. A spreadsheet calculator was constructed based on the relationships summarized in Table 2 to calculate the concentrations and activities of reactants as a function of amount of CaP phase precipitated. CaP phases that can be modeled by this calculator include stoichiometric HA, stoichiometric OCP, non-stoichiometric CDHA, and mixtures of HA or CDHA with OCP. For each increment of CaP phase precipitated, the reduced reactant concentrations were input into Chemist, which calculates the system pH based on buffer type and levels being analyzed. FIG. 11 shows predicted vs experimental plots of pH as a function of total mg precipitated of CaP comprised of:

1) CDHA of formula $Ca_{10-x}(PO_4)_{6-x}(HPO_4)_x(OH)_{2-x}$ with x=to 1.0
   a) without TRIS buffer
   b) with 5 mM TRIS buffer
2) A mixture of 80% OCP and 20% CDHA with x=1.5 with 5 mM TRIS.

Experimental values in this plot are taken from samples prepared according to Examples 5 and 7.

EXAMPLE 9

Characterization of HA Coating

Figure 8:
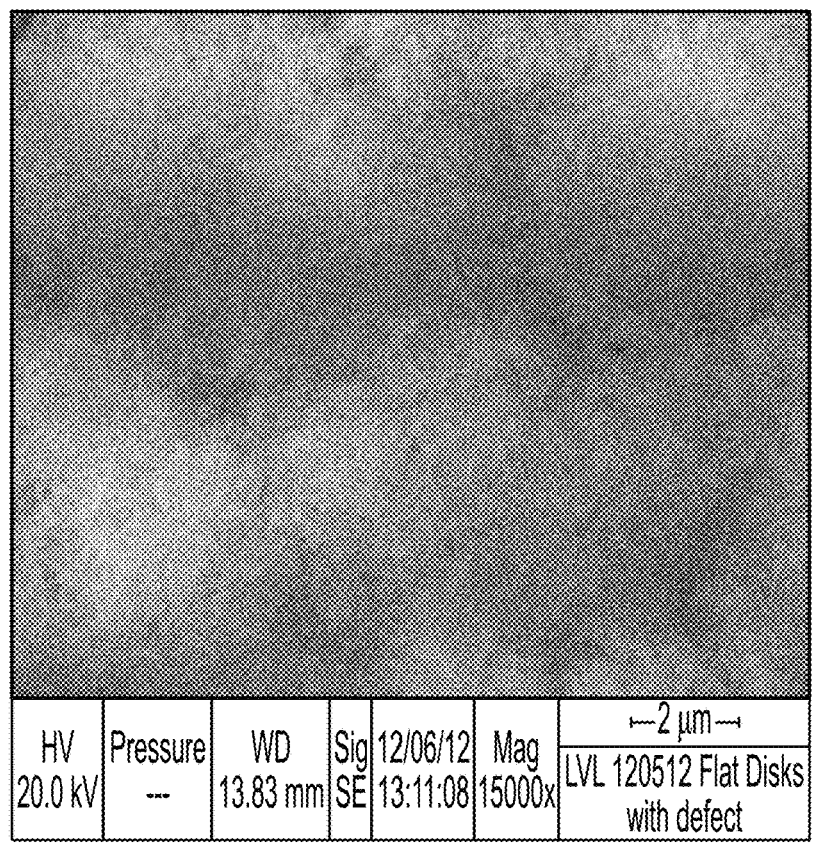
FIG. 8 is an SEM image of a SoDHA coating at 15000× magnification.
Figure 9:
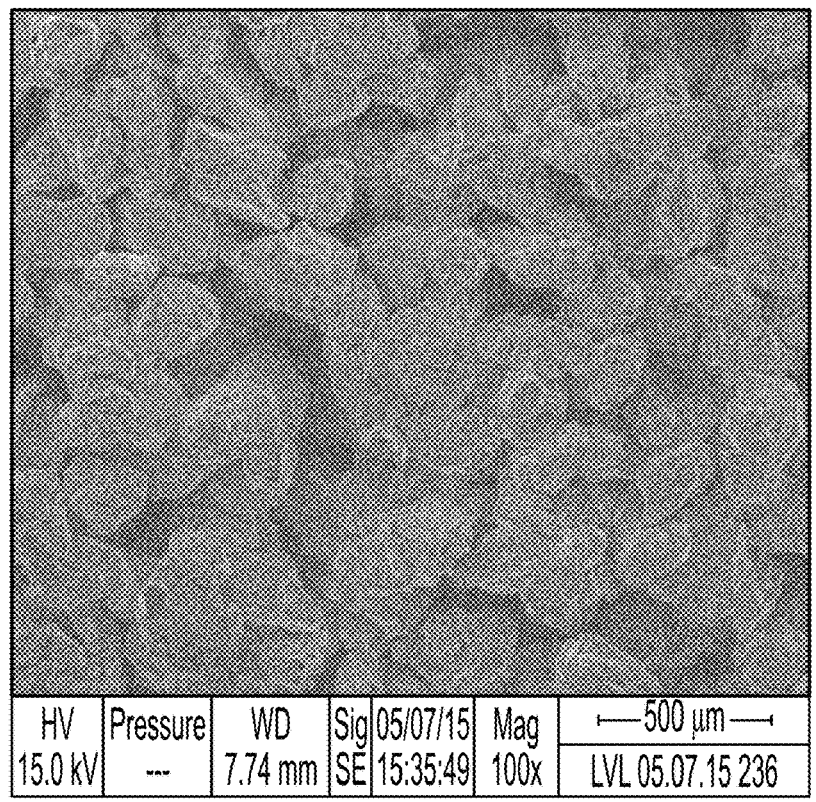
FIG. 9 is an SEM image of a SoDHA coating at 100× magnification.
Figure 10:
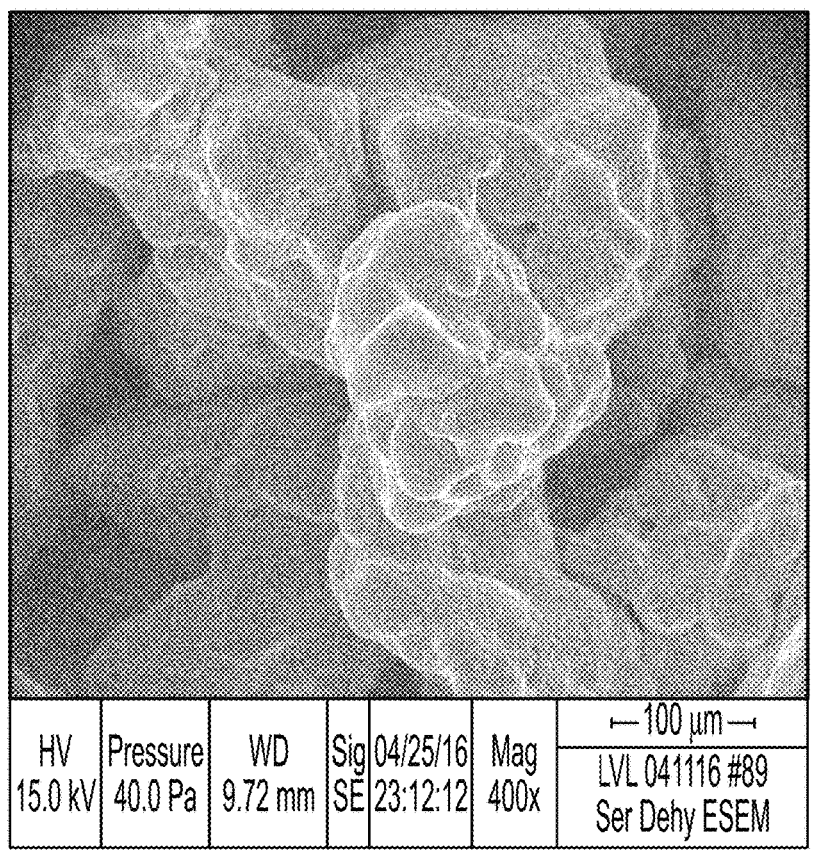
FIG. 10 is an SEM image of a SoDHA coating at 400× magnification.

FIG. 8 shows a scanning electron microscope (SEM) image of SoDHA HA coated flat titanium disc at 15000× magnification. FIGS. 9 and 10 show scanning electron microscope (SEM) images of a SoDHA HA coated porous ingrowth structure (Gription) at 100× and 400× magnification, respectively. It is seen the HA coating was continuous over the disc surface.

FIG. 12 shows the effect of substrates having various surface area (mm$^2$) on deposition rate (mg/hr) at fixed dG, temperature, and degree of agitation. Materials were coated with HA at nominal values in the full scale deposition system, using nominal conditions as described in Example 5. It can be seen that coating rate decreased as surface area increased. This trend may be utilized to estimate coating time based on surface area for a given substrate.

The density of bulk HA and OCP are similar at about 3.1 g/cm$^3$. Deposits of HA prepared at nominal values according to Example 5 weighed 7 mgs on flat coupons, had a surface area of 5.07 cm$^2$, and had a thickness of about 7 microns, corresponding to an actual density of about 1.97 g/cm$^3$ and a porosity of about 36%.

Figure 13:
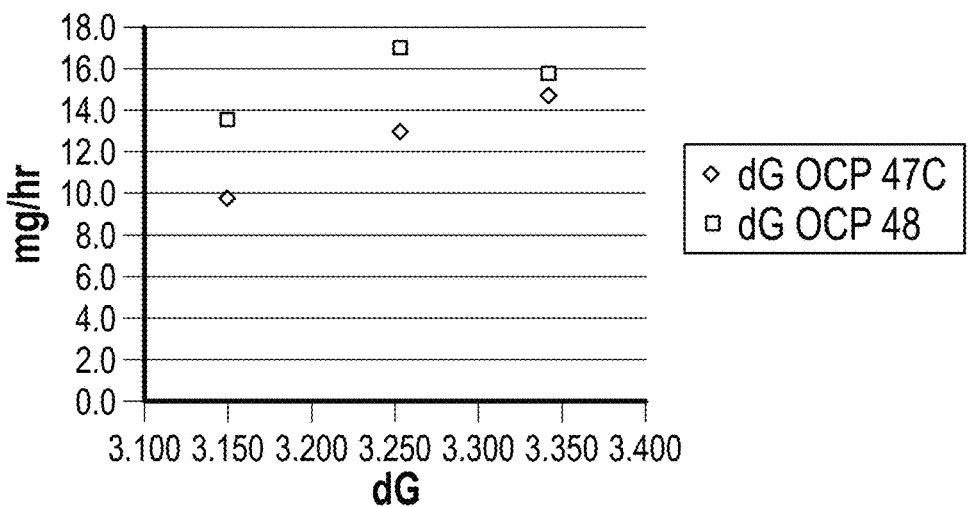
FIG. 13 is a chart showing a relationship between coating rate and the change in free energy associated with deposition for OCP films formed at 47° C. and 48° C.

FIG. 13 is a plot showing coating rate at various initial dG values for the formation of OCP films according to Example 7. It can be seen that a correlation between dG and coating rate was increased at 47° C. compared to 48° C. Without intending to be bound by theory, this trend is believed to be a consequence of deposition rates declining at high dG values due to precipitation in solution rather than on the implant.

EXAMPLE 10

Full Scale Process Characterization

The coating prepared according to the full scale system process of Example 5 at nominal and process limit values met the following specifications:

Coating weight: 0.08 to 0.12 mg/mm$^2$ of projected surface area
% crystalline HA by Rietveld analysis: >70%
% of amorphous calcium phosphate: <detection limit by DSC, as described in Example 14.
XRD crystallite size parameters:
1/β (200) 1.63+−0.13
1/β (002) 4.15+−0.10
1/β (210) 1.5+−0.10
Tensile adhesion as determined according to ASTM F1147 (measured on grit blasted flat): >68 MPa Ca/P ratio: 1.39 to 1.65

FIGS. 14-18 summarize data obtained from the full scale system evaluated at nominal and process limit conditions. In all cases, the error bars are equal to 3 standard deviations of the data.

Figure 14:
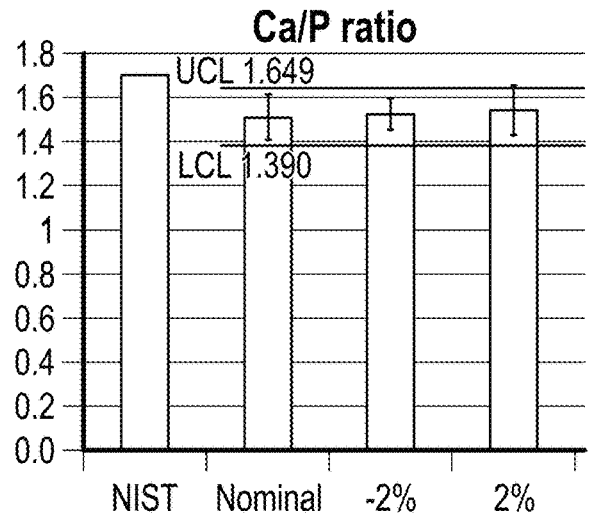
FIG. 14 is a chart showing the Ca/P ratios of five samples created according to the SoDHA process in the full scale deposition system shown in FIG. 7.

FIG. 14 shows the Ca/P ratio for HA coated materials prepared by deposition in the full scale system according to Example 6 at nominal and process limits. Ca/P ratio was determined by wet chemical methods. "NIST" refers to National Institute of Standards and Technology standard hydroxyapatite.

Figure 15:
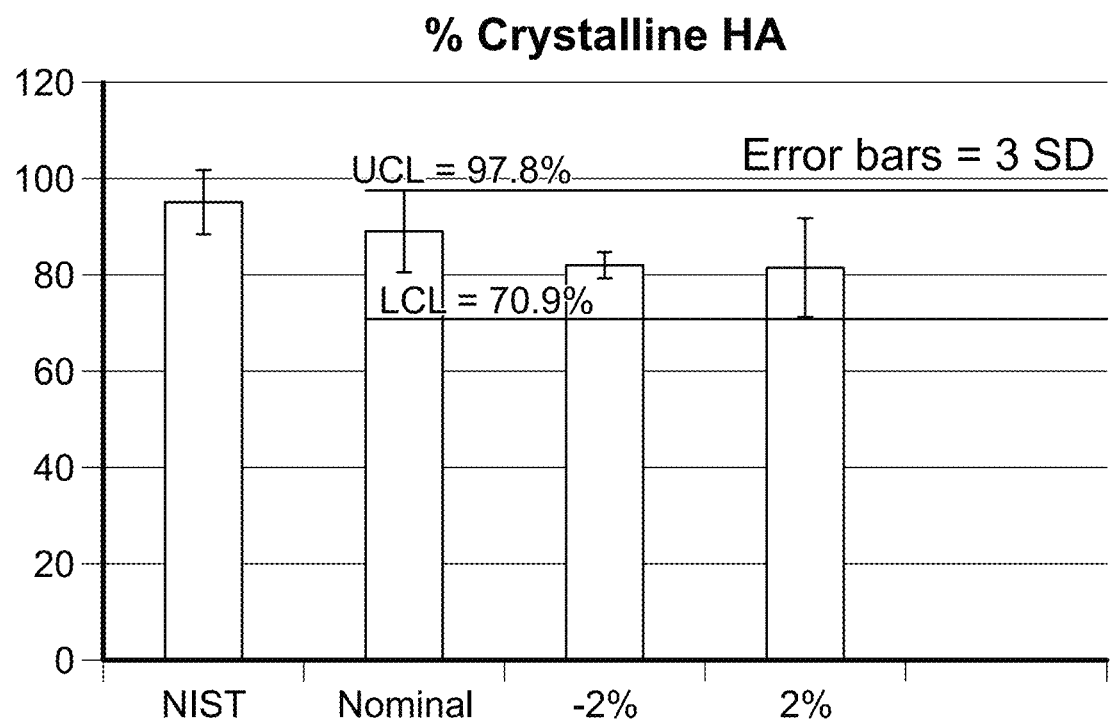
FIG. 15 is a chart showing the crystallinity of the hydroxyapatite in the five samples described in FIG. 14.

FIG. 15 shows the crystallinity of the coatings as determined by XRD for HA coated materials prepared by deposition in the full scale system according to Example 6 at nominal and process limits. Crystallinity was determined based on areas under selected diffraction peaks on the coating and compared to the same peak areas on the highly crystalline NIST standard. The balance of material not reported is not amorphous as found in PSHA deposits. Crystallinity values less than 100% reflect the fine grain size of the films and the fact that grain boundaries are disordered and do not contribute much to diffracted peak areas. Amorphous content is determined by DSC.

Figure 16:
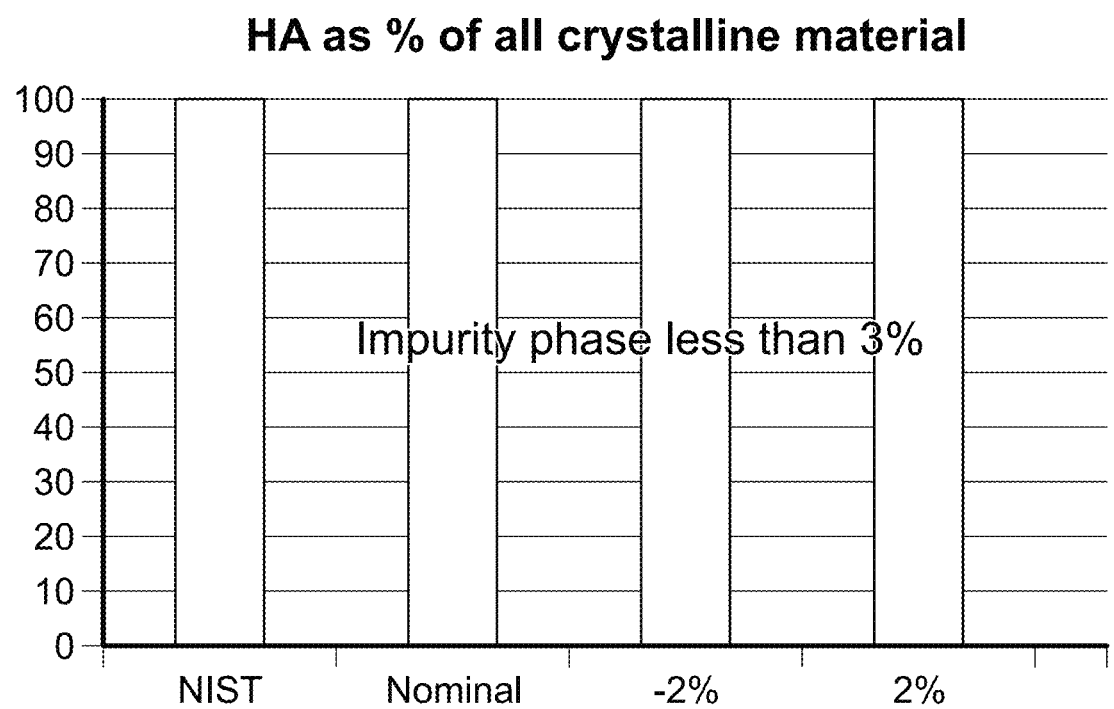
FIG. 16 is a chart showing the percentage of crystalline hydroxyapatite in the materials formed by the SoDHA process in the five samples described in FIG. 14.

FIG. 16 shows the percentage of HA as crystalline material out of all crystalline material in the HA coated substrates prepared by deposition in the full scale system according to Example 6. In other words, it is a measure of the phase purity of the films.

Figure 17:
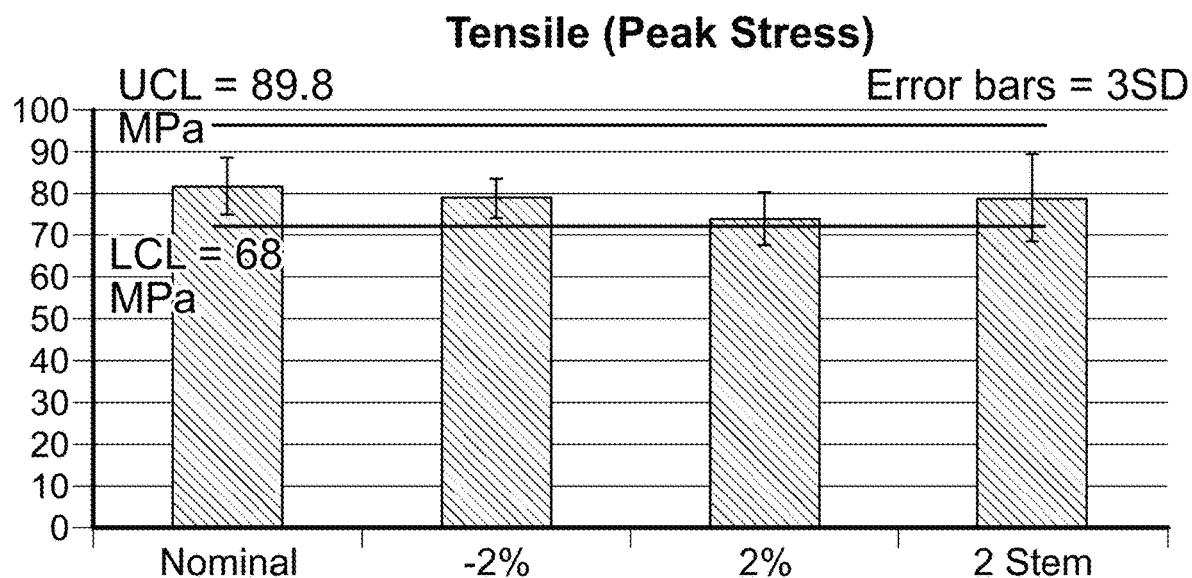
FIG. 17 is a chart showing the tensile strength of crystalline hydroxyapatite in the materials formed by the SoDHA process in the five samples described in FIG. 14.

FIG. 17 shows tensile adhesion as determined by ASTM F1147 of HA films prepared by deposition in the full scale system according to Example 6.

Figure 18:
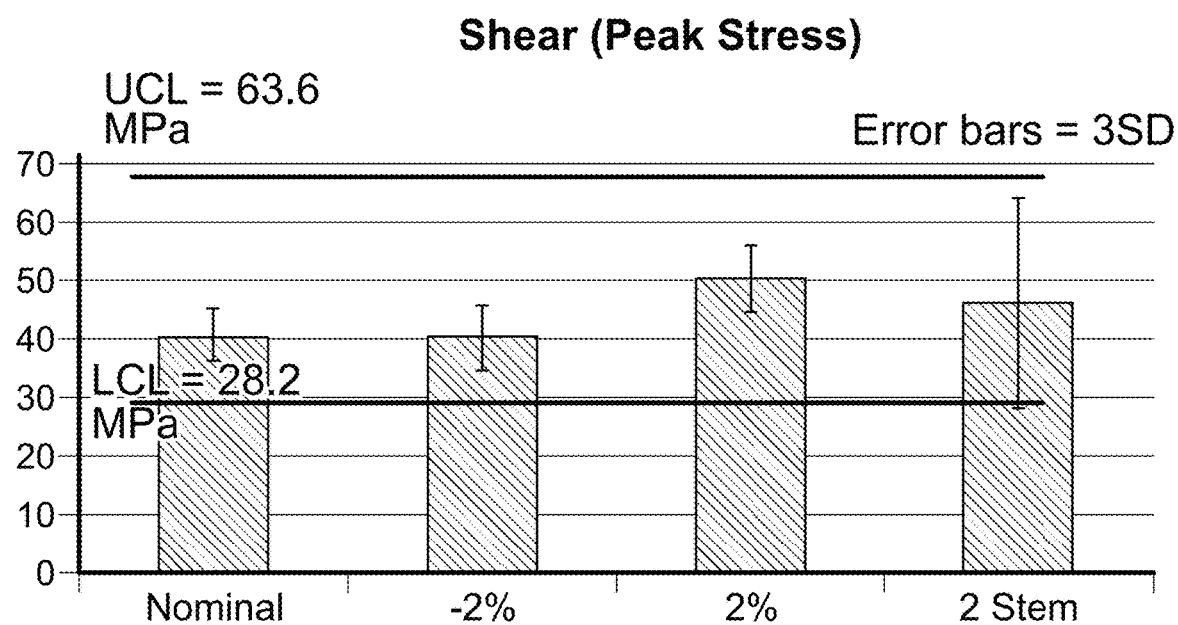
FIG. 18 is a chart showing the shear strength of crystalline hydroxyapatite in the materials formed by the SoDHA process in the five samples described in FIG. 14.

FIG. 18 shows shear adhesion as determined by ASTM F1044 of HA films prepared by deposition in the full scale system according to Example 6.

EXAMPLE 11

XRD Characterization

In this example, SoDHA HA prepared by deposition in the full scale system according to Example 6 and SoDOCP coatings prepared according to Example 7, were characterized by XRD. The nominal conditions were used to prepare both coatings.

Figure 19:
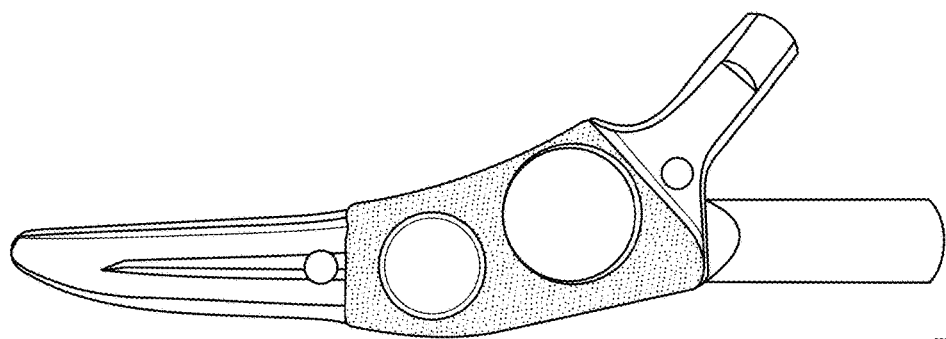
FIG. 19 shows a hip stem coupon fixture used in the XRD characterization study described herein.

Titanium discs (1" diameter) were processed in the fixtures shown in FIG. 19. These fixtures were fabricated from Depuy Tri-Lock BPS size 7 and 8 hip stem implants, and the discs are held into the recessed holes with stainless steel set screws.

Discs (and fixtures) were activated according to Example 3, except using 2.5N NaOH at 45° C. for 4 hours prior to coating in the full scale process apparatus. A total of 16 flat discs were coated in 8 fixtures utilizing two, two hour coating sequences.

Figure 20A:
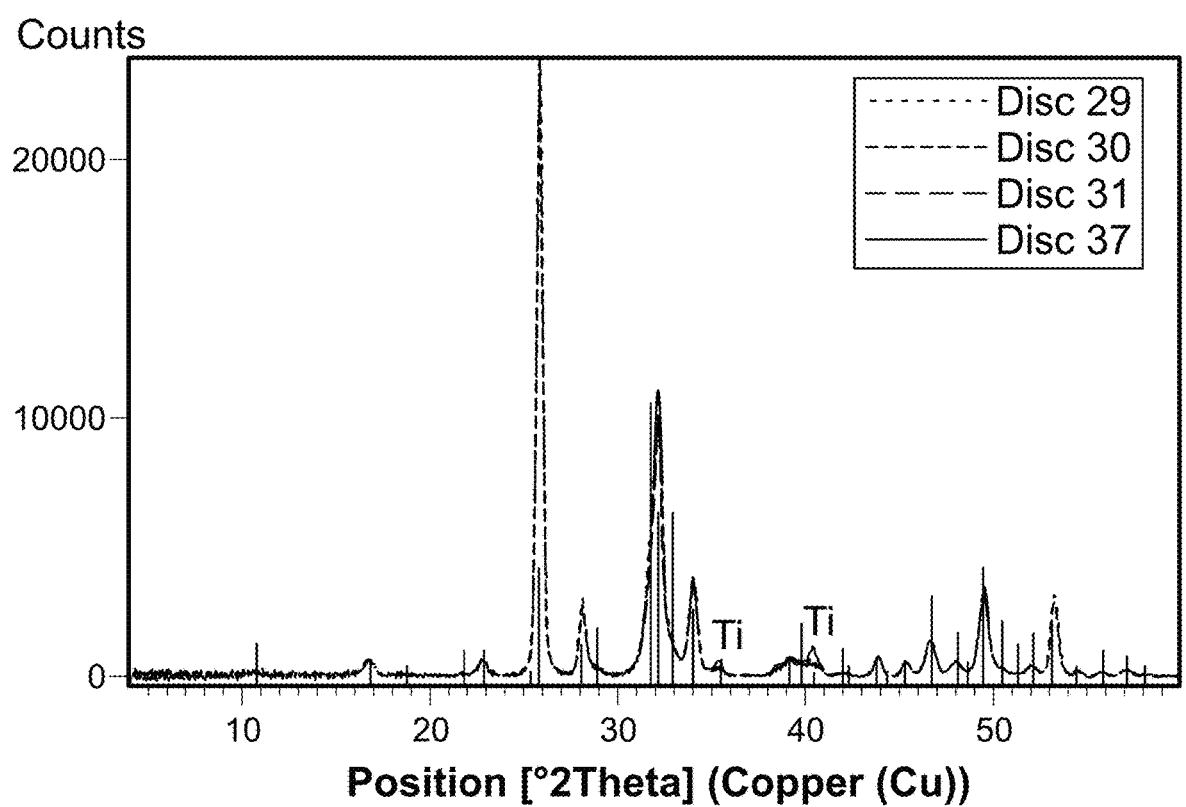
FIG. 20A shows superimposed XRD scans for as coated SoDHA HA discs.
Figure 20B:
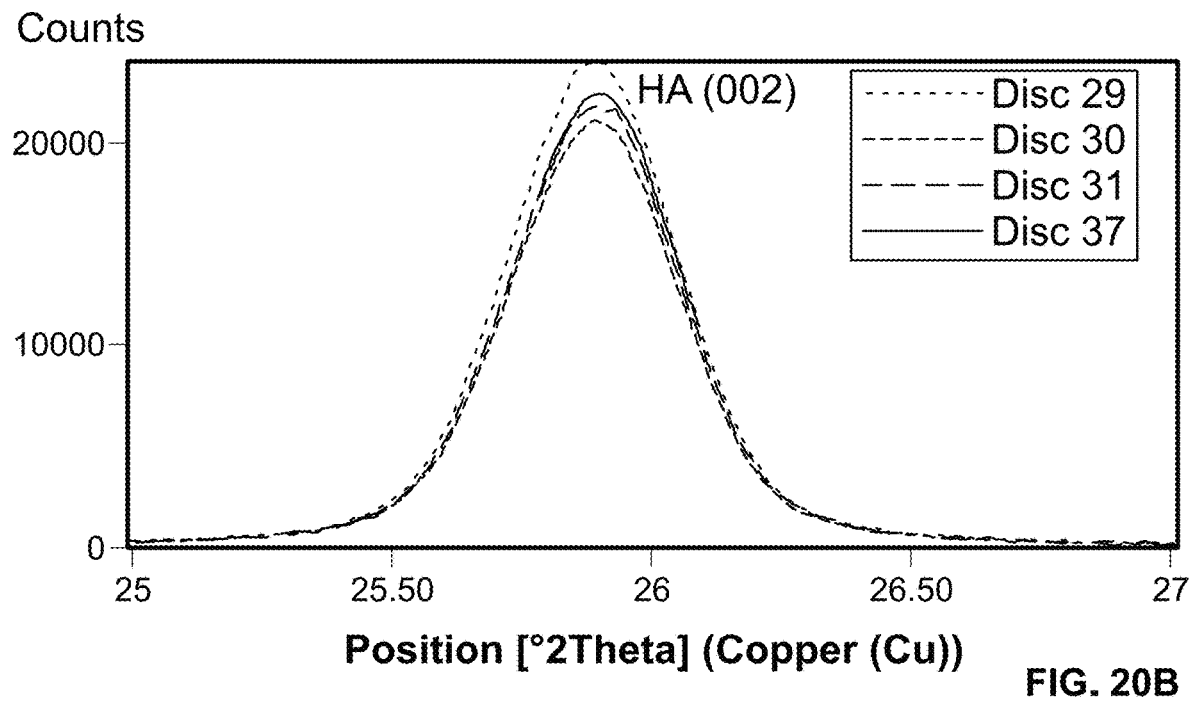
FIG. 20B shows 25° to 27° 2θ of the superimposed XRD scans of FIG. 18A.

Four as coated discs were analyzed. Superimposed XRD plots, (FIGS. 20A and 20B) show that the HA coating is phase pure HA (within the detection limits of the X-ray equipment) and the HA coating was highly textured in the (002) crystal orientation. FIG. 20B shows the peak from 25 to 27° 2θ. Superimposed XRD scans for the as coated SoDHA HA discs were measured with the background calculated and removed using Panalytical X'Pert software. It is also noted that these observations are consistent with discs activated under more aggressive NaOH exposure of 5N and 60° C.

Figure 21A:
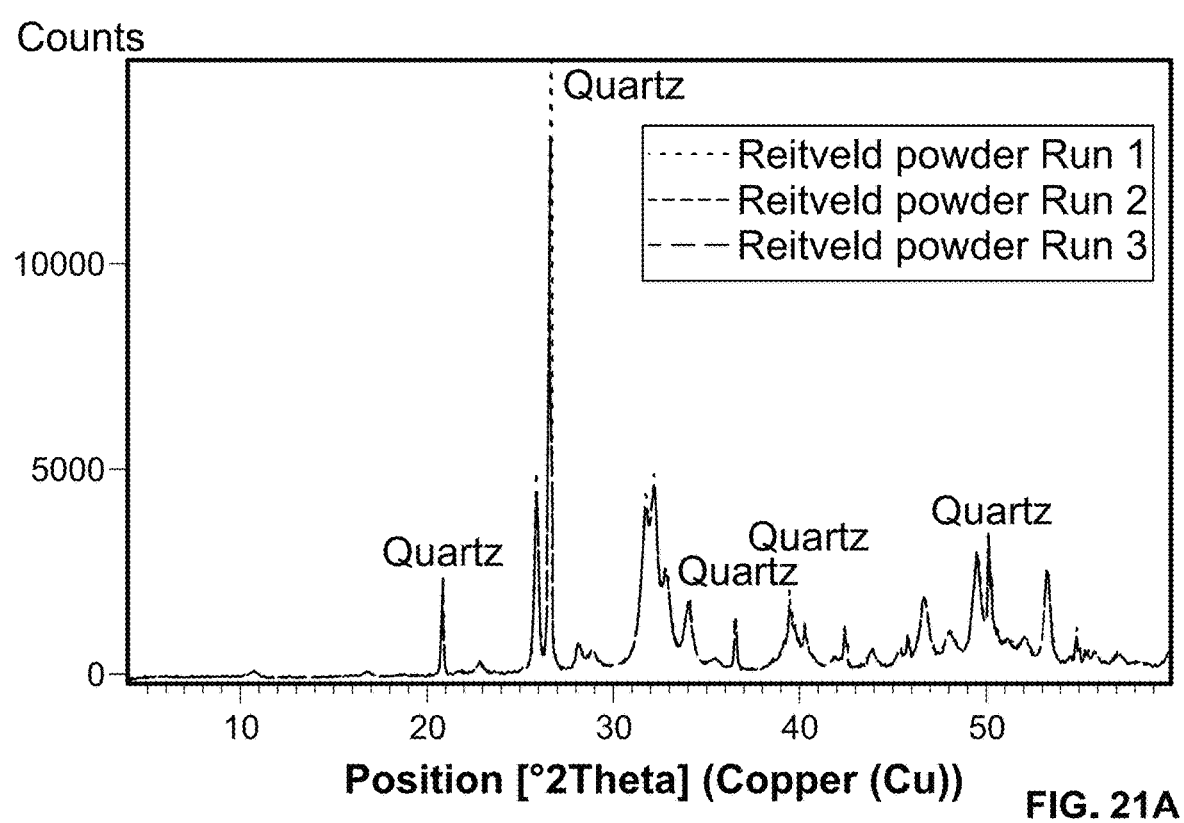
FIG. 21A shows multiple XRD scans of a scraped SoDHA HA powder mixed with quartz powders.

Scraped SoDHA HA powders were analyzed by powder XRD using Rietveld analysis, as shown in FIG. 21A. Care was taken to scrape the coated HA material down to the Ti substrate without generating excessive Ti contamination in the powder. Due to the relatively low mass (6-8 mg) of powder on each of the coated flat substrates, it was desirable to scrape 6 substrates to obtain approximately 15 mg of SoDHA powder. The mass of SoDHA and quartz standard mixed as an internal standard are presented in Table 3. Compiled XRD scans (1 powder, 3 repeats) are shown for SoDHA HA in FIG. 21A.

TABLE 3

Calculated wt % quartz and SoDHA HA in prepared powder

| Mass scraped SoDHA powder (mg) | Mass quartz standard (mg) | Wt % SoDHA | Wt % quartz |
|---|---|---|---|
| 22.6 | 5.5 | 80.43 | 19.57 |

Figure 21B:
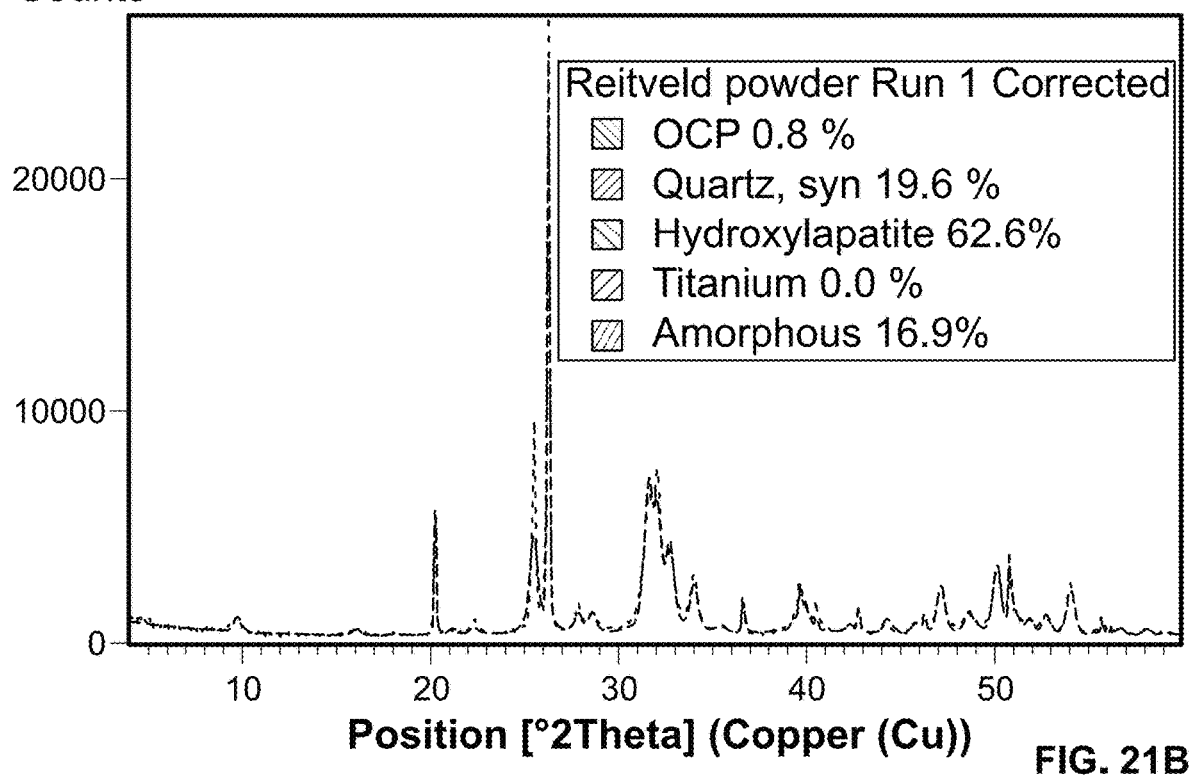
FIG. 21B shows representative Rietveld refined XRD scans of crystallographic quantification carried out for SoDHA HA-quartz powder mixtures.

Results presented in Table 4 show a measured crystalline HA content of 80.28%. It is noted that the 100% intensity octacalcium phosphate (OCP) peak (010) that occurs at 4.72 °2θ in a randomly oriented powder was not observed in any of the SoDHA HA powder XRD traces. It is therefore concluded that there is little-to-no OCP in the scraped SoDHA HA powders, and any OCP calculated by the Rietveld model is likely an artifact of the XRD background curve at angles approaching 3°2θ (FIG. 21B).

TABLE 4

Crystallographic composition from Rietveld analysis

| | | Compensated for Quartz content | | | | Crystallographically disordered content | |
|---|---|---|---|---|---|---|---|
| XRD Run | HA (wt %) | Crystallographically disordered component (wt %) | HA (wt %) | Crystallographically disordered component (wt %) | HA content Ave (wt %) | Std Dev | Ave (wt %) | Std Dev |
| 1 | 62.6 | 16.9 | 77.96 | 21.05 | 80.28 | 2.19 | 19.22 | 1.75 |
| 2 | 64.7 | 15.3 | 80.57 | 19.05 | | | | |
| 3 | 66.1 | 14.1 | 82.32 | 17.56 | | | | |

Figure 22:
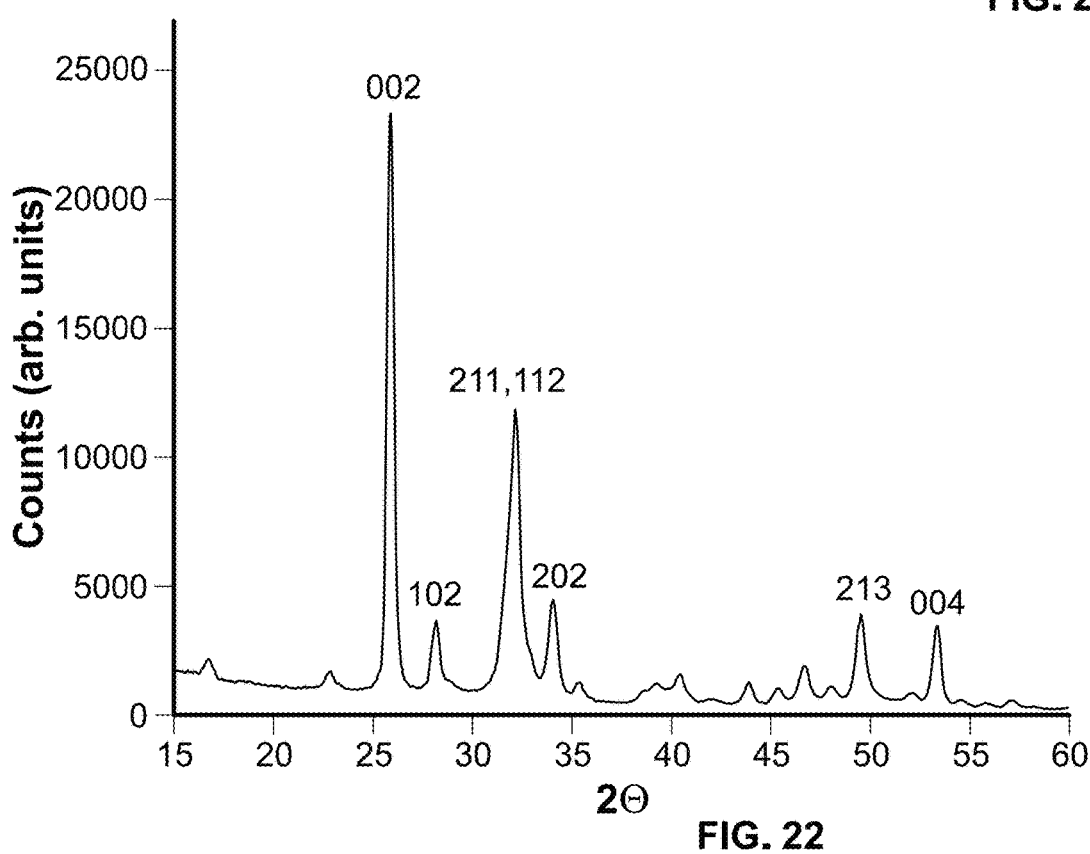
FIG. 22 shows an averaged representative XRD scan of SoDHA HA coated discs.

Table 5 shows the measured 2θ° values, together with the relative intensities of various peaks, as determined using XRD of the HA samples. Background was calculated and removed using Panalytical X'Pert software. The XRD peak indices for standard HA powder (PDF number 09-0432) are inserted for reference. The relative intensity of each the peak was calculated as a percentage of the most intense peak in the scan. It is noted that not all peaks published in the NIST SRM data were observed in the as coated SoDHA HA coating due to preferred orientation in the coating. It also is noted that the 100% intensity peak in a randomly oriented powder is the (211) peak, occurring at 31.76° 2θ (published NIST data SRM 2910a), whereas the 100% intensity peak observed for as coated SoDHA HA discs is the (002) peak (and also the (004) peak at 53.14° 2θ) occurring at 25.89° 2θ (FIG. 22). The increased intensity of the (002) peak indicates highly oriented crystals orthogonal to the (002) plane.

TABLE 5

SoDHA XRD Peaks

| d | 2θ | Relative intensity (%) |
|---|---|---|
| 002 | 25.89 ± 0.02 | 100 |
| 102 | 28.13 ± 0.02 | 15.5-16.5 |
| 211 | 31.75 ± 0.02 | 27-28 |
| 112 | 32.17 ± 0.02 | 50.5-60.5 |
| 202 | 34.05 ± 0.02 | 19-20 |
| 213 | 49.51 ± 0.02 | 16.5-17.5 |
| 004 | 53.29 ± 0.02 | 14-15 |

The SoDHA samples were determined to have the average crystallite sizes shown in Table 6.

TABLE 6

SoDHA Crystallite Sizes

| | Average crystallite size τ (nm) | | |
|---|---|---|---|
| Sample | τ HA (200) | τ HA (002) | τ HA (210) |
| Nominal | 20.50 | 68.61 | 49.19 |

Figure 23:
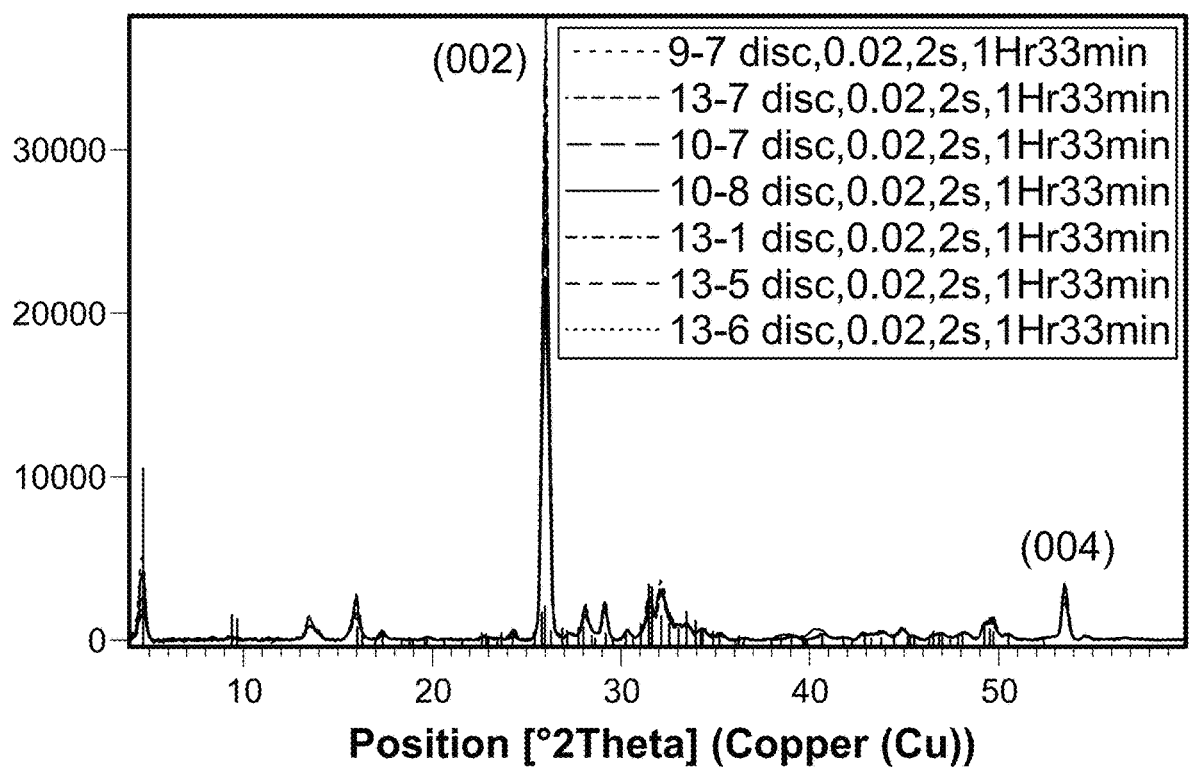
FIG. 23 shows multiple XRD scans of a scraped solution deposited octacalcium phosphate (SoDOCP) OCP powder.

An XRD spectrum overlay of the OCP coatings is shown in FIG. 23. Table 7 shows the measured 2θ° value, together with the relative intensity of each peak after the background was calculated and removed. The relative intensity of each peak was calculated as a percentage of the most intense peak in the scan.

TABLE 7

SoDOCP OCP XRD Peaks

| d-spacing | 2θ | Relative intensity (%) |
|---|---|---|
| 0 1 0 | 4.67 ± 0.02 | 6-21 |
| -1 0 -1 | 15.98 ± 0.02 | 4-11 |
| 0 0 2 | 26.01 ± 0.02 | 100 |
| 2 4 1 | 28.14 ± 0.02 | 5-11 |
| 0 -3 2 | 29.14 ± 0.02 | 6-12 |
| 2 6 0 | 31.57 ± 0.02 | 5-13 |

It is noted that the 100% intensity peak in a randomly oriented powder is the (010) peak, occurring at 4.72° 2θ (published JCPDS 00-026-1056 data), whereas the 100% intensity peak observed for as coated SoDHA OCP discs is the (002) peak occurring at 26.00° 2θ. The increased intensity of the (002) peak (and also the (004) peak at 53.5° 2θ) indicates highly oriented crystals in the (002) plane.

EXAMPLE 12

FTIR Characterization

Figure 24:
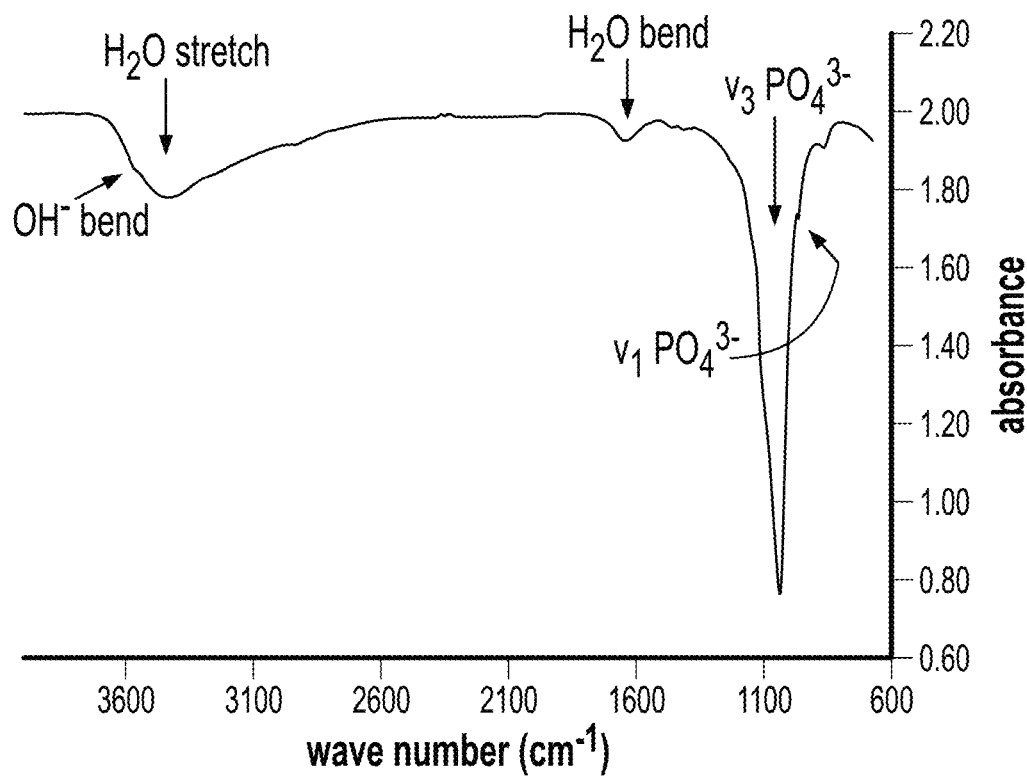
FIG. 24 shows a Fourier transform infrared spectroscopy (FTIR) spectrum of a scraped SoDHA HA powder.

An FTIR spectrum was obtained of the SoDHA HA prepared according to Example 5. The FTIR spectrum is shown in FIG. 24.

EXAMPLE 13

Dissolution

Figure 25:
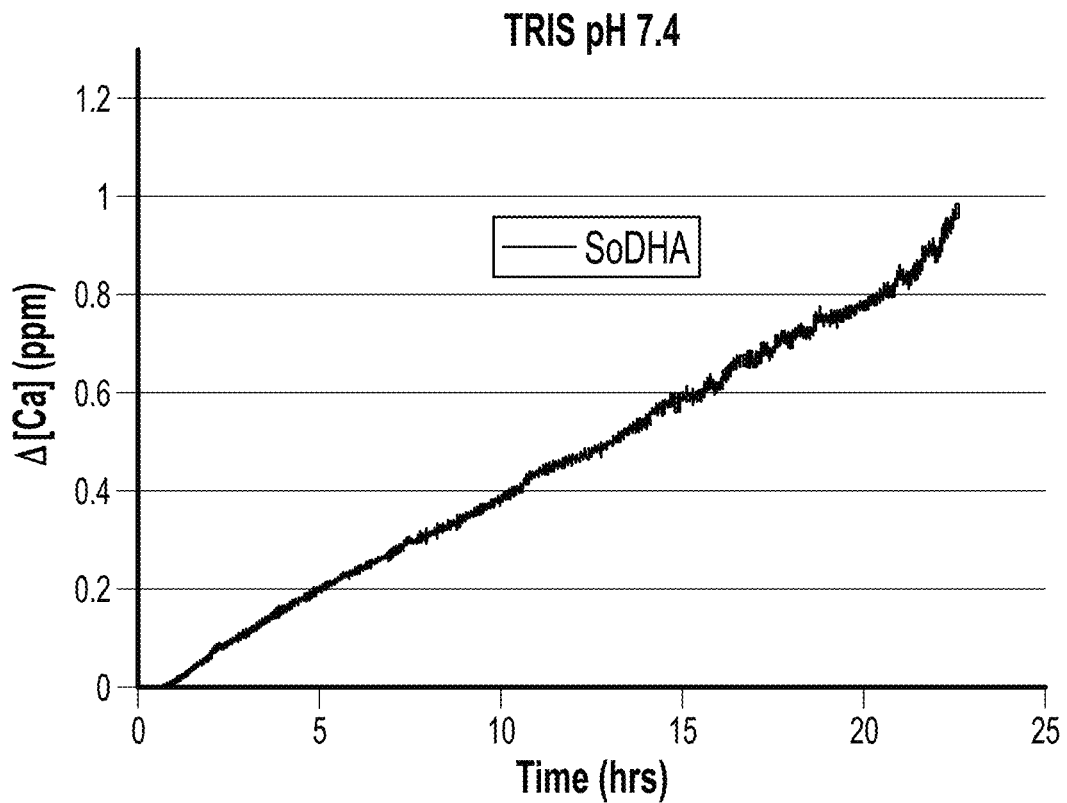
FIG. 25 is a chart showing the dissolution rate of a SoDHA HA sample.
Figure 26:
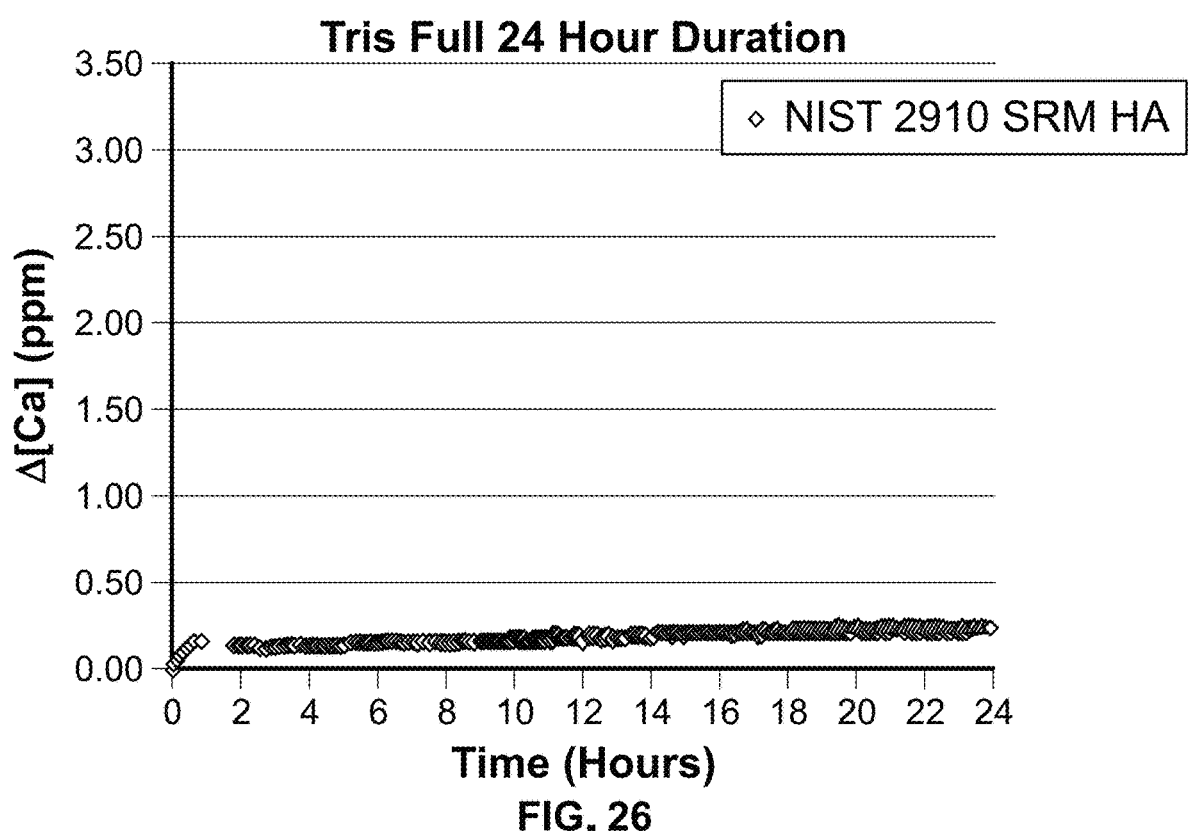
FIG. 26 is a chart showing the dissolution rate of a National Institute of Standards and Technology (NIST) standard HA sample.

Dissolution rates of the SoDHA coating and of a NIST hydroxyapatite reference material were determined by placing the samples in a tris buffered saline solutions at pH 7.4 and measuring change in calcium concentration. FIG. 25 shows the dissolution results for the SoDHA HA coating, and FIG. 26 shows the dissolution results for the NIST standard. While the NIST sample stopped releasing calcium after less than two hours, the SoDHA sample released calcium for more than 20 hours with no clear dissolution plateau.

EXAMPLE 14

Differential Scanning Calorimetry (DSC)

Differential Scanning calorimetry (DSC) has been previously investigated to directly observe, and qualitatively measure, the thermal recrystallization of amorphous calcium phosphate phases in plasma sprayed hydroxyapatite materials. It has been reported that amorphous calcium phosphate recrystallizes by a series of exothermic reactions that occur at different temperatures (within the range of 500° C. and 750° C.) and with different amplitudes dependent upon changes in the plasma spraying parameters (e.g. plasma power, feed rate, coating thickness etc.). Reactions are seen by the exothermic peak at approximately 500-550° C. (the crystallization of hydroxyl-rich amorphous regions in the material), the exothermic peak at approximately 600-650° C. (the diffusion of hydroxyl ions into hydroxyl-depleted regions), and the exothermic peak approximately 720-750° C. (crystallization of oxyapatite phase).

In this example, DSC was used to observe any phase transitions (e.g. recrystallization) that can occur in hydroxyapatite/calcium phosphate materials as a consequence of impurities and/or amorphous phases on heating up to 725° C.

Solution deposited SoDHA HA powders prepared according to Example 5 were scraped from flat Ti64 witness coupons. Each powder material was tested a minimum of 3 times using the DSC. The Pyris DSC analysis software was used to measure the peak areas and peak positions (between 550 and 710° C.) for all powder samples, and the resulting recrystallization energies (J/g) were calculated.

Figure 27:
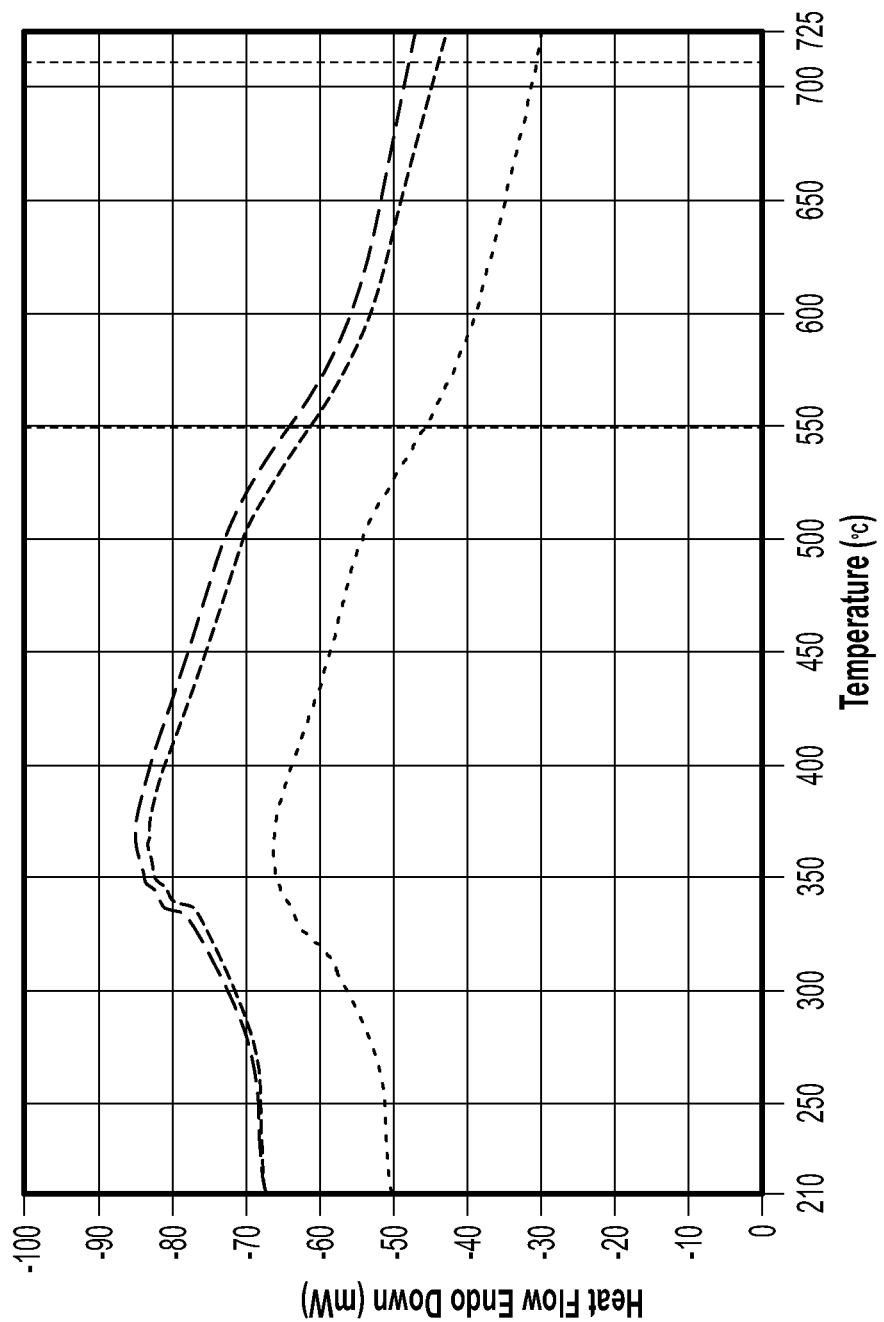
FIG. 27 shows DSC traces from scraped SoDHA powders showing no discernible exothermic peaks on heating.

DSC analysis of SoDHA powders scraped from coated Ti witness coupons is shown in FIG. 27, which shows no discernible exothermic peaks on heating.

In the area of interest, i.e. 550° C. and 710° C., there were no exothermic peaks seen in the DSC heating curves generated for scraped SoDHA powders, indicating very little, if any, glassy amorphous phases. Based on the DSC curves, there was less than 2 wt % glassy amorphous material in the SoDHA powders tested. It was also observed that the SoDHA powders analyzed using DSC were a gray color coming out of the test, indicating a small amount of titanium is removed from the substrates on scraping and subsequently oxidizes during DSC testing.

EXAMPLE 15

Canine Study

The objective of the canine study was to assess the effect on implant fixation of calcium phosphate coatings when deposited on a commercially available titanium porous implant. The fixation performance was assessed by testing the push-out strength of the bone implant interface and by histomorphometric analysis of bone ingrowth, bone apposition, and bone healing of the gap region. In this study, the performance of the calcium phosphate coatings was compared to non-coated porous implants and the same porous implant coated with a commercially available plasma spray hydroxyapatite coating.

Implants were placed in cylindrical defects created in the cancellous bone of nine large, skeletally mature, mixed-breed hounds. A canine was selected as a model for testing as the bone structure of canines closely resembles human bone. The sites of implantation selected for this study provide a large volume of cancellous bone. A total of 9 dogs were enrolled in this study. The dogs obtained from VBF (Madison, Ga.) were purchased from Antech, Inc. The breed of dog was Mongrel. The nine dogs were between approximately 1 year and 3 years of age at the time of enrollment, and weighed between 25 and 31 kg. All dogs enrolled in the study were intact males with the exception of one, which was female. All nine dogs were deemed healthy upon arrival to VBF. Examination at SJTRI prior to surgery revealed no obvious abnormalities.

The effects of these coatings on implant fixation were assessed in both 1 mm gap and line-to-line or exact fits, as they represent a range of implant to host bone fit scenarios that are encountered in total joint replacement procedures in humans. Four defects per animal were created in cancellous bone to create side-by-side regions with line-to-line and 1 mm radial gap fits between the porous coated surface of 6 mm diameter implants and the host bone. These defects were created bilaterally in the proximal humerus and distal femur. Two additional defects per animal were created in cancellous bone distal to the first defect in the humerus, bilaterally, in order to place a single implant with a 1 mm radial gap fit.

This was done due to the limitation on the number of anatomical sites suitable for implantation of side by side implants in this model.

The following test articles were used:

Gription™ with SoDHA HA coating (HA version of the SoDHA coating)—10 mm length and 11 mm length, 6 mm diameter.

Gription™ with SoDHA OCP coating (octacalcium phosphate version of the SoDHA coating)—10 mm length and 11 mm length, 6 mm diameter Gription™ without coating—10 mm length and 11 mm length, 6 mm diameter Gription™ Plasma Spray HA (plasma spray HA coating)—10 mm length and 11 mm length, 6 mm diameter The animals in this study were handled and maintained in accordance with the requirements of the Animal Welfare Act. Compliance was accomplished by conforming to the standards in the Guide for the Care and the Use of Laboratory Animals, ILAR, National Academy Press, revised 1996. The animals were evaluated daily for behavior, appearance, urination, defecation, respiration, eating, and mobility.

Dogs were housed according to AR020, *Routine Care for Dogs*. Cages in cages with stainless steel runs, with approximately 24 square feet of floor space. Floors were elevated with vinyl coated expanded mesh floors that were removable for sanitation. Cages were hosed clean at least once daily or more frequently as needed to prevent accumulation of excreta. Animals may have remained in place during daily cleaning with measures taken to assure that the animals remained dry. All cleaning or disinfecting agents used in the vivarium were designated as USDA "Food Safe" and approved for use by the Attending Veterinarian.

Sanitation of cages and holding rooms was performed using a pressure washer or other approved agent every 2-6 weeks (frequency based on biological monitoring). Animals were removed from the cage during sanitation to prevent exposure to hot water or disinfectant solutions. All surfaces of the cage and the room were rinsed thoroughly when disinfectant solutions were used.

Animals were acclimated as stated per AR045, *Quarantine, Acclimation, Stabilization, and Enrollment*. Section 6.1.4 of AR045 states "Dogs are obtained from USDA Class A dealers are held for acclimation for approximately 3 days. Quarantine is not required." As per AR045, dogs were obtained from a single vendor and were housed seperately off-siteAnimals were held for at least 2 days for physiologic stabilization prior to the surgical implantation procedure.

As per AR020, *Routine Care for Dogs*, dogs were fed an amount appropriate for their weight and activity according to USDA and National Research Council regulations. All feed was provided in stainless steel bowls. All animals not scheduled for a procedure were fed at least once daily. Animals scheduled for a procedure were fasted 12-24 hours before the procedure. There were no known contaminants considered to interfere with the validity of the study.

The animals on this study had free access to fresh clean water as per AR020, *Routine Care for Dogs*. There were no known contaminants considered to interfere with the validity of the study.

All animals undergoing surgical procedures were given anesthesia medications consistent with AR006, *Use of Sedatives, Analgesics and Anesthetics*. Animals received the following medications at implant as listed in Tables 8a-8c.

TABLE 8a

Pre-Operative Medications for all animals

| Medication | Dose | Duration |
|---|---|---|
| Carprofen | 100 mg IM | At the time of sedation |
| Atropine | 1 mg IM | At the time of sedation |
| Hydromorphone | 2.5 mg IM | At the time of sedation |
| Propofol | 100-300 mg IV | At the time of induction |
| Dexmeditomidine | 0.25-0.5 mg IV | As needed, at the time of sedation |
| Atipamezole | 2.5-5 mg IV or IM | As needed for reversal of dexmeditomidine |

TABLE 8b

Intra-Operative Medication

| Medication | Dose | Duration |
|---|---|---|
| Isoflurane | 1.0-3.5% | During implant procedure |
| Cefazolin | 1000 mg in 250 ml 0.9% Saline, CRI at 10 mg/kg/hr | During implant procedure |
| LRS and or NaCl Drip | 5 ml/kg/hr IV | During implant procedure |
| Cefazolin | 500 mg IV | After CRI, every 90 minutes during implant procedure |
| Atropine | 1-2 mg IV | As needed, for bradycardia |

TABLE 8c

Post-Operative Medication

| Medication | Dose | Duration |
|---|---|---|
| Hydromorphone | 2.5 mg IM | Immediately post-operatively |
| Buprenorphine | 0.3-0.45 mg IM | Twice daily for first 24 hours |
| Carprofen | 50-75 mg IM or PO | Twice daily for 4 days, then as needed for pain |
| Cephalexin | 1000 mg IM or PO | Twice daily for 4 days |

All dogs were monitored during the surgery for heart rate, respiration, pulse oximetry for oxygen saturation, expired carbon dioxide, body temperature and limb-lead electrocardiography.

The ipsilateral forelimb and pelvic limb were prepared and aseptically draped for surgery. A 10 cm skin incision was made on the craniolateral aspect of the shoulder joint extending from the acrornion to the proximal third of the humerus. Hemorrhage was controlled with electrocautery. Superficial fascia was incised along the same plane. The acromial head of the deltoid muscle was undermined, mobilized, and retracted caudally. Just distal to the tuberosity from the teres minor on the craniolateral flat surface of the proximal humerus, a battery powered drill was utilized to place a 2.4 mm guide pin oriented in a slightly proximal direction from 90 degrees to the bone surface. The position of the pin was evaluated fluoroscopically. Adjustments were made if necessary. A guide pin drill guide was then utilized to place a second 2.4 mm guide pin parallel and 17 mm distal to the first pin. A counterboring cannulated drill bit was then utilized to overdrill the proximal 2.4 mm guide pins creating a stepped or counterbored 6/8 mm diameter, approximately 24 mm long cylindrical defect. An 8 mm cannulated drill bit was then utilized to overdrill the distal 2.4 mm guide pin to create a defect approximately 14 mm in depth. During slow drilling, saline lavage was used to mitigate thermal necrosis from drill bit friction. Each defect was gently lavaged to remove bone debris. The periosteum immediately surrounding each defect was trimmed back 1-2 mm to prevent it from being carried into the defect during test article placement.

The two defects of the humerus were implanted with a test/control article such that the outer end of the implant was placed just below the cortical surface. First, a 6 mm diameter implant was placed into the 6 mm diameter segment of the upper humerus defect to create a line-to-line or exact fit between the implant and the cylindrical wall of the bone defect. A second 6 mm diameter implant was then placed into the 8 mm diameter segment of the upper humerus defect after first assembling 8 mm diameter titanium spacers to the ends of the implant. A 6 mm diameter implant with 8 mm diameter spacers was placed in the 8 mm diameter lower defect in the proximal humerus. When implanted, these spacers created a continuous, 1 mm radial gap between the porous coated surface of the implant and the bone defect. These spacers add 1 mm of length to each end of the radial gap implant assembly. Thicker (2 and 3 mm) spacers were also used for assembly to the lateral side of the radial gap implant to ensure spacer contact with cortical bone for mechanical support and to limit post-op bleeding when necessary. Test articles were placed in the proximal and distal defects and their positions recorded fluoroscopically.

The wound was then lavaged and closed in 3 layers, taking care to obliterate dead space as much as possible. The deep layer and subcutaneous layers were closed with 3-0 Vicryl. 4-0 Vicryl was used in a subcuticular pattern to complete the closure.

Following aseptic hanging leg prep with Ioban barrier drape placement, an 8 cm skin incision was made on the lateral aspect of the stifle on the same side, centered over the epicondyle. Hemorrhage was controlled with electrocautery. The biceps fascia was incised and retracted along the same plane allowing incision into the joint capsule. An area on the distolateral surface of the femur, just cranial and proximal to the origin of the lateral collateral ligament was identified. A 2.4 mm guide pin was placed at a 90 degree angle to the long axis of the femur. The position of the guide pin was evaluated fluoroscopically and adjusted if necessary. A ⅝ mm counterboring, cannulated drill bit was then utilized to create a lateral to medial cylindrical defect 24 mm in depth. Saline lavage was performed during and after drilling as described previously. Periosteum immediately surrounding the cylindrical defect was excised prior to test article placement. A 6 mm diameter implant was placed into the 6 mm diameter segment of the defect, creating an exact fit between implant and the wall of the bone defect. A second 6 mm diameter implant was placed in the 8 mm diameter segment of the defect following assembly of 8 mm diameter spacers to each end of the implant creating a region with a 1 mm radial gap fit between the implant and the wall of the defect. Following test article placement, the position of the implant was recorded with fluoroscopy. After wound lavage, the joint capsule was closed with 2-0 PDS, deep fascia was closed with 0-PDS in a simple interrupted pattern. Subcutaneous and subcuticular layer closure was performed with 3-0 Vicryl.

Figure 28:
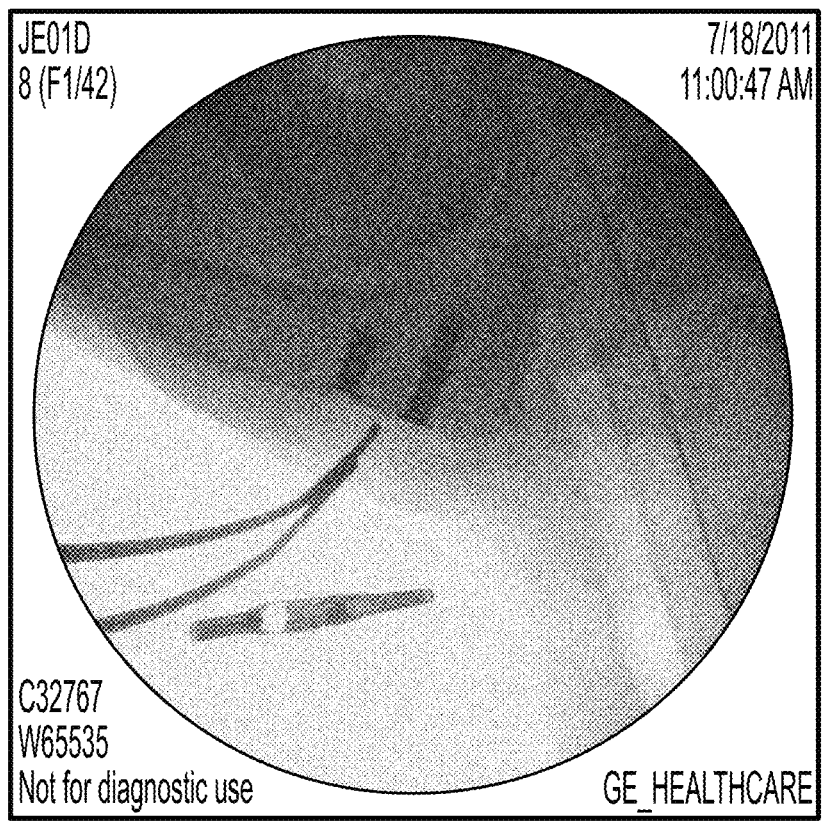
FIG. 28 is an image of a canine proximal humeral having two implants therein.
Figure 29:
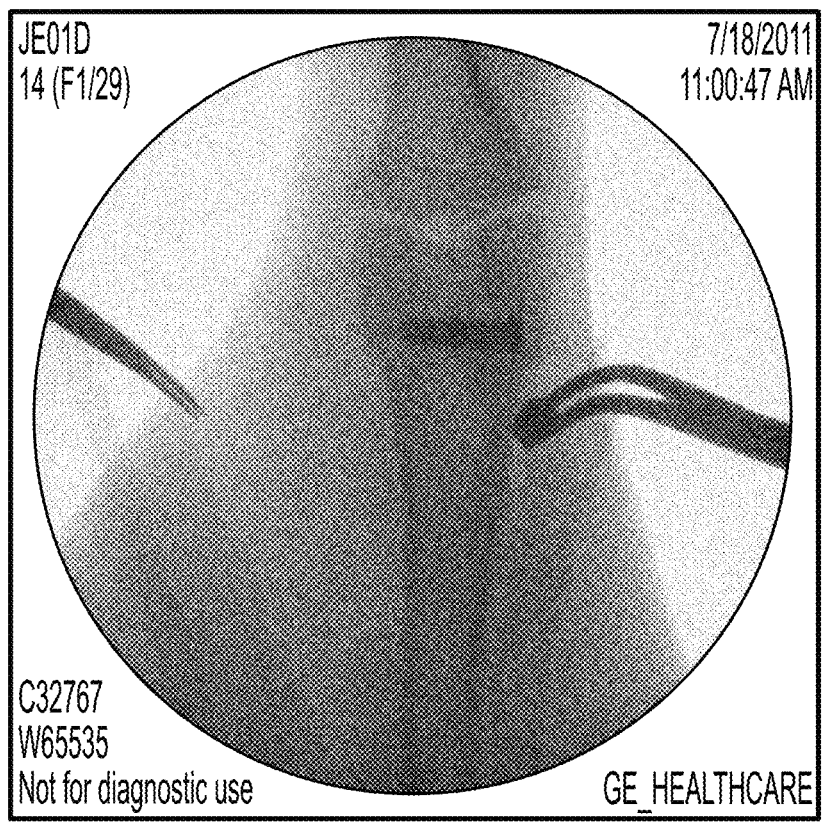
FIG. 29 is an image of a canine distal femur having an implant therein.

There were two implant sites per side. At the proximal humerus, SoDHA HA and Gription were placed, as shown in FIG. 28. For the proximal humerus, upper (more proximal) and lower (more distal) were the relative positions of two defects that were separated by 17 mm between their centers. At the distal femur SoDHA HA and PS HA were placed, as shown in FIG. 29. All implants were successfully placed.

The dog was rotated to the other side and after aseptic prep and sterile draping. The identical procedures were repeated on the contralateral fore and hind limbs.

Animals were observed at least once daily and in a manner consistent with ARO 11, *Assessment and Documentation of Animal Health and Welfare*. Specifically, dogs had general assessments of health consistent with current standards of record-keeping in veterinary medicine format.

No evidence of infection was observed. Several animals had one or more skin incisions dehisce, most likely secondary to licking. Bandages and e-collars were placed, but the animals removed them with ease. Some animals had fluid build-up around one or more incisions postoperatively. Fluid analysis and bacterial culture of the fluid from these animals revealed nonsuppurative inflammation with primary differential diagnosis of a seroma. No evidence of infection was observed. CBC and serum chemistries revealed no significant abnormalities and no evidence of a systemic infectious process. No inflammation was grossly observed to extend beyond the dermal layer, and no bone reaction was observed radio graphically or during gross necropsy. While endcaps detached from the implants in two animals, the implants remained intact with no evidence of loosening or migration which is suggestive of rigid fixation at the initial implant site.

All animals were terminated after 6-weeks. Animals were euthanasized using 5-7 ml (1800 mg-2520 mg) of Euthasol which was in accordance with AR007, *Euthanasia of Animals*, and consistent with the Report of the AVMA Guidelines on Euthanasia, June 2007.

A gross necropsy of implant sites was performed by a veterinary pathologist Implanted humeri and femurs were harvested, and dissected free of surrounding soft tissue. Samples were wrapped in saline-soaked gauze Immediately following necropsy, ex vivo fluoroscopy images were taken of each of the specimens in the anterior/posterior, longitudinal and transverse directions to visualize the implants within the cancellous bone Implanted bones were excised at time of necropsy, placed in heat-sealed plastic bags, shipped on wet ice to Histion, Inc. (Everett, Wash.), and processed for either histological evaluation or mechanical testing as described in Examples 16-17. Specimens were wrapped in saline-soaked gauze and shipped to Histion, Inc. (Everett, Wash.) for histological analysis.

EXAMPLE 16

Histology Results

The performance of the calcium phosphate coatings were compared to a non-coated porous implant and the same porous implant coated with a commercially available plasma spray hydroxyapatite coating. Fluoroscopic imaging revealed all implants were in place.

The results were consistent with successful implantation of coated and uncoated porous devices bilaterally in the proximal humerus and distal femur with a follow-up period of 6 weeks. The postoperative complications observed in the study population have no effect on the integrity of the study or its data. The study was successful in the utilization of this animal model to enable the comparison of porous implants with and without various coatings designed to improve fixation in cancellous bone.

Remaining tissue was trimmed as necessary, fixed in 10% neutral buffered formalin, and specimens containing the gap portions of each implant were embedded in methyl methacrylate. Two ground transverse sections stained with Stevenel's Blue/van Gieson were produced from each specimen and evaluated quantitatively to determine percent bone within the porous coating and percent bone within the gap area. Bone apposition to the outer perimeter (including inner surfaces contiguous with the outer perimeter) and total apposition (including perimeter apposition and apposition to surfaces within the interstices of the porous coating) measurements were taken from specimens placed in the upper proximal humerus and distal femur only. Data from both sections were averaged. Averaged data were used to determine differences between groups by ANOVA and the Tukey multiple comparisons test Implants placed in three different locations were compared separately. In the upper proximal humerus, Gription™ SoDHA HA and Gription™ SoDHA OCP implants were compared to Gription™ Porous Coating implants. In the distal femur, Gription™ SoDHA HA implants were compared to Gription™ Plasma Spray HA implants. Sections were also grouped according to location and evaluated qualitatively to determine the cellular and tissue responses to each implant type.

Histomorphometric analysis was performed blind to treatment on each slide. Low power digital images were captured of each section that included the gap and an additional amount of tissue surrounding each implant. Static histomorphometric analysis was completed to determine % bone apposition to the implant surface, % bone within the porous coating and % bone within the gap area. Ingrowth was measured as % total voids. Additional parameters evaluated include average coating thickness. The results, averaged over the various specimens are shown in Table 9 for SoDHA HA gap, SoDHA HA line-to-line, and Gription line-to-line implants.

TABLE 9

Histomorphometry Results

|  | % Ingrowth | % Apposition |
| --- | --- | --- |
| Gap | 21.4855272 | 16.19171 |
| Line-to-Line | 28.6462277 | 33.04744 |
| Gription Line-to-Line | 34.1005268 | 26.80749 |

The histomorphometry results showed that bone ingrowth into the gap and the porous coated surface at the upper proximal humerus implantation site for the Gription™ SoDHA HA implant (about 14% ingrowth) was better compared to Gription™ SoDHA OCP and significantly better compared to the Gription™ Porous Coating control group (about 8% ingrowth). Percent bone apposed to the outer perimeter and to the total implant perimeter was significantly better for the Gription™ SoDHA HA implant group (about 17.5% apposition) compared to the Gription™ Porous Coating group (about 4.5% apposition), with no significant difference between the Gription™ SoDHA HA and Gription™ SoDHA OCP groups.

Figure 30:
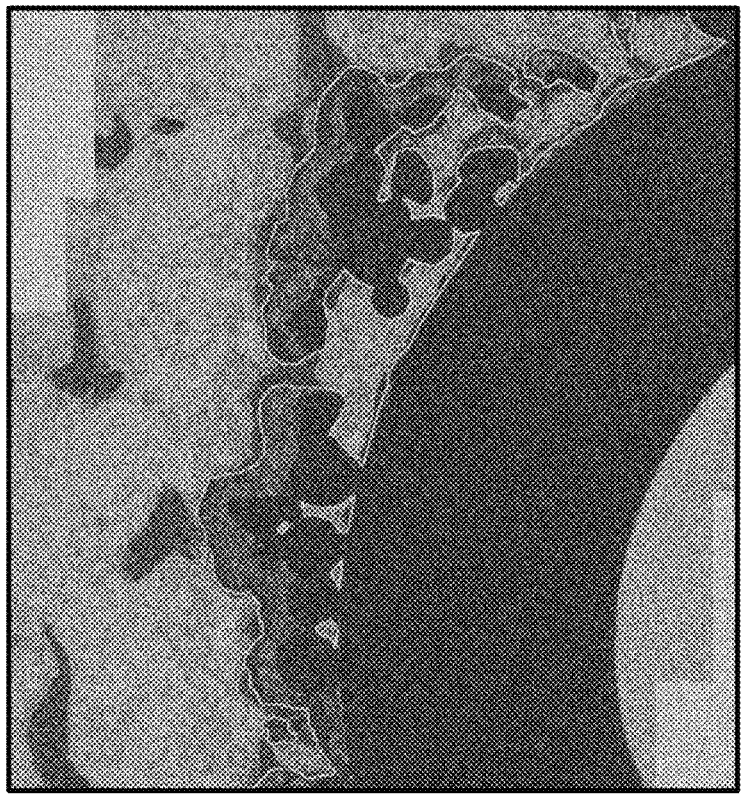
FIG. 30 is an image of a Gription™ Plasma Spray HA-coated implant in a test subject.
Figure 31:
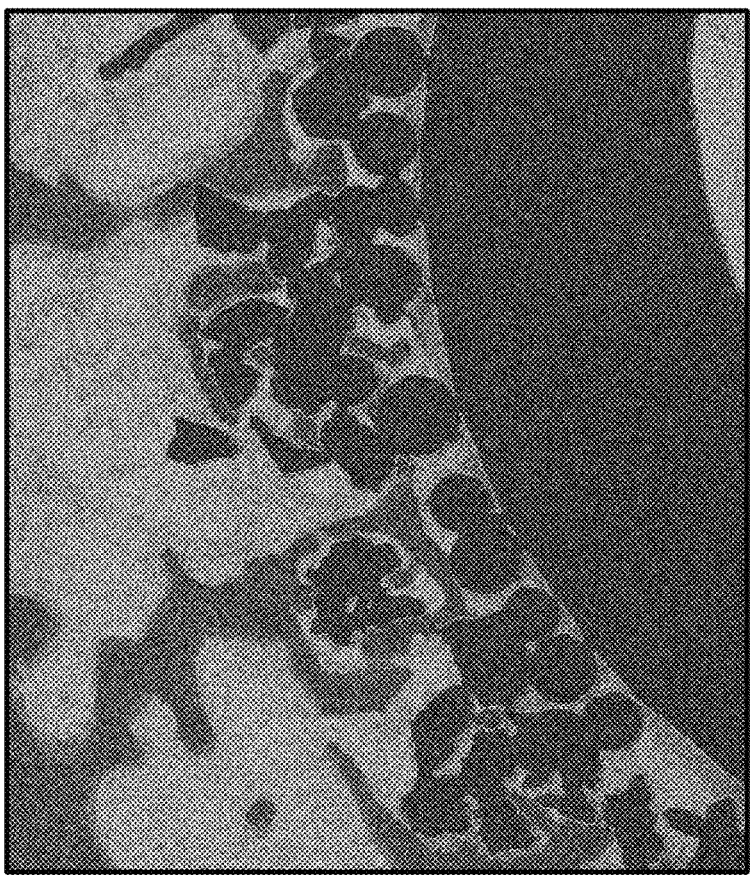
FIG. 31 is an image of a Gription™ SoDHA HA-coated implant in a test subject.

Additionally, bone ingrowth into the gap and the porous coated surface at the upper proximal humerus implantation site for the Gription™ SoDHA HA implant (about 14% ingrowth) was better compared to Gription™ Plasma Spray HA (about 12% ingrowth). Images of the Gription™ Plasma Spray HA and Gription™ SoDHA HA implants are shown in FIGS. 30 and 31, respectively.

Figure 32:
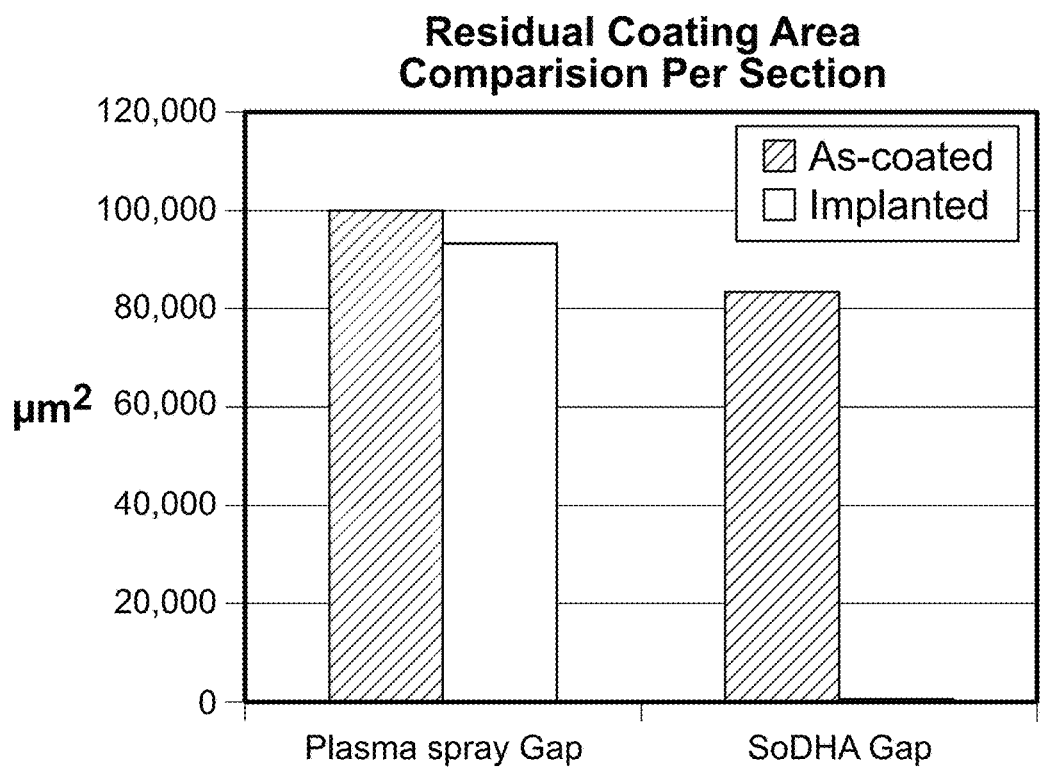
FIG. 32 is chart showing residual coating area before and after 6 weeks of implantation in plasma spray HA-coated and SoDHA HA-coated implants.

Additionally, residual coating area after 6 weeks of implantation was measured based on quantitative image analysis of sectioned implants, as shown in FIG. 32. In contrast to the Gription™ Plasma Spray HA-coated gap samples, the Gription™ SoDHA HA-coated samples had virtually no residual coating area.

Qualitative analysis showed more bone apposition deep into the porous coating with the Gription™ SoDHA HA group compared to the Gription™ SoDHA OCP and Gription™ Porous Coating group, the latter of which showed a fair amount of fibrous tissue apposition to the metal substrate. Collectively, these data suggest that Gription™ SoDHA HA implants performed best at the upper proximal humerus site.

When comparing Gription™ SoDHA HA, and Gription™ Plasma Spray HA implants placed in the distal femur, Gription™ SoDHA HA had the highest mean percent bone ingrowth into the gap and the porous coating of the groups.

The qualitative results showed little or no evidence of residual HA on the test implants by 6 weeks, and no evidence of particles, no inflammation, and no giant cells (GCs) surrounding any of the test implants. In addition, radiographic results showed no evidence of abnormal radiolucency surrounding any of the implants. Collectively, these data provide evidence that there is no safety issue associated with implantation of the test coatings through 6 weeks and suggest that the test HA coatings are largely absent by 6 weeks.

Gription™ SoDHA HA performed better than both Gription™ SoDHA OCP and Gription™ Porous Coating (significantly better compared to this latter group for percent bone in the porous coating and the gap areas and percent bone apposition to the porous outer and total perimeters) in the upper proximal humerus. Qualitative analysis showed little or no residual test HA by 6 weeks. Based on a lack of inflammation, GCs, particles and radiolucency surrounding the implants, there was no adverse response to the implants or the test HA coatings detected at any of the implant sites 6 weeks after implantation.

EXAMPLE 17

Mechanical Tests

At total of 90 5 mm thick cancellous bone blocks were removed from the implanted bones that were excised samples obtained in Example 15. After being radiographed to facilitate processing, specimens were trimmed to remove excess bone, including bone overgrowth at the insertion site and/or around the spacer. Specimens were trimmed to leave not less than 4 mm of bone surrounding the implant on all sides. Five millimeter-thick wafers were cut perpendicular to the long axis of each gap-fit implant and used for mechanical testing. Five millimeter-thick wafers were cut perpendicular to the long axis of each line-to-line fit implant for mechanical testing. Once prepared, the mechanical test specimens were wrapped in saline soaked gauze, frozen at −70° C. and shipped together on dry ice to Histion (Everett, Wash.) for mechanical testing. Remaining portions of each trimmed specimen were fixed in NBF and used for histology.

Specimens designated for histology were trimmed and then cut perpendicular to the long axis of the implant. Two (2) ground transverse sections spaced approximately 200-400 μm from one another were produced from the region of interest (ROI) containing the gaps. Sections (n=108) were stained with Toluidine blue/Paragon stains or other appropriate stain(s) and evaluated histomorphometrically.

Static push-out testing was conducted on specimens at 1 mm/minute until a 75% drop in peak force. Tests were formed using a MTS Sintech 65/G static test machine with a 2.5 kN load cell and 4.0 mm diameter pin. Each specimen consisted of a canine bone slice containing a formerly implanted peg that was cemented into a custom potting fixture. The MTS TestWorks (rev 4.08B) software was used to apply a compressive load at 1.0 mm per minute until a 75% drop from peak load occurred.

Force and displacement were recorded peak stress and energy at peak force was calculated for each specimen and sample. Table 10 serves as a summary of the canine push-out study, showing the average and standard deviation stress for Gription, SoDHA HA, SoDHA OCP (alternatively SoDOCP OCP), and plasma spray (PS) HA and various implant locations. Both gap and line-to-line implants are illustrated.

TABLE 10

Push out Stress; Separated Left and Right
Average Peak Stress and Standard Deviation (MPa)

| Fit | Site | Gription AVG | Gription SD | SoDHA HA AVG | SoDHA HA SD | SoDHA OCP AVG | SoDHA OCP SD | PS HA AVG | PS HA SD |
|---|---|---|---|---|---|---|---|---|---|
| LINE | L Humerus, Upper | 3.73 | 1.26 | 2.83 | 0.21 | 3.60 | 0.40 | | |
| | R Humerus, Upper | 4.34 | 0.11 | 4.36 | 1.92 | 3.77 | 2.13 | | |
| | L Humerus, Lower | | | | | | | | |
| | R Humerus, Lower | | | | | | | | |
| | L Femur | | | 2.57 | 0.17 | | | 4.17 | 2.44 |
| | R Femur | | | 4.06 | 1.78 | | | 3.98 | 1.37 |
| GAP | L Humerus, Upper | 0.69 | 0.52 | 1.98 | 0.23 | 1.05 | 0.37 | | |
| | R Humerus, Upper | 1.04 | 0.19 | 1.29 | 0.41 | 1.30 | 0.64 | | |
| | L Humerus, Lower | 1.63 | 0.24 | | | | | | |
| | R Humerus, Lower | | | | | | | | |
| | L Femur | | | 1.20 | 0.86 | | | 1.56 | 0.15 |
| | R Femur | | | 2.28 | 0.16 | | | 2.49 | 1.08 |

EXAMPLE 18

Organic Solvent Exchange and Supercritical $CO_2$ Solvent Extraction

Coated Gription™ and grit blast-flat coupons are rinsed with DI water after forming the SoDHA coating as described in Example 6. Residual aqueous solvent is exchanged with ethanol 3 times within a soaking step. Soak periods studied are 1 and 20 hours. After organic solvent exchange in ethanol, coupons are the placed on a rack and inserted into a 100 ml stainless steel vessel. The coupons are covered with ethanol and the top vessel end-cap is closed. The $CO_2$ flow direction is from the top of the vessel and out the bottom. The vessel is pressurized to 100 bar with liquid $CO_2$ and the liquid ethanol is displaced with liquid $CO_2$ at room temperature at approximately 2 liters/minute of gaseous $CO_2$ flow. The displacement time is approximately ½ hour. After all the ethanol is displaced, the vessel is heated to 38° C. and dried for 4 hours with supercritical $CO_2$ at a flow rate of 5 liters/min gas. After the allotted drying time of 4 hours, the vessel is depressurized to atmosphere while maintaining the temperature above the $CO_2$ critical temperature of 32° C. The depressurization is conducted at approximately 1 liter/minute gas flow rate and lasted approximately ½ hour.

EXAMPLE 19

Re-Precipitation Via Hydrothermal Treatment of SoDHA

The SoDHA coated coupons prepared according to Example 6 were quickly transferred from DI water to a glass bottle containing either 15 mL 40 mM phosphate (Pi) syrup prepared according to Example 4 or 15 ml 2.2262 mM mM Pi stock prepared according to Example 4. The glass bottle was then sealed with a cap. The hydrothermal treatment of SoDHA films was performed at 90° C. for 2 hours. After hydrothermal treatment, the SoDHA coated coupons were rinsed with DI water excessively for one minute and placed in a 60° C. oven to dry for 1 hour.

Figure 33A:
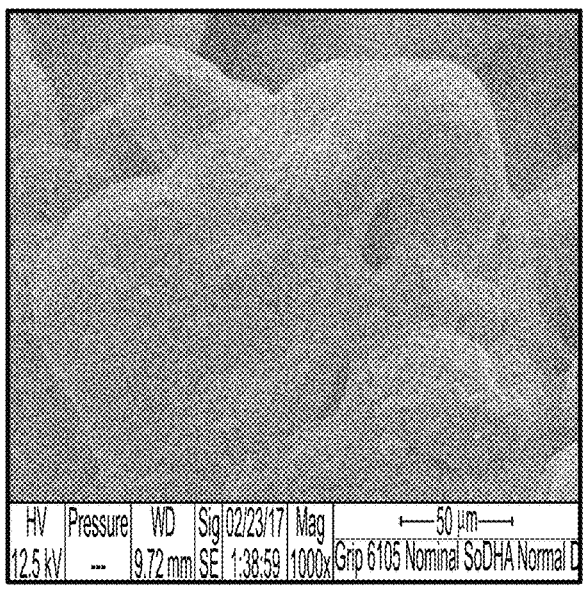
FIG. 33A is an SEM image of an oven-dried SoDHA coating without post-processing at 1000× magnification.
Figure 33B:
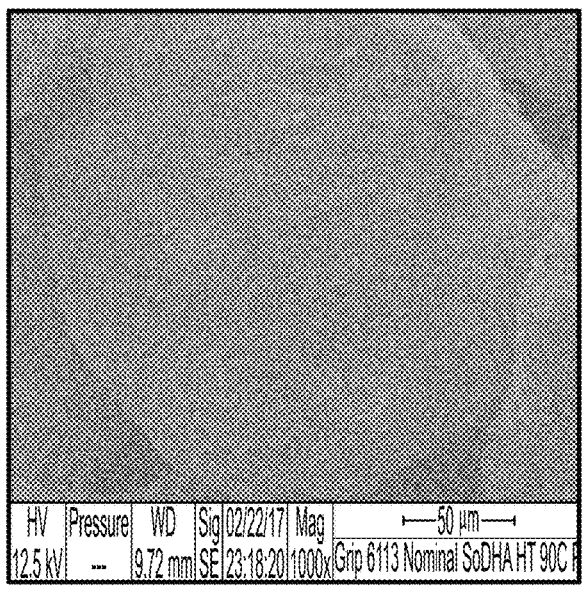
FIG. 33B is an SEM image of a hydrothermally treated SoDHA coating at 1000× magnification.
Figure 34:
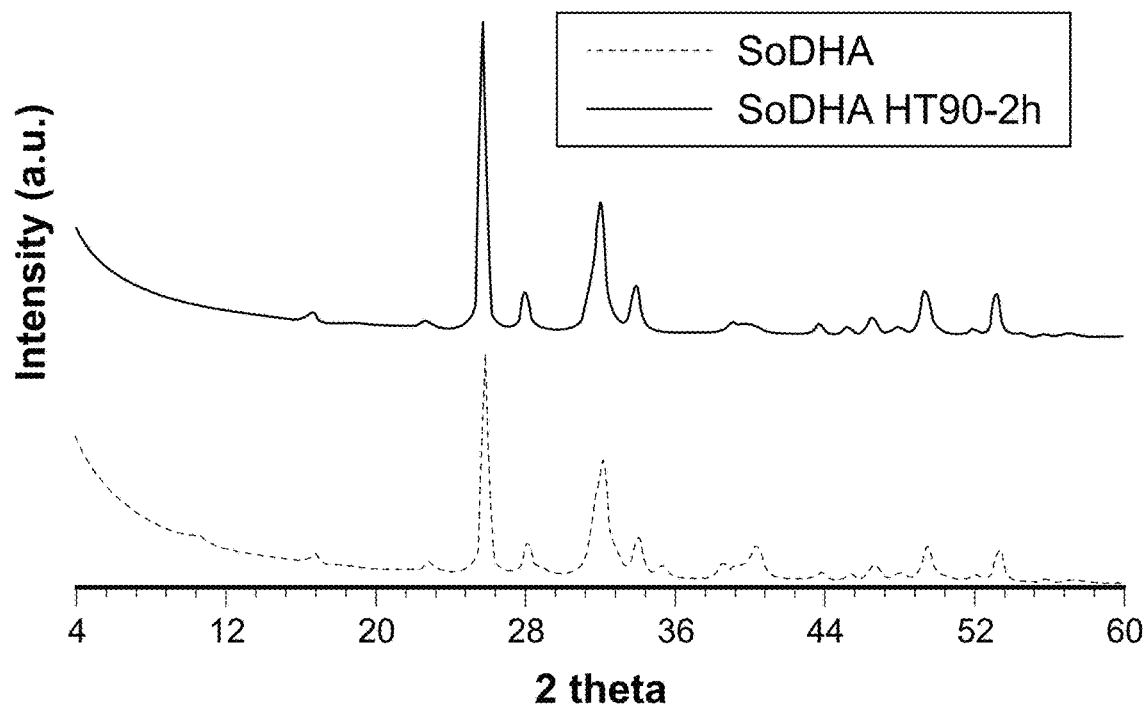
FIG. 34 shows superimposed XRD scans of an oven-dried SoDHA coating without post-processing and a hydrothermally treated SoDHA coating.

The surface morphologies of the SoDHA and hydrothermally treated SoDHA (SoDHA-HT) films were examined by a scanning electron microscope (FE-SEM, Quanta 600 F). Scanning electron microscopy images for SoDHA and SoDHA-HT are shown in FIGS. 33A and 33B, respectively. The phase composition of the SoDHA and SoDHA-HT films was identified by X-ray diffractometry (Philips Analytical), using Cu Kα radiation at 45 kV, 40 mA. The XRD patterns of the SoDHA film and the SoDHA film (hydrothermally treated in Pi stock at 90° C. for 2 hr) were collected between 4°-60° (2θ) at 0.02° step and 0.01°/s, as shown in FIG. 34. The XRD results revealed that hydrothermal treatment does not introduce new phases.

EXAMPLE 20

Crack Quantification

Figures 35A, 35B:
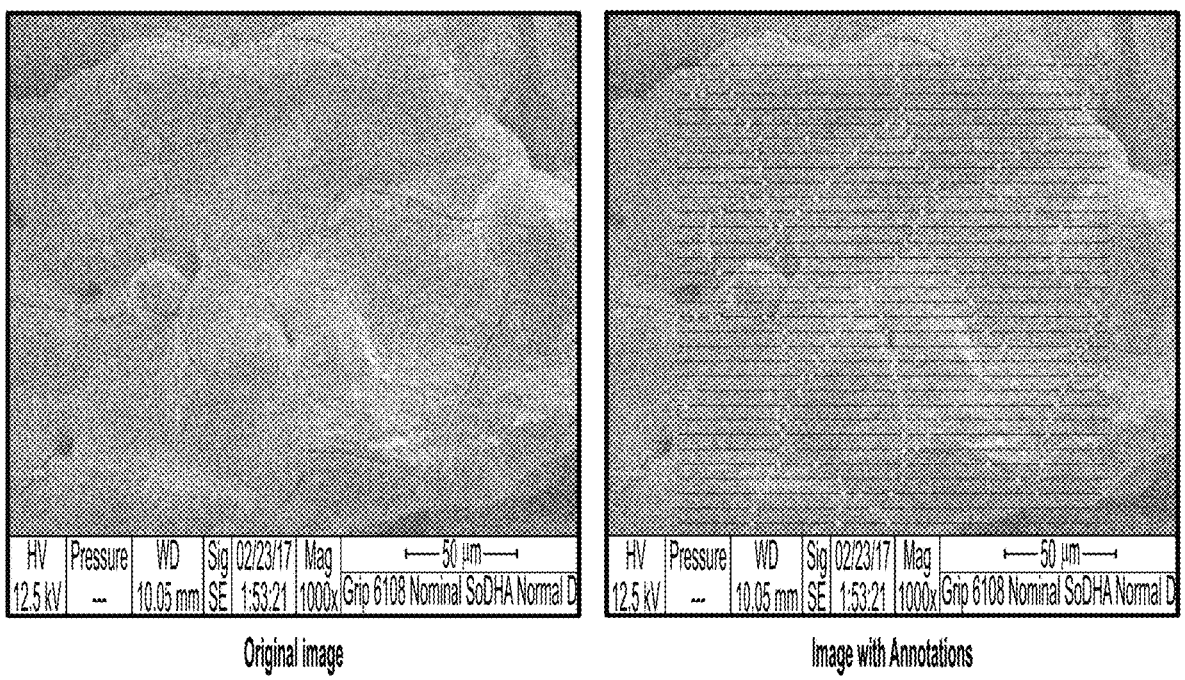
FIGS. 35A and 35B show representative images illustrating a crack density quantification method.

The crack improvement benefit of post treatment according to Examples 18 and 19 was quantified using image analysis by measuring the number of crack intersections on a predetermined horizontal grid. Images were taken at 1000× on the FEI Quanta 600 F SEM, and then imported into the Axio Vision software (AxioVision SE64 Release 4.9.1.0, from Carl Zeiss Microscopy GmbH) and 25 horizontal grid lines 193.5 μm in length and vertically 6 μm apart were placed over most of the image. The intercepts of the cracks in the image and grid lines were then manually marked. The intercepts were chosen manually by the operator to eliminate software driven errors. The number of intersections in this given area was used as a quantitative measure of the extent of surface cracking of SoDHA coatings. Representative images illustrating the method are shown in FIGS. 35A and 35B.

Nominal SoDHA with optimized hydrothermal treatment parameters exhibited minimal cracking, with fewer than 50 intercepts. The number of crack intersections and intercept density for representative regularly dried and post-processed coatings are shown in Table 11.

TABLE 11

Average crack intercept counts and crack intercept density comparison with and without post-processing

| Sample | Average number of intercepts | Average intercept density (intercepts/mm$^2$) |
|---|---|---|
| Gription Disk-Nominal SoDHA no post-processing step | 137 | 3659 |
| Gription Disk-Nominal SoDHA-2 hour hydrothermal treatment, 90° C. in phosphate stock solution | 50 | 1335 |

While the invention has been illustrated and described in detail in the drawings and foregoing description, such an illustration and description is to be considered as exemplary and not restrictive in character, it being understood that only the illustrative embodiments have been shown and described and that all changes and modifications that come within the spirit of the invention are desired to be protected.

There is a plurality of advantages of the present invention arising from the various features of the HA and OCP coatings described herein. It will be noted that alternative embodiments of each of the coatings of the present invention may not include all of the features described yet benefit from at least some of the advantages of such features. Those of ordinary skill in the art may readily devise their own implementations of calcium phosphate coatings that incorporate one or more of the features of the present invention and fall within the spirit and scope of the present invention as defined by the appended claims.

What is claimed is:

1. An orthopedic implant comprising a metal surface and a calcium phosphate layer disposed on at least part of the metal surface, wherein, the calcium phosphate layer, when subjected to XRD, produces a (002) XRD peak and a (112) XRD peak, and the (002) XRD peak has an intensity 1.5 to 10 times greater than the (112) XRD peak.

2. The orthopedic implant of claim 1, wherein the calcium phosphate layer comprises a hydroxyapatite.

3. The orthopedic implant of claim 2, wherein the calcium phosphate layer has an average crystallite size of about 50 nm to about 100 nm in the [001] direction.

4. The orthopedic implant of claim 2, wherein the calcium phosphate layer continuously dissolves for more than 24 hours in vitro.

5. The orthopedic implant of claim 2, wherein the calcium phosphate layer comprises about 0 wt % to about 5 wt % carbonate.

6. The orthopedic implant of claim 2, wherein the coating is in contact with the metal surface.

7. The orthopedic implant of claim 6, wherein the metal surface comprises a titanate.

8. The orthopedic implant of claim 7, wherein the metal surface comprises sodium titanate.

9. The orthopedic implant of claim 2, wherein the hydroxyapatite has a crystallinity of about 70 wt % to about 100 wt %.

10. The orthopedic implant of claim 2, wherein the calcium phosphate layer has a phase purity of crystalline hydroxyapatite of greater than 90%.

11. The orthopedic implant of claim 2, wherein the calcium phosphate layer has a shear strength of about 20 MPa to about 80 MPa as determined according to ASTM F1044.

12. The orthopedic implant of claim 2, wherein the calcium phosphate layer has a tensile strength of about 50 MPa to about 100 MPa as determined according to ASTM F1147.

13. The orthopedic implant of claim 2, wherein the calcium phosphate layer, in the absence of colorants, is transparent or translucent.

14. The orthopedic implant of claim 2, wherein the calcium phosphate layer has a surface area of about 15 m$^2$/g to about 200 m$^2$/g.

* * * * *